United States Patent
Sun et al.

(10) Patent No.: US 11,622,961 B2
(45) Date of Patent: Apr. 11, 2023

(54) COMBINATION THERAPIES FOR TREATING CANCER

(71) Applicant: TESARO, INC., Waltham, MA (US)

(72) Inventors: Kaiming Sun, Waltham, MA (US); Jing Yu Wang, Waltham, MA (US); Zebin Wang, Waltham, MA (US)

(73) Assignee: Tesaro, Inc., Wilmington, DE (US)

( * ) Notice: Subject to any disclaimer, the term of this patent is extended or adjusted under 35 U.S.C. 154(b) by 0 days.

(21) Appl. No.: 16/614,131

(22) PCT Filed: May 18, 2018

(86) PCT No.: PCT/US2018/033437
§ 371 (c)(1),
(2) Date: Nov. 15, 2019

(87) PCT Pub. No.: WO2018/213732
PCT Pub. Date: Nov. 22, 2018

(65) Prior Publication Data
US 2021/0008053 A1    Jan. 14, 2021

Related U.S. Application Data

(60) Provisional application No. 62/508,363, filed on May 18, 2017, provisional application No. 62/508,481, filed on May 19, 2017, provisional application No. 62/578,204, filed on Oct. 27, 2017.

(51) Int. Cl.
*A61K 31/4439* (2006.01)
*A61P 35/00* (2006.01)
*A61K 45/06* (2006.01)

(52) U.S. Cl.
CPC .......... *A61K 31/4439* (2013.01); *A61P 35/00* (2018.01); *A61K 45/06* (2013.01)

(58) Field of Classification Search
None
See application file for complete search history.

(56) References Cited

U.S. PATENT DOCUMENTS

| | | | |
|---|---|---|---|
| 7,595,048 B2 | 9/2009 | Honjo et al. | |
| 8,071,623 B2 | 12/2011 | Jones et al. | |
| 8,217,149 B2 | 7/2012 | Irving et al. | |
| 8,436,185 B2 | 5/2013 | Foley et al. | |
| 8,728,474 B2 | 5/2014 | Honjo et al. | |
| 8,779,108 B2 | 7/2014 | Queva et al. | |
| 8,952,136 B2 | 2/2015 | Carven et al. | |
| 9,624,298 B2 | 4/2017 | Nastri et al. | |
| 9,707,302 B2 | 7/2017 | Goldenberg et al. | |
| 9,815,897 B2 | 11/2017 | King et al. | |
| 10,738,117 B2 | 8/2020 | King et al. | |
| 2009/0123419 A1 | 5/2009 | Sherman et al. | |
| 2010/0003192 A1 | 1/2010 | Sherman et al. | |
| 2012/0207856 A1 | 8/2012 | Ajay et al. | |
| 2012/0269861 A1 | 10/2012 | Sherman et al. | |
| 2015/0071910 A1 | 3/2015 | Kowanetz et al. | |
| 2015/0344968 A1 | 12/2015 | Johnson | |
| 2016/0075783 A1 | 3/2016 | King et al. | |
| 2016/0296633 A1 | 10/2016 | Goldenberg et al. | |
| 2016/0340428 A1 | 11/2016 | Yang | |
| 2017/0000885 A1 | 1/2017 | Rhee et al. | |
| 2017/0049767 A1 | 2/2017 | Blanchette et al. | |
| 2018/0311224 A1 | 11/2018 | Hedley et al. | |
| 2020/0016142 A1 | 1/2020 | McGurk et al. | |
| 2020/0017462 A1 | 1/2020 | Wu et al. | |
| 2020/0055837 A1 | 2/2020 | Stewart et al. | |
| 2020/0289493 A1 | 9/2020 | Bobilev et al. | |
| 2020/0299387 A1 | 9/2020 | Mikule | |
| 2020/0306236 A1 | 10/2020 | Mikule | |
| 2021/0106574 A1 | 4/2021 | Feng et al. | |
| 2022/0048983 A1 | 2/2022 | Milenkova-Ilieva et al. | |

FOREIGN PATENT DOCUMENTS

| | | |
|---|---|---|
| CN | 110831580 | 2/2020 |
| EA | 201992594 | 3/2020 |
| EP | 0325199 | 10/1993 |
| EP | 0357061 | 6/1994 |
| EP | 2007733 | 5/2016 |
| EP | 3621592 | 3/2020 |
| JP | 2011509252 | 3/2011 |
| JP | 2011509253 | 3/2011 |
| JP | 2017504623 | 2/2017 |
| WO | WO 2007113596 | 10/2007 |
| WO | WO 2008084261 | 7/2008 |
| WO | WO 2009/064738 | 5/2009 |
| WO | WO 2009087381 | 7/2009 |
| WO | WO 2010/091140 | 8/2010 |
| WO | WO 2011/153383 | 12/2011 |
| WO | WO 2011/160063 | 12/2011 |

(Continued)

OTHER PUBLICATIONS

Adams et al., "Phase 2 study of pembrolizumab (pembro) monotherapy for previously treated metastatic triple-negative breast cancer (mTNBC): Keynote-086 cohort A", Journal of Clinical Oncology, May 2017, 35(15)1008 (abstract only).

Agata et al., "Expression of the PD-1 antigen on the surface of stimulated mouse T and B lymphocytes", International Immunology, May 1996, 8(5):765-772.

Boland et al., "Microsatellite instability in colorectal cancer", Gastroenterology, 2010, 138(6):2073-2087.

ClinicalTrials.gov [online], "Niraparib in Combination With Pembrolizumab in Patients With Triplenegative Breast Cancer or Ovarian Cancer (TOPACIO)", Jan. 18, 2016, retrieved on Feb. 16, 2021, retrieved from URL <"https://clinicaltrials.gov/ct2/show/NCT02657889?term=NCT+02657889&draw=2&rank=1">, 10 pages.

De la Chapelle et al., "Clinical Relevance of Microsatellite Instability in Colorectal Cancer", Journal of Clinical Oncology, 2010, 28(20):3380-3387.

(Continued)

*Primary Examiner* — Brian J Davis
(74) *Attorney, Agent, or Firm* — Fish & Richardson P.C.

(57) ABSTRACT

The present invention provides methods of treatment for cancer(s) through combination therapy with an agent that inhibits poly [ADP-ribose] polymerase (PARP) signaling and an agent that regulates activity within the tumor microenvironment.

10 Claims, 12 Drawing Sheets

(56) References Cited

FOREIGN PATENT DOCUMENTS

| WO | WO 2012/027224 | 3/2012 |
|---|---|---|
| WO | WO 2013/182645 | 12/2013 |
| WO | WO 2014088983 | 6/2014 |
| WO | WO 2014088984 | 6/2014 |
| WO | WO 2014/138101 | 9/2014 |
| WO | WO 2014179664 | 11/2014 |
| WO | WO 2015/086473 | 6/2015 |
| WO | WO 2015/108986 | 7/2015 |
| WO | WO 2015/116868 | 8/2015 |
| WO | WO 2015/184145 | 12/2015 |
| WO | WO 2016094391 | 6/2016 |
| WO | WO 2016/126858 | 8/2016 |
| WO | WO 2016/161270 | 10/2016 |
| WO | WO 2016/200835 | 12/2016 |
| WO | WO 2016/210108 | 12/2016 |
| WO | WO 2017/075091 | 5/2017 |
| WO | WO 2017/142871 | 8/2017 |
| WO | WO 2018/005818 | 1/2018 |
| WO | WO 2018/059437 | 4/2018 |
| WO | WO 2018/085469 | 5/2018 |
| WO | WO 2018085468 | 5/2018 |
| WO | WO 2018/129553 | 7/2018 |
| WO | WO 2018129559 | 7/2018 |
| WO | WO 2018/201096 | 11/2018 |
| WO | WO 2018200517 | 11/2018 |
| WO | WO 2018208968 | 11/2018 |
| WO | WO 2018213732 | 11/2018 |
| WO | WO 2019/005762 | 1/2019 |
| WO | WO 2019067634 | 4/2019 |
| WO | WO 2019067978 | 4/2019 |
| WO | WO 2019071123 | 4/2019 |
| WO | WO 2019133697 | 7/2019 |
| WO | WO 2019152989 | 8/2019 |

OTHER PUBLICATIONS

Domagala et al., "BRCA1/2-negative hereditary triple-negative breast cancers exhibit BRCAness: Hereditary triple-negative breast cancer and BRCAness", International Journal of Cancer, Apr. 2017, 140(7):1545-1550.
Dougherty et al., "Biological and clinical evidence for somatic mutations in BRCA1 and BRCA2 as predictive markers for olaparib response in high-grade serous ovarian cancers in the maintenance setting", Oncotarget, Jul. 2017, 8(27):43653-43661.
PCT International Preliminary Report on Patentability in International Application No. PCT/US2018/053542, dated Mar. 31, 2020, 5 pages.
PCT International Preliminary Report on Patentability in International Application No. PCT/US2018/054606, dated Apr. 8, 2020, 7 pages.
PCT International Preliminary Report on Patentability in International Application No. PCT/US2018/067653, dated Jun. 30, 2020, 11 pages.
PCT International Preliminary Report on Patentability in International Application No. PCT/US2019/049346, dated Mar. 9, 2021, 15 pages.
PCT International Search Report and Written Opinion in International Application No. PCT/US2018/067653, dated May 27, 2019, 18 pages.
Du Bois et al., "Addition of Epirubicin as a Third Drug to Carboplatin-Paclitaxel in First-Line Treatment of Advanced Ovarian Cancer: A Prospectively Randomized Gynecologic Cancer Intergroup Trial by the Arbeitsgemeinschaft Gynaekologische Onkologie Ovarian Cancer Study Group and the Groupe d'Investigateurs Nationaux pour l'Etude des Cancers Ovariens", Journal of Clinical Oncology, Mar. 2006, 24(7):1127-1135.
Duggan et al., "Microsatellite Instability in Sporadic Endometrial Carcinoma", Journal of the National Cancer Institute, Aug. 1994, 86(16):1216-1221.
Gadducci et al., "PARP inhibitors alone and in combination with other biological agents in homologous recombination deficient epithelial ovarian cancer: From the basic research to the clinic", Critical Reviews in Oncology/Hematology, Jun. 2017, 114:153-165.
Goyal et al., "Hereditary cancer syndromes: utilizing DNA repair deficiency as therapeutic target", Familial Cancer, Feb. 2016, 15:359-366.
Gurin et al., "Causes and Consequences of Microsatellite Instability in Endometrial Carcinoma", Molecular Biology and Genetics, Jan. 1999, 59(2):462-466.
Hamanishi et al., "Safety and Antitumor Activity of Anti-PD-1 Antibody, Nivolumab, in Patients With Platinum-Resistant Ovarian Cancer", Journal of Clinical Oncology, Sep. 2015, 33:4015-4022.
Heong et al., "Update on immune checkpoint inhibitors in gynecological cancers", Journal of Gynecological Oncology, Mar. 2017, 28(2):e20, 19 pages.
Javle et al., "The role of PARP in DNA repair and its therapeutic exploitation", British Journal of Cancer, Oct. 2011, 105(8):1114-1122.
Konstantinopoulos et al., "Dose-finding combination study of niraparib and pembrolizumab in patients (pts) with metastatic triple-negative breast cancer (TNBC) or recurrent platinum-resistant epithelial ovarian cancer (OC) (TOPACIO/Keynote-162)", Annals of Oncology, Sep. 2017, 28(5):V406-V407.
Konstantinopoulos et al., "Topacio: Preliminary activity and safety in patients (pts) with platinum-resistant ovarian cancer (PROC) in a phase 1/2 study of niraparib in combination with pembrolizumab", Gynecologic Oncology, Jun. 2018, 149(Suppl. 1):246.
Konstantinopoulos, "Pembrolizumab Plus Niraparib Shows Promise in Ovarian Cancer", SGO Annual Meeting, Mar. 27, 2018, retrieved on Feb. 16, 2021, retrieved from URL <"https://www.onclive.com/view/pembrolizumab-plus-niraparib-shows-promise-in-ovarian-cancer">, 3 pages.
McCans, "Germline BRCA mutation testing to determine eligibility for olaparib maintenance therapy in women with platinum-sensitive relapsed ovarian cancer (including fallopian tube or primary peritoneal cancer) with high grade serous features or a high grade serous component. Applicant Submitted Proposed Protocol", MSAC Application 1380, Dec. 2014, 32 pages.
Moschetta et al., "BRCA somatic mutations and epigenetic BRCA modifications in serous ovarian cancer", Annals of Oncology, Aug. 2016, 27(8):1449-1455.
Myers et al., "Optimal alignments in linear space", CABIOS, 1988, 4(1):11-17.
Popat et al., "Systematic Review of Microsatellite Instability and Colorectal Cancer Prognosis", Journal of Clinical Oncology, Jan. 2005, 23(3):609-618.
Umar et al., "Revised Bethesda Guidelines for Hereditary Nonpolyposis Colorectal Cancer (Lynch Syndrome) and Microsatellite Instability", Journal of the National Cancer Institute, Feb. 2004, 96(4):261-268.
Zhu et al., "Programmed death-1 pathway blockade produces a synergistic antitumor effect: combined application in ovarian cancer", Journal of Gynecologic Oncology, Sep. 2017, 28(5):e64.
[No. author listed] "Integrated genomic analyses of ovarian carcinoma," Nature, 2011, 474:609-15.
Anonymous, "History of Changes for Study: NCT03308942," Jun. 18, 2018, retrieved on Oct. 26, 2020, retrieved from URL: https://clinicaltrials.gov/ct2/history/NCT033089427V_5=View#StudyPageTop, 15 pages.
Anonymous, "TESARO announces expansion to second stage of JASPER trial of ZEJULA in combination with TSR-042 in non-small cell lung cancer," Sep. 4, 2018, retrieved on Oct. 26, 2020, retrieved from URL: https://www.globenewswire.com/news-release/2018/09/04/1565255/0/en/TESARO-Announces-Expansion-to-Second-Stage-of-JASPER-Trial-of-ZEJULA-in-Combination-With-TSR-042-in-Non-Small-Cell-Lung-Cancer.html, 4 pages.
Baixeras et al., "Characterization of the lymphocyte activation gene 3-encoded protein. A new ligand for human leukocyte antigen class II antigens," J. Exp. Med., 1992, 176:327-337.
Berge et al., "Pharmaceutical Salts," J Pharmaceutical Sciences, 1977, 66(1):1-19.

(56) References Cited

OTHER PUBLICATIONS

Bhatia et al., "Immunobiology of Merkel cell carcinoma: implications for immunotherapy of a polyomavirus-associated cancer," Curr. Oncol. Rep., 2011, 13(6):488-497.

Bois et al., "A phase I and pharmacokinetic study of novel taxane BMS-188797 and cisplatin in patients with advanced solid tumors," Br. J Cancer, 2006, 94(1):79-84.

Brinkman et al., "The making of bispecific antibodies," Mabs, 2017, 9(2):182-212.

Dann et al., "BRCA 1/2 mutations and expression: response to platinum chemotherapy in patients with advanced stage epithelial ovarian cancer," Gynecol. Oncol., 2012, 125(3):677-82.

Davies et al., "Antibody-antigen complexes," Annual Rev Biochem., 1990, 59:439-473.

Eisenhauer et al., "New response evaluation criteria in solid tumors: Revised RECIST guideline (version 1.1.)," Eur. J. of Cancer, 2009, 45(2):228-247.

Erdal et al., "A prosurvival DNA damage-induced cytoplasmic interferon response is mediated by end resection factors and is limited by Trex1," Genes Dev. 2017, 31:353-369.

Gelmon et al., "Olaparib in patients with recurrent high-grade serous or poorly differentiated ovarian carcinoma or triple-negative breast cancer: a phase 2, multicentre, open-label, non-randomised study," Lancet Oncol., 2011, 12:852-861.

Guo et al., "Combined TIM-3 blockade and CD137 activation affords the long-term protection in a murine model of ovarian cancer," Journal of Translational Medicine, 2013, 11:215.

Hennessy et al., "Somatic Mutations in BRCA1 and BRCA2 Could Expand the Number of Patients That Benefit From Poly (ADP Ribose) Polymerase Inhibitors in Ovarian Cancer," J Clin Oncol. 2010, 28(22):3570-3576.

Higuchi et al., "CTLA-4 Blockade Synergizes Therapeutically with PARP Inhibition in BRCA1-Deficient Ovarian Cancer," Cancer Immunol Res., 2015, 3:1257-1268.

Huang et al., "Role of LAG-3 in regulatory T cells," Immunity, 2004, 21:503-513.

Huang et al., "The PARP1 inhibitor BMN 673 exhibits immunoregulatory effects in a Brca1(-/-) murine model of ovarian cancer," Biochem Biophys Res Commun., 2015, 463:551-556.

Huard et al., "Characterization of the major histocompatibility complex class II binding site on LAG-3 protein," Proc. Natl. Acad. Sci. USA, 1997, 94(11):5744-5749.

Huard et al., "Lymphocyte-activation gene 3/major histocompatibility complex class II interaction modulates the antigenic response of CD4+ T lymphocytes," Eur. J. Immunol., 1994, 24:3216-3221.

Huard et al., "T cell major histocompatibility complex class II molecules down-regulate CD4+ T cell clone responses following LAG-3 binding," Eur. J. Immunol., 1996, 26:1180-1186.

Jiao et al., "PARP inhibitor upregulates PD-L1 expression and enhances cancer-associated immunosuppression," Clinical Cancer Research, 2017, 23(14):3711-3720.

Kelley et al., "Targeting DNA repair pathways for cancer treatment: what's new?," Future Oncol., 2014, 10(7):1215-37.

Kim et al., "PD-L1 expression on immune cells, but not on tumor cells, is a favorable prognostic factor for head and neck cancer patients," Sci. Rep., 2016, 6:36956.

Le et al., "PD-1 Blockade in Tumors with Mismatch-Repair Deficiency," N. Engl. J. Med., 2015, 372(26):2509-2520.

Ledermann et al., "Olaparib maintenance therapy in patients with platinum-sensitive relapsed serous ovarian cancer: a preplanned retrospective analysis of outcomes by BRCA status in a randomised phase 2 trial," The Lancet, 2014, 15(8):852-61.

Ledermann et al., "Olaparib Maintenance Therapy in Platinum-Sensitive Relapsed Ovarian Cancer," New England Journal of Medicine, 2012, 366:1382-92.

Malmqvist, "Biospecific interaction analysis using biosensor technology," Nature, 1993, 361:186-187.

Meyers et al., "Optimal Alignments in Linear Space," Comput. Appl. Biosci., 1989, 4(1):11-17.

Mirza et al., "Niraparib Maintenance Therapy in Platinum-Sensitive Recurrent Ovarian Cancer," The New England Journal of Medicine, 2016, 375(22):2154-2164.

Mouw et al., "DNA Damage and Repair Biomarkers of Immunotherapy Response," Cancer Discov., 2017, 7:675-693.

Murali, "Classification of endometrial carcinoma: more than two types," Lancet Oncol., 2014, 15(7):e268-78.

Ngiow et al., "Anti-TIM3 antibody promotes T cell IFN-γ-mediated antitumor immunity and suppresses established tumors," Cancer Res., 2011, 71:3540-3551.

Ngiow et al., "Prospects for TIM3-Targeted Antitumor Immunotherapy," Cancer Res., 2011, 71(21):6567-6571.

Nichino et al., "Developing a common language for tumor response to immunotherapy: immune-related response criteria using unidimensional measurements," Clin. Cancer Res., 2013, 19(14):3936-43.

Patnaik et al., "Phase I study of MK-3475 (anti-PD-1 monoclonal antibody) inpatients with advanced solid tumors," Journal of Clinical Oncology, 2012, 30(15):Abstract #2512.

PCT International Search Report and Written Opinion in International Appln. No. PCT/US2018/053542, dated Dec. 14, 2018, 8 pages.

PCT International Search Report and Written Opinion in International Appln. No. PCT/US2018/054606, dated Mar. 28, 2019, 15 pages.

PCT International Search Report and Written Opinion in International Appln. PCT/US2019/049346, dated Apr. 9, 2020, 19 pages.

PCT Invitation to Pay Additional Fees in International Appln. No. PCT/US2018/054606, dated Feb. 5, 2019, 10 pages.

PCT Invitation to Pay Additional Fees in International Appln. No. PCT/US2018/067653, dated Apr. 2, 2019, 18 pages.

Pearson, "Using the FASTA program to search protein and DNA sequence databases," Methods Mol. Biol., 1994, 24:307-331.

Pearson, "Using the FASTA program to search protein and DNA sequence databases," Methods Mol. Biol., 1994, 25:365-389.

Pfisterer et al., "Gemcitabine plus carboplatin compared with carboplatin in patients with platinum-sensitive recurrent ovarian cancer: an intergroup trial of the AGO-OV AR, the NCIC CTG, and the EORTC GCG," J Clin. Oncol., 2006, 24(29):4699-707.

Popova et al., "Ploidy and large-scale genomic instability consistently identify basal-like breast carcinomas with BRCA1/2 inactivation," Cancer Res, 2012, 72:5454-62.

Porichis et al., "Role of PD-1 in HIV Pathogenesis and as Target for Therapy," Curr. HIV/AIDS Rep., 2012, 9(1):81-90.

Rom-Jurek et al., "Regulation of Programmed Death Ligand 1 (PD-L1) Expression in Breast Cancer Cell Lines In Vitro and in Immunodeficient and Humanized Tumor Mice" Int. J. Mol. Sci., 2018, 16:563.

Rustin et al., "Definitions for Response and Progression in Ovarian Cancer Clinical Trials Incorporating RECIST 1.1 and CA 125 Agreed by the Gynecological Cancer Intergroup (GCIG)," Int J Gynecol Cancer, 2011, 21:419-423.

Sakuishi et al., "Targeting Tim-3 and PD-1 pathways to reverse T cell exhaustion and restore anti-tumor immunity," J. Exp. Med., 2010, 207:2187-2194.

Sandhu et al., "The poly(ADP-ribose) polymerase inhibitor niraparib (MK4827) in BRCA mutation carriers and patients with sporadic cancer: a phase 1 dose-escalation trial," Lancet Oncol, 2013, 14:882-892.

Sharma et al., "Primary, Adaptive, and Acquired Resistance to Cancer Immunotherapy," Cell, 2017, 168(4):707-723.

Shukuya et al., "Predictive Markers for the Efficacy of Anti-PD-1/PD-L1 Antibodies in Lung Cancer," Journal of Thoracic Oncology, 2016, 11(7):976-988.

Sierro et al., "The CD4-like molecule LAG-3, biology and therapeutic applications," Expert Opin. Ther. Targets., 2011, 15(1):91-101.

Tang et al., "Programmed Death 1 Pathway Inhibition in Metastatic Renal Cell Cancer and Prostate Cancer," Current Oncology Reports, 2013, 15(2):98-104.

Topalian et al., "Safety, Activity, and Immune Correlates of anti-PD-1 Antibody in Cancer," New England J. Med., 2012, 366(26):2443-2454.

(56) References Cited

OTHER PUBLICATIONS

Turner et al., "Hallmarks of 'BRCAness' in sporadic cancers," Nat. Rev. Cancer, 2004, 4(10):814-19.
Udall et al., "PD-L1 diagnostic tests: a systematic literature review of scoring algorithms and test-validation metrics," Diagnostic Pathology, 2018, 13:12.
Weber, "Immune Checkpoint Proteins: A New Therapeutic Paradigm for Cancer—Preclinical Background: CTLA-4 and PD-1 Blockade," Semin. Oncol., 2010, 37(5):430-439.
Westrop et al., "Opportunities for immunotherapy in microsatellite instable colorectal cancer," Cancer Immunol. Immunother., 2016, 65(10):1249-1259.
Woo et al., "Immune inhibitory molecules LAG-3 and PD-1 synergistically regulate T-cell function to promote tumoral immune escape," Cancer Res., 2012, 72:917-927.
Woof et al., "Human antibody-Fc receptor interactions illuminated by crystal structures," Nat. Rev. Immunol., 2004, 4:89-99.
Workman et al., "Negative regulation of T cell homeostasis by lymphocyte activation gene-3 (CD223)," J. Immunol., 2005, 174:688-695.
U.S. Appl. No. 16/608,059, filed Oct. 24, 2019, Stewart et al.
American Cancer Society. Cancer Facts & Figures 2016. Atlanta: American Cancer Society 2016; http://www.cancer.org/acs/groups/content/@research/documents/document/acspc-047079.pdf.
Ascierto, Paolo A., et al. "Biomarkers for Immunostimulatory Monoclonal Antibodies in Combination Strategies for Melanoma and Other Tumor Types." Clinical cancer research (Print) 19.5 (2013): 1009-1020.
Andreae, Susanne, et al. "Maturation and activation of dendritic cells induced by lymphocyte activation gene-3 (CD223)." The Journal of Immunology 168.8 (2002): 3874-3880.
Barber, Daniel L., et al., "Restoring function in exhausted CD8 T cells during chronic viral infection." Nature 439.7077 (2006): 682-687.
Bennett, Frann, et al. "Program death-1 engagement upon TCR activation has distinct effects on costimulation and cytokine-driven proliferation: attenuation of ICOS, IL-4, and IL-21, but not CD28, IL-7, and IL-15 responses." The Journal of Immunology 170.2 (2003): 711-718.
Bertsias, George K., et al. "Genetic, Immunologic, and Immunohistochemical Analysis of the Programmed Death 1/Programmed Death Ligand 1 Pathway in Human Systemic Lupus Erythematosus." Arthritis & Rheumatism 60.1 (2009): 207-218.
Blackburn, Shawn D., et al. "Coregulation of CD8+ T cell exhaustion by multiple inhibitory receptors during chronic viral infection." Nature immunology 10.1 (2009): 29-37.
Blank, Christian, et al. "PD-L1/B7H-1 inhibits the effector phase of tumor rejection by T cell receptor (TCR) transgenic CD8+ T cells." Cancer research 64.3 (2004): 1140-1145.
Brown, Julia A., et al. "Blockade of programmed death-1 ligands on dendritic cells enhances T cell activation and cytokine production." The Journal of Immunology 170.3 (2003): 1257-1266.
Curtin, Nicola J. "Parp Inhibitors and Cancer Therapy." Poly (ADP-Ribosyl) ation. Springer, Boston, MA, 2006. 218-233.
Dong, Haidong, et al. "Tumor-associated B7-H1 promotes T-cell apoptosis: a potential mechanism of immune evasion." Nature medicine 8.8 (2002): 793-800.
Dutcher, Janice P., et al. "A phase II study of interleukin-2 and lymphokine-activated killer cells in patients with metastatic malignant melanoma." Journal of Clinical Oncology 7.4 (1989): 477-485.
Flies, Dallas B., et al. "Blockade of the B7-H1/PD-1 Pathway for Cancer Immunotherapy." Yale Journal of Biology and Medicine 84 (2011): 409-421.
Foa, Robert, et al. "Treatment of acute myeloid leukaemia patients with recombinant interleukin 2: a pilot study." British journal of haematology 77.4 (1991): 491-496.
Freeman, Gordon J., et al. "Engagement of the PD-1 immunoinhibitory receptor by a novel B7 family member leads to negative regulation of lymphocyte activation." The Journal of experimental medicine 192.7 (2000): 1027-1034.
Gill, Sonja J., et al. "Combinations of PARP inhibitors with temozolomide drive PARP1 trapping and apoptosis in Ewing's sarcoma." PloS one 10.10 (2015).
Grosso, Joseph F., et al. "LAG-3 regulates CD8+ T cell accumulation and effector function in murine self-and tumor-tolerance systems." The Journal of clinical investigation 117.11 (2007): 3383-3392.
Greenwald, Rebecca J., Gordon J. Freeman, and Arlene H. Sharpe. "The B7 family revisited." Annu. Rev. Immunol. 23 (2005): 515-548.
Hamanishi Junzo, et al. "Programmed cell death 1 ligand 1 and tumor-infiltrating CD8+ T lymphocytes are prognostic factors of human ovarian cancer." Proceedings of the National Academy of Sciences 104.9 (2007): 3360-3365.
Hirano, Fumiya, et al. "Blockade of B7-H1 and PD-1 by monoclonal antibodies potentiates cancer therapeutic immunity," Cancer research 65.3 (2005): 1089-1096.
Huang, Rong Rong, et al. "CTLA4 blockade induces frequent tumor infiltration by activated lymphocytes regardless of clinical responses in humans." Clinical Cancer Research 17.12 (2011): 4101-4109.
International Preliminary Report on Patentability dated Nov. 19, 2019 for PCT/US2018/033437.
International Search Report dated Oct. 17, 2018 for PCT/US2018/033437.
Ishida, Yasumasa, et al. "Induced expression of PD-1, a novel member of the immunoglobulin gene superfamily, upon programmed cell death." The EMBO journal 11.11 (1992): 3887-3895.
Iwai, Yoshiko, et al. "Involvement of PD-L1 on tumor cells in the escape from host immune system and tumor immunotherapy by PD-L1 blockade." Proceedings of the National Academy of Sciences 99.19 (2002): 12293-12297.
Iwai, Yoshiko, Seigo Terawaki, and Tasuku Honjo. "PD-1 blockade inhibits hematogenous spread of poorly immunogenic tumor cells by enhanced recruitment of effector T cells." International immunology 17.2 (2005): 133-144.
Kroner, Antje, et al. "A PD-1 polymorphism is associated with disease progression in multiple sclerosis." Annals of neurology 58.1 (2005): 50-57.
Latchman, Yvette, et al. "PD-L2 is a second ligand for PD-1 and inhibits T cell activation." Nature immunology 2.3 (2001): 261-268.
Lotze, M. T. et al., in "Interleukin 2", ed. K. A. Smith, Academic Press, Inc., San Diego, Calif., p. 237 (1988).
Ni, Ronghua, et al. "PD-1 gene haplotype is associated with the development of type 1 diabetes mellitus in Japanese children." Human genetics 121.2 (2007): 223-232.
Nielsen, C., et al. "Association of a putative regulatory polymorphism in the PD-1 gene with susceptibility to type 1 diabetes." Tissue antigens 62.6 (2003): 492-497.
Nishimura, Hiroyuki, et al. "Development of lupus-like autoimmune diseases by disruption of the PD-1 gene encoding an ITIM motif-carrying immunoreceptor." Immunity 11.2 (1999): 141-151.
Nomi, Takeo, et al. "Clinical significance and therapeutic potential of the programmed death-1 ligand/programmed death-1 pathway in human pancreatic cancer." Clinical cancer research 13.7 (2007): 2151-2157.
Okazaki, Taku, Yoshiko Iwai, and Tasuku Honjo. "New regulatory co-receptors: inducible co-stimulator and PD-1." Current opinion in immunology 14.6 (2002): 779-782.
Parry, Richard V., et al. "CTLA-4 and PD-1 receptors inhibit T-cell activation by distinct mechanisms." Molecular and cellular biology 25.21 (2005): 9543-9553.
Rosenberg, Steven A., et al. "A progress report on the treatment of 157 patients with advanced cancer using lymphokine-activated killer cells and interleukin-2 or high-dose interleukin-2 alone." New England Journal of Medicine 316.15 (1987): 889-897.
Rosenberg, Steven A. "The development of new immunotherapies for the treatment of cancer using interleukin-2. A review." Annals of surgery 208.2 (1988): 121.
Sharpe, Arlene H., et al. "The function of programmed cell death 1 and its ligands in regulating autoimmunity and infection." Nature immunology 8.3 (2007): 239-245.
Smith, Kendall A. "Interleukin-2: inception, impact, and implications." Science 240.4856 (1988): 1169-1176.

(56) References Cited

OTHER PUBLICATIONS

Tahoori, M. T., et al. "Association of programmed cell death-1 (PDCD-1) gene polymorphisms with rheumatoid arthritis in Iranian patients." *Clinical and Experimental Rheumatology-Incl Supplements* 29.5 (2011): 763.
Tentori, Lucio, and Grazia Graziani. "Pharmacological strategies to increase the antitumor activity of methylating agents." *Current medicinal chemistry* 9.13 (2002): 1285-1301.
Written Opinion of the International Searching Authority dated Oct. 17, 2018 for PCT/US2018/033437.
Yamazaki, Tomohide, et al. "Expression of programmed death I ligands by murine T cells and APC." *The Journal of Immunology* 169.10 (2002): 5538-5545.
Akbar et al., "A compact vocabulary of paratope-epitope interactions enables predictability of antibody-antigen binding," Cell Reports, Mar. 2021, 34:108856, 21 pages.
Alberts et al., "Analyzing Protein Structure and Function," Molecular Biology of the Cell, 4th edition. New York: Garland Science, 2002, 2 pages.
AlHilli et al., "In vivo anti-tumor activity of the PARP inhibitor niraparib in homologous recombination deficient and proficient ovarian carcinoma," Gynecologic Oncology, 2016, 143: 379-388.
Almagro et al., "Humanization of Antibodies," Frontiers in Bioscience, 2008, 13:1619-1633.
Altshuler et al., "Generation of Recombinant Antibodies and Means for Increasing Their Affinity," Biochemistiy (Moscow), 2010, 75(13):1584-1605.
CAS Registry No. 2022215-59-2 Substance Detail, CAS SciFinder, 2016, 5 pages.
ClinicalTrials.gov [online], "Avelumab in Patients With MSS, MSI-H and POLE-mutated Recurrent or Persistent Endometrial Cancer and of Avelumab/Talazoparib and Avelumab/Axitinib in Patients With MSS Recurrent or Persistent Endometrial Cancer", U.S. National Library of Medicine, Sep. 23, 2016, retrieved on Aug. 17, 2021, retrieved from URL <"https://clinicaltrials.gov/ct2/show/NCT02912572">, 13 pages.
ClinicalTrials.gov [online], "History of Changes for Study: NCT02660034: The Safety, Pharmacokinetics and Antitumor Activity of BGB-A317 in Combination With the BGB-290 in Subjects With Advanced Solid Tumors," U.S. National Library of Medicine, Aug. 13, 2017, retrieved from URL <"https://clinicaltrials.govict2/history/NCT02660034?V4=View#StudyPageTop">, 16 pages.
ClinicalTrials.gov [online], "History of Changes for Study: NCT02849496: Veliparib and Atezolizumab Either Alone or in Combination in Treating Patients With Stage III-IV Triple Negative Breast Cancer", U.S. National Library of Medicine, Sep. 12, 2016, retrieved on Aug. 17, 2021, retrieved from URL <"https://clinicaltrials.gov/ct2/history/NCT02849496?V_3=View#StudyPageTop">, 11 pages.
Crafton et al., "PARP inhibition and gynecologic malignancies: A review of current literature and on-going trials", Gynecologic Oncology, Jul. 2016, 142(3): 588-596.
Dedes et al., "Synthetic lethality of PARP inhibition in cancers lacking BRCA1 and BRCA2 mutations," Cell Cycle, 2011, 10(8): 1192-1199.
Dockery et al. "Rucaparib: the past, present, and future of a newly approved PARP inhibitor for ovarian cancer," OncoTargets and Therapy, 2017, 10: 3029-3037.
Edwards et al., "The Remarkable Flexibility of the Human Antibody Repertoire; Isolation of Over One Thousand Different Antibodies to a Single Protein, BLyS," J. Mol. Biol., 2003, 334:103-118.
Evans et al., "PARP inhibitors in ovarian cancer: evidence, experience and clinical potential" Therapeutic Advances in Medical Oncology, Feb. 2017, 9(4):253-267.
Friedlander et al., "A Phase 1/Ib Study of the Anti-PD-1 Monoclonal Antibody BGB-A317 (A317) in Combination with the PARP Inhibitor BGB-290 (290) in Advanced Solid Tumors," American Society of Clinical Oncology, Poster Presentation, Jun. 2, 2017, 1 page.
Hao et al., "A new oral polybosphate adenosine ribose polymerase inhibitor—niraparib," Clinical Medication Journal, Jun. 2017, 15(6): 13-17 (with English translation).

Hasegawa et al., "Single amino acid substitution in LC-CDR1 induces Russell body phenotype that attenuates cellular protein synthesis through elF2a phosphorylation and thereby downregulates IgG secretion despite operational secretory pathway traffic," mAbs, 2017, 9(5): 854-873.
Jones et al., "Discovery of 2-{4-[(3S)-Piperidin-3-yl]phenyl}-2H-indazole-7-carboxamide (MK-4827): A Novel Oral Poly(ADP-ribose)polymerase (PARP) Inhibitor Efficacious in BRCA-1 and -2 Mutant Tumors," Journal of Medicinal Chemistry, Oct. 2009, 52(22): 7170-7185.
Konstantinopoulos et al., "Phase I/II study of niraparib plus pembrolizumab in patients with triple-negative breast cancer or recurrent ovarian cancer," Meeting Abstract I 2016 ASCO Annual Meeting, re-printed in Journal of Clinical Oncology, 2016, 34(15), Suppl., 4 pages.
Landrum et al., "A phase I trial of pegylated liposomal doxorubicin (PLD), carboplatin, bevacizumab and veliparib in recurrent, platinum-sensitive ovarian, primary peritoneal, and fallopian tube cancer: An NRG Oncology/Gynecologic Oncology Group study", Gynecologic Oncology, Nov. 2015, 140(2):204-209.
Lee et al., "Safety and Clinical Activity of the Programmed Death-Ligand 1 Inhibitor Durvalumab in Combination With Poly (ADP-Ribose) Polymerase Inhibitor Olaparib or Vascular Endothelial Growth Factor Receptor 1-3 Inhibitor Cediranib in Women's Cancers: A Dose-Escalation, Phase I Study", Journal of Clinical Oncology, Jul. 2017, 35(19):2193-2202.
Lippow et al., "Computational design of antibody-affinity improvement beyond in vivo maturation," Nature Biotechnology, 2007, 25(10): 1171-1176.
Lo et al., "Conformational epitope matching and prediction based on protein surface spiral features," BMC Genomics, 2021, 22(Suppl. 2): 116, 16 pages.
Marchalonis et al., "The antibody repertoire in evolution: Chance, selection, and continuity," Developmental & Comparative Immunology, 2006, 30:223-247.
Marchetti et al., "Olaparib, PARP1 inhibitor in ovarian cancer", Expert Opinion on Investigational Drugs, Jul. 2012, 21(10): 1575-1584.
Marks et al., "How repertoire data are changing antibody science," J. Biol. Chem., 2020, 295(29): 9823-9837.
McLachlan et al., "The current status of PARP inhibitors in ovarian cancer", Tumori: A Journal of Experimental and Clinical Oncology, Oct. 2016, 102(5): 433-444.
Mendes-Pereira et al., "Synthetic lethal targeting of PTEN mutant cells with PARP inhibitors," EMBO Molecular Medicine, 2009, 1: 315-322.
Qu, "Clinical analysis of 26 cases of ovarian cancer treated with bevacizumab," China Health Care & Nutrition, Dec. 2014, No. 4 (II): 1882 (with English translation).
Sameni et al., "Cabozantinib (XL184) inhibits growth and invasion of preclinical TNBC models," Clinical Cancer Research, Oct. 2015, 22(4): 923-934.
Sulea et al., "Application of Assisted Design of Antibody and Protein Therapeutics (ADAPT) improves efficacy of a Clostridium difficile toxin A single-domain antibody," Scientific Reports, 2018, 8(260):1-11.
U.S. Food and Drug Administration, "ZEJULA (niraparib) capsules: Highlights of Prescribing Information," Mar. 2021, 37 pages.
Vajda et al., "Progress toward improved understanding of antibody maturation," Current Opinion in Structural Biology, 2021, 67: 226-231.
Vergote et al., "A phase 2 randomised discontinuation trial of cabozantinib in patients with ovarian carcinoma," European Journal of Cancer, 2017, 83: 229-236.
Wilcoxen et al., "Homologous recombination deficiency (HRD) score enriches for niraparib sensitive high grade ovarian tumors.," Presented at ASCO, 2015, Abstract #5532, 1 page.
Zhao et al., "A case of triple-negative breast cancer treated with bevacizumab," Journal of Practical Oncology, Jun. 2009, 24(3): 291-292 (with English translation).
American Cancer Society, Cancer Facts & Figures, 2018, 76 pages.
Anderson et ai "TIM-3 in autoimmunity." Current Opinion in Immunology. Dec. 2006, 18:65-669.

(56) References Cited

OTHER PUBLICATIONS

Anderson, "Tim-3, a negative regulator of anti-tumor immunity," Current Opinion in Immunology, Apr. 2012, 24(2):213-216.
Ayers et al., "IFN-γ-related mRNA profile predicts clinical response to PD-1 blockade," J. Clin. Invest., 2017, 127(8):2930-2940.
Bohnsack et al., "Adaptation of the immune-related response criteria: iRecist," ESMO, 2014, Abstract 4958.
Brown et al., "Combining DNA damaging therapeutics with immunotherapy: more haste, less speed", British Journal of Cancer, Nov. 9, 2017, 118 (3):312-324.
Chiba et al., "Tumor-infiltrating DCs suppress nucleic acid-mediated innate immune responses through interactions between the receptor TIM-3 and the alarmin HMGB1." Nature Immunology, Jul. 2012, 13:832-842.
ClinicalTrials.gov [online], "A Phase I/II Study of MEDI4736 in Combination With Olaparib in Patients With Advanced Solid Tumors. (Mediola)," U.S. National Library of Medicine, Apr. 12, 2016, retrieved on Jul. 6, 2022, retrieved from URL<https://clinicaltrials.gov/ct2/show/NCT02734004>, 17 pages.
ClinicalTrials.gov [online], "A Study of Niraparib Combined With Bevacizumab Maintenance Treatment in Participants With Advanced Ovarian Cancer Following Response on Front-Line Platinum-Based Chemotherapy," U.S. National Library of Medicine. Oct. 31, 2017. retrieved on Mar. 18, 2022, retrieved from URL <https://clinicaltrials.gov/ct2/show/NCT03326193>, 13 pages.
ClinicalTrials.gov [online], "Niraparib in Combination With Cabozantinib (XL184) in Patients With Advanced Urothelial Cancer (Nicaragua) (Nicaragua)," U.S. National Library of Medicine. Feb. 7, 2018, retrieved on Mar. 18, 2022, retrieved from URL <https://clinicaltrials.gov/ct2/show/NCT03425201>, 12 pages.
ClinicalTrials.gov [online], "Niraparib Versus Niraparib-bevacizumab Combination in Women With Platinum-sensitive Epithelial Ovarian Cancer (Avanova)," U.S. National Library of Medicine, Feb. 3, 2015, retrieved on Mar. 18, 2022, retrieved from URL <https://clinicaltrials.gov/ct2/show/NCT02354131>, 10 pages.
ClinicalTrials.gov [online], "Platine, Avastin and OLAparib in 1st Line (PAOLA-1)," U.S. National Library of Medicine, Jun. 23, 2015, retrieved on Mar. 18, 2022, retrieved from URL <https://www.clinicaltrials.gov/ct2/show/NCT02477644>, 11 pages.
Clinicaltrials.Gov, (2016). "NCT02657889: Niraparib in Combination With Pembrolizumab in Patients With Triple-negative Breast Cancer or Ovarian Cancer," Available online at <https://clinicaltrials.gov/ct2/show/NCT02657889>. 8 pages.
DeKruyff et al., "T Cell/Transmembrane, Ig, and Mucin-3 Allelic Variants Differentially Recognize Phosphatidylserine and Mediate Phagocytosis of Apoptotic Cells," The Journal of Immunology, Feb. 2010, 184(4): 1918-1930.
Extended European Search Report and Written Opinion dated Feb. 11, 2021, for EP Patent Application No. 18797986.9, 16 pages.
Hamanishi et al., "Immune Checkpoint Inhibition in Ovarian Cancer," International Immunology, Apr. 7, 2016, 28(7): 339-348.
Hamanishi et al., "PD1/PDL1 Blockade in Cancer Treatment: Perspectives and Issues," Int. J. Clin. Oncol., Feb. 22, 2016, 21: 462-473.
Han et al., "Tim-3: an activation marker and activation limiter of innate immune cells," Frontiers in Immunology. Dec. 2013, 4(449):1-7.
Hastings et al., "TIM-3 is Expressed on Activated Human CD4+ T Cells and Regulates Th1 and Th17 Cytokines," European Journal of Immunol., Oct. 2009, 39(9):2492-2501.
Huang et al., "CEACAM1 regulates TIM-3-mediated tolerance and exhaustion," Nature, 2014, 517(7534):386-390.
Isnansetyo et al., "Cytotoxicity of Fucoidan from Three Tropical Brown Algae Against Breast and Colon Cancer Cell Lines," Pharmacogn J., 2017, 9(1):14-20.
Kane, "TIM Proteins and Immunity'," Journal of Immunology, Mar. 2010, 184(6):2743-2749.
Killmurray, "Niraparib/Bevacizumab Combo Continues to Show Prolonged PFS in Patients With Advanced Ovarian Cancer," Targeted Oncology, Mar. 20, 2021, retrieved on Mar. 18, 2022, retrieved from URL <https://www.targetedonc.com/view/niraparib-bevacizumab-combo-continues-to-show-prolonged-pfs-in-patients-with-advanced-ovarian-cancer>, 3 pages.
Kuo et al., "Casaarinin from the Bark of Tenninalia arjuna Induces Apoptosis and Cell Cycle Arrest in Human Breast Adenocarcinoma MCF-7 Cells," Planta Med., 2005, 71(3):237-243.
Liberal et al., "The Impaired Immune Regulation of Autoimmune Hepatitis Is Linked to a Defective Galectin-9/Tim-3 Pathway", Hepatology, 2012, 56(2): 677-686.
Liu et al., What is the Place of PARP Inhibitors in Ovarian Cancer Treatment?, Curr Oncol Rep, 2016, 18:29, 9 pages.
Mantovani et al., "The chemokine system in cancer biology and therapy," Science Direct, Feb. 2010, 21(1):27-39.
Miller et al., "The status of poly(adenosine dipbospbaie-ribose) polymerase (PARP) inhibitors in ovarian cancer, part 2: extending the scope beyond olaparib and BRCA1/2 mutations," Clinical Advances in Hematology & Oncology, 2016, 14(9):704-711.
Mirza et al., "Niraparib plus bevacizumab versus niraparib alone for platinum-sensitive recurrent ovarian cancer (NSGO-AVANOVA2/ENGOT-ov24): a randomized, phase 2, superiority trial," Lancet Oncology, Aug. 29, 2019, pp. 1-11.
Monney et al., "Th1-specific cell surface protein Tim-3 regulates macrophage activation and severity of an autoimmune disease", Nature, Jan. 2002, 415:536-541.
Morales el al., "Review of poly (ADP-ribose) polymerase (PARP) mechanisms of action and rationale for targeting in cancer and other diseases," Crit. Rev. Eukaryot., 2014, Gene Expr. 24, 15-28.
Morris et al., "A Comprehensive Clinical Guide" Cancer, 2005, Chapter 6, pp. 41-44.
Nakayama et al., "Tim-3 mediates phagocytosis of apoptotic cells and cross-presentation," Blood, Apr. 2009, 113(16):3821-3830.
PCT International Search Report and Written Opinion in International Appln. No. PCT/US2018/031876, dated Aug. 6, 2018, 14 pages.
Richter et al., "On the role of the inhibitory receptor LAG-3 in acute and chronic LCMV infection," International Immunology, Oct. 2009, 22(1):13-23.
Saktiishi et al., "Emerging Tim-3 functions in anti-microbial and tumor immunity," Trends in Immunology. Aug. 2011, 32(8):345-349.
Schmid et al., "New perspectives in ovarian cancer treatment," Maturitas, Feb. 2014, 77(2):128-136.
Sternberg, "Niraparib-Bevacizumab Combo Improves Clinical Outcomes in Recurrent Ovarian Cancer," Cancer Network, Jun. 5, 2020, retrieved on Mar. 18, 2022, retrieved from URL <https://www.cancernetwork.com/view/niraparib-bevacizumab-combo-improves-clinical-outcomes-recurrent-ovarian-cancer>, 2 pages.
Stolze et al., "Comparative analysis of KRAS codon 12, 13, 18, 61 and 117 mutations using human MCF10A isogenic cell lines," Science Reports. Feb. 23, 2015, 9 pages.
Vela et al., "Chemokine receptor-specific antibodies in cancer immunotherapy: achievements and challenges," Frontiers in Immanology, Jan. 30, 2015, 6(12):1-15.
Wu et al., "Blockade of Tim-3 signaling restores the virus-specific CD8$^+$T-cell response in patients with chronic hepatitis B," European Journal of Immunology, 2012, 42(5):1180-1191.
Yehia et al., "The Clinical Spectrum of PTEN Mutations," Annu. Rev. Med., Jan. 27, 2020, 71:103-16.
Zhu et al., "The Tim-3 ligand galectin-9 negatively regulates T helper type 1 immunity," Nature Immunology; 2005, 6:1245-1252.
Clinicaltrials.gov [online], "Phase I/II Study of the Anti-Programmed Death Ligand-1 Durvalumab Antibody (MEDI4736) in Combination With Olaparib and/or Cediranib for Advanced Solid Tumors and Advanced or Recurrent Ovarian, Triple Negative Breast, Lung, Prostate and Colorectal Cancer," NCT02484404, last updated on Nov. 1, 2022, retrieved on Nov. 9, 2022, retrieved from URL<https://www.clinicaltrials.gov/ct2/show/NCT02484404>, 15 pages.
Mirza et al., "Abstract: A phase I study of bevacizumab in combination with niraparib in patients with platinum-sensitive epithelial ovarian cancer: The ENGOT-OV24/AVANOVA1 trial," Journal of Clinical Oncology', May 20, 2016, 34(15 Suppl):5555.

(56) References Cited

OTHER PUBLICATIONS

Robillard et al., "Abstract 3650: Preclinical evaluation of the PARP inhibitor rucaparib in combination with PD-1 and PD-L1 inhibition in a syngeneic BRCA1 mutant ovarian cancer model," Cancer Research, Jul. 1, 2017, 77(13_Supplement):3650.

COMBINATION THERAPIES FOR TREATING CANCER

CROSS-REFERENCE TO RELATED APPLICATIONS

The present application is a 35 U.S.C. § 371 National Stage Application of International Application No. PCT/US18/33437, filed May 18, 2018, which claims benefit of U.S. Provisional Application No. 62/508,363, filed May 18, 2017; U.S. Provisional Application No. 62/508,481, filed May 19, 2017; and U.S. Provisional Application No. 62/578,204, filed Oct. 27, 2017, each of which is hereby incorporated by reference in its entirety.

BACKGROUND

Cancer is a serious public health problem, with about 595,690 people in the United States of America expected to die of cancer in 2016 alone according to the American Cancer Society, Cancer Facts & Figures 2016 (http://www.cancer.org/acs/groups/content/@research/documents/document/acspc-047079.pdf).

SUMMARY

Provided herein are methods of treating a subject with a disease or condition comprising administering to the subject (a) a first agent that inhibits poly [ADP-ribose] polymerase (PARP); and (b) a second agent, wherein the second agent comprises a regulatory T cell (Treg) inhibitory agent, a macrophage inhibitory agent, an antigen specific immune response enhancer agent, or a combination thereof.

Provided herein are methods of enhancing an immune response or increasing the activity of an immune cell in a subject with a disease or condition comprising administering to the subject (a) a first agent that inhibits poly [ADP-ribose] polymerase (PARP); and (b) a second agent, wherein the second agent comprises a regulatory T cell (Treg) inhibitory agent, a macrophage inhibitory agent, an antigen specific immune response enhancer agent, or a combination thereof. In embodiments, the method enhances an anti-tumor response in the subject.

Provided herein are methods of inducing an immune response in a subject with a disease or condition comprising administering to the subject (a) a first agent that inhibits poly [ADP-ribose] polymerase (PARP); and (b) a second agent, wherein the second agent comprises a regulatory T cell (Treg) inhibitory agent, a macrophage inhibitory agent, an antigen specific immune response enhancer agent, or a combination thereof. In embodiments, the method induces an anti-tumor response in the subject.

In some embodiments, the first agent inhibits PARP 1 and/or 2. In some embodiments, a first agent that inhibits PARP 1 and/or 2 is selected from the group consisting of: ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof. In some embodiments, the first agent is a small organic or inorganic molecule; a saccharine; an oligosaccharide; a polysaccharide; a carbohydrate; a peptide; a protein; a peptide analog; a peptide derivative; a lipid; an antibody; an antibody fragment; a peptidomimetic; a nucleic acid; a nucleic acid analog; a nucleic acid derivative; an extract made from biological materials; a naturally occurring or synthetic composition; a metal; a toxin; or any combination thereof. In some embodiments, the first agent is a small molecule.

In some cases, the first agent is selected from the group consisting of: niraparib, olaparib, rucaparib, talazoparib, and veliparib, or salts or derivatives thereof. In some cases, the first agent comprises niraparib or a pharmaceutically acceptable salt or derivative thereof. In some instances the Treg inhibitory agent inhibits or decreases the activity, function, or migration of a Treg cell. In some cases, the Treg inhibitory agent decreases a population of Treg cells in the subject. In some embodiments, the Treg inhibitory agent substantially ablates or eliminates a population of Treg cells in the subject. In some embodiments, the macrophage inhibitory agent inhibits or decreases the activity, function, or migration of a macrophage. In some embodiments, the macrophage inhibitory agent decreases a population of macrophage cells in the subject. In some embodiments, the macrophage inhibitory agent substantially ablates or eliminates a population of macrophage cells in the subject. In some embodiments, the Treg cell is an infiltrating T cell.

In some embodiments, the macrophage comprises a tumor-associated macrophage (TAM). In some embodiments, the second agent enhances an antigen specific CD4$^+$ T cell activity. In some embodiments, the second agent enhances an antigen specific CD8$^+$ T cell activity. In some embodiments, the second agent is selected from the group consisting of a small organic or inorganic molecule; a saccharine; an oligosaccharide; a polysaccharide; a carbohydrate; a peptide; a protein; a peptide analog; a peptide derivative; a lipid; an antibody; an antibody fragment; a peptidomimetic; a nucleic acid; a nucleic acid analog; a nucleic acid derivative; an extract made from biological materials; a naturally occurring or synthetic composition; a metal; a toxin; and any combination thereof.

In some embodiments, the administering comprises administering the first and second agent sequentially. In some embodiments, the administering comprises administering the first and second agent simultaneously. In some embodiments, the administering comprises administering the first agent before administering the second agent second agent. In some embodiments, the subject is a mammalian subject. In some embodiments, the subject is a human. In some embodiments, the second agent is a regulatory T cell (Treg) inhibitory agent selected from the group consisting of a Treg ablating agent, a Treg migration inhibitor agent, a Treg function inhibitor agent, and combinations thereof. In some embodiments, the Treg ablating agent is selected from the group consisting of cyclophosphamide, paclitaxel, imatinib, sunitinib, sorafenib, dasatinib, temozolomide, daclizumab, denileukin diftitox, and combinations thereof. In some embodiments, the Treg migration inhibitor agent is selected from the group consisting of AMD3100, mogamulizumab, casuarinin, fucoidan, and combinations thereof. In some embodiments, the Treg function inhibitor agent is selected from the group consisting of an anti-CTLA4 agent (e.g., ipilimumab, tremelimumab), an anti-OX40 agent, an anti-GITR agent, an adenosine receptor antagonist (e.g., caffeine, theophylline, theobromine, and 8-phenylxanthines), P60, and combinations thereof.

In some embodiments, the second agent is a macrophage inhibitory agent selected from the group consisting of a macrophage recruitment inhibitory agent, an M2 macrophage antisurvival agent, an M1 macrophage enhancing agent, an M2 to M1 polarizing agent, a macrophage activity inhibitor agent and combinations thereof. In some embodiments, the macrophage recruitment inhibitory agent is selected from the group consisting of an anti-CCL2/CCR2 agent, an anti-IL6 agent, an anti-M-CSFR agent, and combinations thereof. In some embodiments, a macrophage recruitment inhibitory agent is an anti-M-CSFR agent. In some embodiments, the macrophage recruitment inhibitory agent is selected from the group consisting of trabectedin, RS102895, PF-04136309, CNT0888, MLN1202, siltuximab, JNJ-28312141, GW2580, IMC-CS4 (LY3022855), emactuzumab, AMG820, pexidartinib, linifanib, OSI-930, CEP-32496, PLX7846, ARRY-382, JNJ-40346527, MCS110, PLX3397, PLX6134, PD-0360324, FPA008, and combinations thereof. In some embodiments, a macrophage recruitment inhibitory agent is BLZ945, PLX7846, GW2580, ARRY-382, JNJ-40346527, emactuzumab, pexidartinib, AMG820, IMC-CS4 (LY3022855), MCS110, PLX3397, PLX6134, PD-0360324, or FPA008. In some embodiments, a macrophage recruitment inhibitory agent is BLZ945. In some embodiments, the M2 macrophage antisurvival agent is selected from the group consisting of an MMP inhibitor, clodronate, zoledronic acid, dichloromethylene bisphosphonate, trabectedin, dasatinib, retinoic acid, attenuated bacteria (e.g., *Shigella flexneri, Salmonella typhimurium, Listeria monocytogens, Chlamydia psittaci, Legionella pneumophila*), and combinations thereof.

In some embodiments, the M1 macrophage enhancing agent or the M2 to M1 polarizing agent is selected from the group consisting of an anti-CD40 agent, an anti-IL-10R agent, a CD47 antagonist (e.g., Hu5F9-G4, CC-90002, and CD47-Fc fusion protein TTI-621), PolyI:C, LPS, monophosphoryl A, imiquimod, R-848, CpG-ODN, IFN-α, IFN-β, IFN-γ, GM-CSF, IL-12, IL-2, IL-15, Tα1, ibrutinib, EF-022 and combinations thereof. In some embodiments, the macrophage activity inhibitory agent is selected from the group consisting of a STAT3 inhibitor, a STAT6 inhibitor, or an anti-tumor drug agent. In some embodiments, the macrophage activity inhibitory agent is selected from the group consisting of WP1066, sunitinib, sorafenib, STA-21, IS3 295, S31-M2001, AS1517499, leflunomide, TMC-264, histidine-rich glycoprotein (HRG), copper chelate (CuNG), 5,6-dimethylxanthenone-4-acetic acid (MDXAA), vadimezan (ASA404), cisplatin, silibinin, proton pump inhibitor pantoprazole (PPZ), CNI-1493 and combinations thereof. In some embodiments, the macrophage inhibitor agent is an anti-IL-la agent (e.g., xilonix).

In some embodiments, the second agent is an antigen specific immune response enhancer agent selected from the group consisting of an anti-PD-1 agent, an anti-PD-L1 agent, a GITR (glucocorticoid-induced TNFR-related protein) stimulating agent, an anti-CTLA4 agent, an anti-TIM-3 agent, an anti-LAG-3 agent, an agent that enhances tumor antigen presentation (e.g., personalized cancer vaccine, autologous antigen presenting cell, autologous dendritic cells, artificial antigen presenting cell), a chemokine signaling agent, an anti-VEGF agent, a cytokine signal stimulating agent, and combinations thereof. In some embodiments, the anti-PD-1 agent is selected from the group consisting of pembrolizumab, nivolumab, PDR001, REGN2810 (SAR-439684), BGB-A317, BI 754091, IBI308, INCSHR-1210, JNJ-63723283, JS-001, MEDI0680 (AMP-514), MGA-012, PF-06801591, REGN-2810, TSR-042, PDR-001, camrelizumab (HR-301210), BCD-100, AGEN-2034, CS1001, Sym-021, LZMO09, KN-035, AB122, genolimzumab (CBT-501), AK 104, GLS-010, and combinations thereof. In some embodiments, the anti-PD-L1 agent is selected from the group consisting of atezolizumab, durvalumab, avelumab, LY3300054, BGB-A333, SHR-1316, CK-301, and combinations thereof. In some embodiments, the GITR stimulating agent is selected from the group consisting of DTA-1, mGITRL, pGITRL, and combinations thereof. In some embodiments, the anti-CTLA4 agent is selected from the group consisting of ipilimumab, tremelimumab, and combinations thereof. In some embodiments, the chemokine signaling agent is selected from the group consisting of CXCL16, a CXCR6 chemokine receptor (CD186) agonist, and combinations thereof. In some embodiments, the anti-VEGF agent is selected from the group consisting of bevacizumab, pazopanib, sunitinib, sorafenib, axitinib, ponatinib, regorafenib, cabozantinib, vandetanib, ramucirumab, lenvatinib, ziv-aflibercept, and combinations thereof. In some embodiments, the cytokine signal stimulating agent is an interleukin or an interferon. In some embodiments, the interleukin is selected from the group consisting of IL-2, IL-1, IL-7, IL-15, IL-12, IL-18, and combinations thereof. In some embodiments, the interferon is IFN alpha.

In some embodiments, the second agent is an antigen specific immune response enhancer agent selected from the group consisting of a flavonoid (e.g., flavonoid glycoside), lidocaine, lamotrigine, sulfamethoxazole, phenytoin, carbamazepine, sulfamethoxazole, phenytoin, allopurinol, paracetamol, mepivacaine, p-phenylenediamine, ciprofloxacin and moxifloxacin. In some embodiments, the disease or condition is cancer. In some embodiments, the cancer is selected from the group consisting of ovarian cancer, breast cancer, cervical cancer, endometrial cancer, prostate cancer, testicular cancer, pancreatic cancer, esophageal cancer, head and neck cancer, gastric cancer, bladder cancer, lung cancer, bone cancer, colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma, bladder cancer, liver cancer, kidney cancer, myeloma, lymphoma, and combinations thereof.

In some embodiments, the administering comprises administering a composition comprising a capsule comprising the first agent. In some embodiments, the capsule comprises a formulation comprising the first agent and one or more pharmaceutically acceptable excipients. In some embodiments, the one or more pharmaceutically acceptable excipients comprises lactose monohydrate, magnesium stearate, or a combination thereof. In some embodiments, a therapeutically effective amount of the first or second agent is administered. In some embodiments, the method further comprises administering a third agent to the subject. In some embodiments, the third agent comprises an antigen specific immune response enhancer agent, an anti-angiogenic agent, a chemotherapeutic agent, or combinations thereof. In some embodiments, the antigen specific immune response enhancer agent comprises an anti-PD-1 agent, an anti-PD-L1 agent, an anti-CTLA4 agent, an anti-TIM-3 agent, or an anti-LAG-3 agent. In some embodiments, the anti-angiogenic agent is selected from the group consisting of TNP-470, platelet factor 4, thrombospondin-1, tissue inhibitors of metalloproteases (TIMP1 and TIMP2), prolactin, angiostatin, endostatin, bFGF soluble receptor, transforming growth factor beta, interferon alpha, soluble KDR and FLT-1 receptors, placental proliferin-related protein, and combinations thereof.

In some embodiments, the chemotherapeutic agent is selected from the group consisting of aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, vinorelbine, and combinations thereof.

Provided herein are pharmaceutical compositions comprising (a) a first agent that inhibits poly [ADP-ribose] polymerase (PARP); and (b) a second agent, wherein the second agent comprises a regulatory T cell (Treg) inhibitory agent, a macrophage inhibitory agent, an antigen specific immune response enhancer agent, or a combination thereof.

In some embodiments, the first agent is an agent that inhibits PARP 1 and/or 2. In some embodiments, a first agent that inhibits PARP 1 and/or 2 is selected from the group consisting of: ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof. In some embodiments, the first agent is a small organic or inorganic molecule; a saccharine; an oligosaccharide; a polysaccharide; a carbohydrate; a peptide; a protein; a peptide analog; a peptide derivative; a lipid; an antibody; an antibody fragment; a peptidomimetic; a nucleic acid; a nucleic acid analog; a nucleic acid derivative; an extract made from biological materials; a naturally occurring or synthetic composition; a metal; a toxin; or any combination thereof. In some embodiments, the first agent is a small molecule. In some cases, the first agent is selected from the group consisting of: niraparib, olaparib, rucaparib, talazoparib, and veliparib, or salts or derivatives thereof. In some cases, the first agent comprises niraparib or a pharmaceutically acceptable salt or derivative thereof.

In some instances the Treg inhibitory agent inhibits or decreases the activity, function, or migration of a Treg cell. In some cases, the Treg inhibitory agent decreases a population of Treg cells in the subject. In some embodiments, the Treg inhibitory agent substantially ablates or eliminates a population of Treg cells in the subject. In some embodiments, the macrophage inhibitory agent inhibits or decreases the activity, function, or migration of a macrophage. In some embodiments, the macrophage inhibitory agent decreases a population of macrophage cells in the subject. In some embodiments, the macrophage inhibitory agent substantially ablates or eliminates a population of macrophage cells in the subject. In some embodiments, the Treg cell is an infiltrating T cell.

In some embodiments, the macrophage comprises a tumor-associated macrophage (TAM). In some embodiments, the second agent enhances an antigen specific $CD4^+$ T cell activity. In some embodiments, the second agent enhances an antigen specific $CD8^+$ T cell activity. In some embodiments, the second agent is selected from the group consisting of a small organic or inorganic molecule; a saccharine; an oligosaccharide; a polysaccharide; a carbohydrate; a peptide; a protein; a peptide analog; a peptide derivative; a lipid; an antibody; an antibody fragment; a peptidomimetic; a nucleic acid; a nucleic acid analog; a nucleic acid derivative; an extract made from biological materials; a naturally occurring or synthetic composition; a metal; a toxin; and any combination thereof.

In some embodiments, the pharmaceutical composition is administered to a subject and the administering comprises administering the first and second agent sequentially. In some embodiments, the administering comprises administering the first and second agent simultaneously. In some embodiments, the administering comprises administering the first agent before administering the second agent second agent. In some embodiments, the subject is a mammalian subject. In some embodiments, the subject is a human. In some embodiments, the second agent is a regulatory T cell (Treg) inhibitory agent selected from the group consisting of a Treg ablating agent, a Treg migration inhibitor agent, a Treg function inhibitor agent, and combinations thereof. In some embodiments, the Treg ablating agent is selected from the group consisting of cyclophosphamide, paclitaxel, imatinib, sunitinib, sorafenib, dasatinib, temozolomide, daclizumab, denileukin diftitox, and combinations thereof. In some embodiments, the Treg migration inhibitor agent is selected from the group consisting of AMD3100, mogamulizumab, casuarinin, fucoidan, and combinations thereof. In some embodiments, the Treg function inhibitor agent is selected from the group consisting of an anti-CTLA4 agent (e.g., ipilimumab, tremelimumab), an anti-OX40 agent, an anti-GITR agent, an adenosine receptor antagonist (e.g., caffeine, theophylline, theobromine, and 8-phenylxanthines), P60, and combinations thereof.

In some embodiments, the second agent is a macrophage inhibitory agent selected from the group consisting of a macrophage recruitment inhibitory agent, an M2 macrophage antisurvival agent, an M1 macrophage enhancing agent, an M2 to M1 polarizing agent, a macrophage activity inhibitor agent and combinations thereof. In some embodiments, the macrophage recruitment inhibitory agent is selected from the group consisting of an anti-CCL2/CCR2 agent, an anti-IL6 agent, an anti-M-CSFR agent, and combinations thereof. In some embodiments, a macrophage recruitment inhibitory agent is an anti-M-CSFR agent. In some embodiments, the macrophage recruitment inhibitory agent is selected from the group consisting of trabectedin, RS102895, PF-04136309, CNT0888, MLN1202, siltuximab, JNJ-28312141, GW2580, IMC-CS4 (LY3022855), emactuzumab, AMG820, pexidartinib, linifanib, OSI-930, CEP-32496, PLX7846, ARRY-382, JNJ-40346527, MCS110, PLX3397, PLX6134, PD-0360324, FPA008, and combinations thereof. In some embodiments, a macrophage recruitment inhibitory agent is BLZ945, PLX7846, GW2580, ARRY-382, JNJ-40346527, emactuzumab, pexidartinib, AMG820, IMC-CS4 (LY3022855), MCS110, PLX3397, PLX6134, PD-0360324, or FPA008. In some embodiments, a macrophage recruitment inhibitory agent is BLZ945. In some embodiments, the M2 macrophage anti-survival agent is selected from the group consisting of an MMP inhibitor, clodronate, zoledronic acid, dichloromethylene bisphosphonate, trabectedin, dasatinib, retinoic acid, attenuated bacteria (e.g., *Shigella flexneri, Salmonella typhimurium, Listeria monocytogens, Chlamydia psittaci, Legionella pneumophila*), and combinations thereof.

In some embodiments, the M1 macrophage enhancing agent or the M2 to M1 polarizing agent is selected from the group consisting of an anti-CD40 agent, an anti-IL-10R agent, a CD47 antagonist (e.g., Hu5F9-G4, CC-90002, and CD47-Fc fusion protein TTI-621), PolyI:C, LPS, monophosphoryl A, imiquimod, R-848, CpG-ODN, IFN-α, IFN-0, IFN-γ, GM-CSF, IL-12, IL-2, IL-15, Tα1, ibrutinib, EF-022 and combinations thereof. In some embodiments, the macrophage activity inhibitory agent is selected from the group consisting of a STAT3 inhibitor, a STAT6 inhibitor, or an anti-tumor drug agent. In some embodiments, the macrophage activity inhibitory agent is selected from the group consisting of WP1066, sunitinib, sorafenib, STA-21, IS3 295, S31-M2001, AS1517499, leflunomide, TMC-264, histidine-rich glycoprotein (HRG), copper chelate (CuNG), 5,6-dimethylxanthenone-4-acetic acid (MDXAA), vadimezan (ASA404), cisplatin, silibinin, proton pump inhibitor pantoprazole (PPZ), CNI-1493 and combinations thereof. In some embodiments, the macrophage inhibitor agent is an anti-IL-la agent (e.g., xilonix).

In some embodiments, the second agent is an antigen specific immune response enhancer agent selected from the group consisting of an anti-PD-1 agent, an anti-PD-L1 agent, a GITR (glucocorticoid-induced TNFR-related protein) stimulating agent, an anti-CTLA4 agent, an anti-TIM-3 agent, an anti-LAG-3 agent, an agent that enhances tumor antigen presentation (e.g., personalized cancer vaccine, autologous antigen presenting cell, autologous dendritic cells, artificial antigen presenting cell), a chemokine signaling agent, an anti-VEGF agent, a cytokine signal stimulating agent, and combinations thereof. In some embodiments, the anti-PD-1 agent is selected from the group consisting of pembrolizumab, nivolumab, PDR001, REGN2810 (SAR-439684), BGB-A317, BI 754091, IBI308, INCSHR-1210, JNJ-63723283, JS-001, MEDI0680 (AMP-514), MGA-012, PF-06801591, REGN-2810, TSR-042, PDR-001, camrelizumab (HR-301210), BCD-100, AGEN-2034, CS1001, Sym-021, LZMO09, KN-035, AB122, genolimzumab (CBT-501), AK 104, GLS-010, and combinations thereof. In some embodiments, the anti-PD-L1 agent is selected from the group consisting of atezolizumab, durvalumab, avelumab, LY3300054, BGB-A333, SHR-1316, CK-301, and combinations thereof. In some embodiments, the GITR stimulating agent is selected from the group consisting of DTA-1, mGITRL, pGITRL, and combinations thereof. In some embodiments, the anti-CTLA4 agent is selected from the group consisting of ipilimumab, tremelimumab, and combinations thereof. In some embodiments, the chemokine signaling agent is selected from the group consisting of CXCL16, a CXCR6 chemokine receptor (CD186) agonist, and combinations thereof. In some embodiments, the anti-VEGF agent is selected from the group consisting of bevacizumab, pazopanib, sunitinib, sorafenib, axitinib, ponatinib, regorafenib, cabozantinib, vandetanib, ramucirumab, lenvatinib, ziv-aflibercept, and combinations thereof. In some embodiments, the cytokine signal stimulating agent is an interleukin or an interferon. In some embodiments, the interleukin is selected from the group consisting of IL-2, IL-1, IL-7, IL-15, IL-12, IL-18 and combinations thereof. In some embodiments, the interferon is IFN alpha.

In some embodiments, the second agent is an antigen specific immune response enhancer agent selected from the group consisting of a flavonoid (e.g., flavonoid glycoside), lidocaine, lamotrigine, sulfamethoxazole, phenytoin, carbamazepine, sulfamethoxazole, phenytoin, allopurinol, paracetamol, mepivacaine, p-phenylenediamine, ciprofloxacin and moxifloxacin.

In some embodiments, the disease or condition is cancer. In some embodiments, the cancer is selected from the group consisting of ovarian cancer, breast cancer, cervical cancer, endometrial cancer, prostate cancer, testicular cancer, pancreatic cancer, esophageal cancer, head and neck cancer, gastric cancer, bladder cancer, lung cancer, bone cancer, colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma, bladder cancer, liver cancer, kidney cancer, myeloma, lymphoma, and combinations thereof.

In some embodiments, the pharmaceutical composition is administered to a subject and the administering comprises administering a composition comprising a capsule comprising the first agent. In some embodiments, the capsule comprises a formulation comprising the first agent and one or more pharmaceutically acceptable excipients. In some embodiments, the one or more pharmaceutically acceptable excipients comprises lactose monohydrate, magnesium stearate, or a combination thereof. In some embodiments, a therapeutically effective amount of the first or second agent is administered. In some embodiments, the method further comprises administering a third agent to the subject. In some embodiments, the third agent comprises an antigen specific immune response enhancer agent, an anti-angiogenic agent, a chemotherapeutic agent, or combinations thereof. In some embodiments, the antigen specific immune response enhancer agent comprises an anti-PD-1 agent, an anti-PD-L1 agent, an anti-CTLA4 agent, an anti-TIM-3 agent, or an anti-LAG-3 agent. In some embodiments, the anti-angiogenic agent is selected from the group consisting of TNP-470, platelet factor 4, thrombospondin-1, tissue inhibitors of metalloproteases (TIMP1 and TIMP2), prolactin, angiostatin, endostatin, bFGF soluble receptor, transforming growth factor beta, interferon alpha, soluble KDR and FLT-1 receptors, placental proliferin-related protein, and combinations thereof.

In some embodiments, the chemotherapeutic agent is selected from the group consisting of aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, vinorelbine, and combinations thereof.

The present disclosure encompasses the recognition that a combination therapy with an agent that regulates activity within the tumor microenvironment (e.g., activity of T cells and/or the infiltration of T cells into the tumor environment) and an agent that inhibits PARP is useful for treating certain cancers.

In some embodiments, a PARP inhibitor increases infiltration of T cells in the tumor microenvironment. In some embodiments, a PARP inhibitor increases infiltration of $CD4^+$ T cells in the tumor microenvironment. In some embodiments, a PARP inhibitor increases infiltration of $CD8^+$ T cells in the tumor microenvironment. In some embodiments, a PARP inhibitor increases infiltration of $CD4^+$ and $CD8^+$ T cells in the tumor microenvironment. In some embodiments, a PARP inhibitor increases infiltration of macrophages in the tumor microenvironment. In some embodiments, a PARP inhibitor increases infiltration of Treg cells into the tumor microenvironment.

In some embodiments, agents that inhibit PARP include agents that inhibit PARP-1 and/or PARP-2. In some embodiments, agents that inhibit PARP include ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof. In some embodiments, agents that inhibit PARP are combinations of two or more agents selected from ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof. In some embodiments, an agent that inhibits part is or comprises niraparib, olaparib, rucaparib, talazoparib, veliparib, or any combination thereof. In some certain embodiments, an agent that inhibits PARP is niraparib ((3S)-3-[4-{7-(aminocarbonyl)-2H-indazol-2-yl}phenyl]piperidine), an orally active PARP inhibitor.

In some certain embodiments, an agent that regulates T cell activity is administered to a patient who is receiving, has received or will receive treatment with niraparib. In some certain embodiments, niraparib is administered to patient who is receiving, has received or will receive treatment with an agent that regulates T cell activity.

In some embodiments, cancers for treatment with a combination therapy of the present disclosure include melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, esophageal cancer, squamous cell carcinoma of the head and neck, ovarian cancer, prostate cancer, pancreatic cancer, or Merkel cell carcinoma.

In some embodiments, a cancer is a solid tumor. In some embodiments, a patient or population of patients has a hematological cancer.

In some embodiments, the method comprises administering one or both of a therapy that regulates T cell activity and a therapy that inhibits poly [ADP-ribose] polymerase (PARP) ("anti-PARP therapy") to a subject so that the subject receives treatment with both therapies. In some embodiments, an agent that regulates T cell activity is an agent that enhances activity of antigen-specific cells in a tumor microenvironment. In some embodiments, an agent that regulates T cell activity is an agent that enhances activity of $CD8^+$ T cells in tumor microenvironments. In some embodiments, an agent that regulates T cell activity is an agent that enhances activity of $CD4^+$ T cells in tumor microenvironments. In some embodiments, regulating activity of T cells (e.g., $CD4^+$ and/or $CD8^+$ T cells) in the tumor environment involves upregulating the anti-tumor activity of individual T cells, increasing a rate of proliferation of the T cells, or enhancing the recruitment of the T cells to the tumor microenvironment. In some embodiments, an agent that regulates. In some embodiments, an agent that enhances T cell activity is an agent that blocks macrophage recruitment. In some embodiments, an agent that regulates T cell activity is an agent that blocks recruitment of M2 macrophages. In some embodiments, an agent that regulates T cell activity is an agent that blocks Treg cell recruitment.

In some embodiments, an agent that regulates T cell activity is a small molecule, a nucleic acid, a polypeptide (e.g., an antibody), a carbohydrate, a lipid, a metal, a cell, a cell preparation, or a toxin. In some embodiments, an agent that regulates T cell activity is an antibody agent. Antibody agents can include any polypeptide or polypeptide complex that includes immunoglobulin structural elements sufficient to confer specific binding. Exemplary antibody agents include, but are not limited to, monoclonal antibodies, polyclonal antibodies, antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s.

In some embodiments, an anti-PARP therapy comprises administration of an agent that inhibits PARP. In some embodiments, an agent that inhibits PARP is a small molecule, a nucleic acid, a polypeptide (e.g., an antibody), a carbohydrate, a lipid, a metal, or a toxin. In some embodiments, an agent that inhibits PARP is a small molecule. In some embodiments, an agent that inhibits PARP is selected from the group consisting of: ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof. In some embodiments, an agent that inhibits PARP is selected from the group consisting of: niraparib, olaparib, rucaparib, talazoparib, and veliparib or salts or derivatives thereof. In some embodiments, an agent that inhibits PARP is niraparib or a salt or derivative thereof.

In some embodiments, an agent that regulates T cell activity is a small molecule, a nucleic acid, a polypeptide (e.g., an antibody), a carbohydrate, a lipid, a metal, a cell, a cell preparation, or a toxin. In some embodiments, an agent that regulates T cell activity is an anti-PD-1 antibody agent. In some embodiments, an agent that enhances T cell activity is an anti-PD-1 antibody selected from the group consisting of: BGB-A317, BI 754091, IBI308, INCSHR-1210, JNJ-63723283, JS-001, MEDI-0680, MGA-012, nivolumab, PDR001, pembrolizumab, PF-06801591, REGN-2810, TSR-042 and derivatives thereof. In some embodiments, an anti-PD-1 antibody is pembrolizumab or a derivative thereof.

DETAILED DESCRIPTION OF CERTAIN EMBODIMENTS

Definitions

Figure 1A:
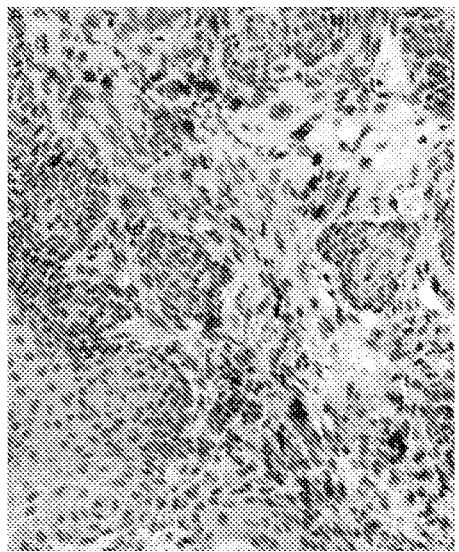
FIG. 1A depicts representative CD4 IHC staining on tumor samples developed from $Apc^{Min}$/J heterozygous background. upon vehicle or niraparib treatment.
Figure 1A:
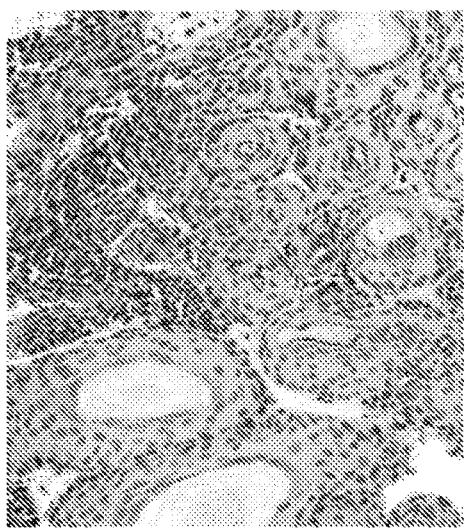

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

As used herein, the term "administration" typically refers to the administration of a composition to a subject or system. Those of ordinary skill in the art will be aware of a variety of routes that may, in appropriate circumstances, be utilized for administration to a subject, for example a human subject. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

As used herein, the terms "dosage form" or "unit dosage form" refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a regimen that has been determined to correlate with a desired or beneficial outcome when administered to a relevant population (e.g., with a therapeutic regimen). Those of ordinary skill in the art appreciate that the total amount of a therapeutic composition or agent administered to a particular subject is determined by one or more attending physicians and may involve administration of multiple dosage forms.

As used herein, the term "regimen" refers to a set of unit doses (typically more than one) that are administered individually to a subject, typically separated by one or more periods of time. In some embodiments, a given therapeutic agent is administered according to a regimen, which may involve one or more doses. In some embodiments, a regimen comprises a plurality of doses each of which is separated in time from other doses. In some embodiments, individual doses are separated from one another by a time period of the same length; in some embodiments, a regimen comprises a plurality of doses, wherein the doses are separated by time periods of different length. In some embodiments, a regimen comprises doses of the same amount. In some embodiments, a regimen comprises doses of different amounts. In some embodiments, a regimen comprises at least one dose, wherein the dose comprises one unit dose of the therapeutic agent. In some embodiments, a regimen comprises at least one dose, wherein the dose comprises two or more unit doses of the therapeutic agent.

As used herein, the term "patient", "subject", or "test subject" refers to any organism, including a human or non-human, to which provided compound or compounds described herein are administered in accordance with the present invention e.g., for experimental, diagnostic, prophylactic, and/or therapeutic purposes. Typical subjects include animals (e.g., mammals such as mice, rats, rabbits, canines, felines, horses, cattle, pigs, deer, non-human primates, and humans; insects; worms; birds; reptiles; amphibians; etc.). In embodiments, the subject is a human. In some embodiments, a subject may be suffering from, and/or susceptible to a disease, disorder, and/or condition (e.g., cancer). In some embodiments, a patient is a human that has been diagnosed with a cancer. In some embodiments, a patient is a human possessing one or more female reproductive organs.

The term "cancer" includes both solid tumors and hematological malignancies. Cancers include, but are not limited to, gynecological cancers, ovarian cancer, cancer of the fallopian tube(s), peritoneal cancer, breast cancer, cervical cancer, endometrial cancer, prostate cancer, testicular cancer, pancreatic cancer, esophageal cancer, head and neck cancer, gastric cancer, bladder cancer, lung cancer (e.g., adenocarcinoma, NSCLC and SCLC), bone cancer (e.g., osteosarcoma), colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma (e.g., liposarcoma), bladder cancer, liver cancer (e.g., hepatocellular carcinoma), kidney cancer (e.g., renal cell carcinoma), myeloid disorders (e.g., AML, CML, myelodysplastic syndrome and promyelocytic leukemia), and lymphoid disorders (e.g., leukemia, multiple myeloma, mantle cell lymphoma, ALL, CLL, B-cell lymphoma, T-cell lymphoma, Hodgkin's lymphoma, non-Hodgkin's lymphoma, hairy cell lymphoma). Cancers include, but are not limited to, ovarian cancer, breast cancer, cervical cancer, endometrial cancer, prostate cancer, testicular cancer, pancreatic cancer, esophageal cancer, head and neck cancer, gastric cancer, bladder cancer, lung cancer, bone cancer, colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma, bladder cancer, liver cancer, kidney cancer, myeloma, lymphoma, and combinations thereof.

The term "composition", as in pharmaceutical composition, is intended to encompass a drug product comprising niraparib or its pharmaceutically acceptable salts, esters, solvates, polymorphs, stereoisomers or mixtures thereof, as well as, in some embodiments, one or more additional pharmaceutically active ingredients in combination with the niraparib. The composition may also include one or more inert ingredient(s) (e.g., pharmaceutically acceptable excipients). Such pharmaceutical compositions are synonymous with "formulation" and "dosage form". Pharmaceutical composition of the invention include, but is not limited to, granules, tablets (single layered tablets, multilayered tablets, mini tablets, bioadhesive tablets, caplets, matrix tablets, tablet within a tablet, mucoadhesive tablets, modified release tablets, orally disintegrating tablets, pulsatile release tablets, timed release tablets, delayed release, controlled release, extended release and sustained release tablets), capsules (hard and soft or liquid filled soft gelatin capsules), pills, troches, sachets, powders, microcapsules, minitablets, tablets in capsules and microspheres, matrix composition and the like. In some embodiments, the pharmaceutical composition refers to capsules. In some embodiments, the pharmaceutical composition refers to hard gelatin capsules or HPMC based capsules. In some embodiments, the pharmaceutical composition refers to hard gelatin capsules.

"Diluents" increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like. Combinations of one or more diluents can also be used.

As used herein, the term "effective amount" or "therapeutically effective amount" refers to an amount of one or more therapeutic agents (e.g., niraparib in combination with one or more additional pharmaceutically active ingredients) that produces the desired effect for which it is administered. In some embodiments, the term refers to an amount that is sufficient, when administered to a population suffering from or susceptible to a disease, disorder, and/or condition in accordance with a regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a regimen.

The terms "enhance" or "enhancing" refers to an increase or prolongation of either the potency or duration of a desired effect of a composition described herein, or a diminution of any adverse symptomatology that is consequent upon the administration of the therapeutic agent or agents. Thus, in regard to enhancing the effect of niraparib disclosed herein, the term "enhancing" refers to the ability to increase or prolong, either in potency or duration, the effect of other therapeutic agents that are used in combination with niraparib disclosed herein. An "enhancing-effective amount," as used herein, refers to an amount of niraparib or other therapeutic agent which is adequate to enhance the effect of another therapeutic agent or niraparib in a desired system. When used in a patient, amounts effective for this use will depend on the severity and course of the disease, disorder or condition, previous therapy, the patient's health status and response to the drugs, and the judgment of the treating physician.

The term "excipient" means a pharmacologically inactive component such as a diluent, lubricant, surfactant, carrier, or the like. Excipients that are useful in preparing a pharmaceutical composition are generally safe, non-toxic and are acceptable for human pharmaceutical use. Reference to an excipient includes both one and more than one such excipient. Co-processed excipients are also covered under the scope of present invention.

"Filling agents" or "fillers" include compounds such as lactose, lactose monohydrate, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, magnesium stearate, calcium hydroxide, talc, sodium stearyl fumarate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

As used herein, "CA-125" means cancer antigen 125. A CA-125 test is used to measure the amount of the protein CA-125 in the blood of a patient. A CA-125 test may be used to monitor certain cancers during and after treatment, including use to evaluate prolongation of progression free survival. In some cases, a CA-125 test may be used to look for early signs of ovarian cancer in women with a very high risk of the disease.

As used herein, a "chemotherapeutic agent" refers to a chemical agent that inhibits the proliferation, growth, lifespan and/or metastatic activity of cancer cells. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines (e.g., altretamine, triethylenemelamine, trietylenephosphoramide, triethiylenethiophosphoramide and trimethylolomelamine); acetogenins; delta-9-tetrahydrocannabinol (e.g., dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; xeloda; ibandronate; topoisomerase inhibitor RFS 2000; difluoromethylornithine (DMFO); retinoids such as retinoic acid; capecitabine; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

Also included in this definition are "antimetabolite chemotherapeutic agents" that are structurally similar to a metabolite, but cannot be used by the body in a productive manner. Many antimetabolite chemotherapeutic agents interfere with the production of the nucleic acids, RNA and DNA. Examples of antimetabolite chemotherapeutic agents include gemcitabine (GEMZAR®), 5-fluorouracil (5-FU), capecitabine (XELODA™), 6-mercaptopurine, methotrexate, 6-thioguanine, pemetrexed, raltitrexed, arabinosylcytosine ARA-C cytarabine (CYTOSAR-U®), dacarbazine (DTIC-DOMED), azocytosine, deoxycytosine, pyridmidene, fludarabine (FLUDARA®), cladrabine, 2-deoxy-D-glucose etc. In some embodiments, an antimetabolite chemotherapeutic agent is gemcitabine. Gemcitabine HCl is sold by Eli Lilly under the trademark GEMZAR®.

Also included in this definition are "platinum-based chemotherapeutic agents" that comprises an organic compound which contains platinum as an integral part of the molecule. In some embodiments, a chemotherapeutic agent is a platinum agent. In some such embodiments, the platinum agent is selected from cisplatin, carboplatin, oxaliplatin, nedaplatin, triplatin tetranitrate, phenanthriplatin, picoplatin, or satraplatin.

As used herein, the term "treatment" (also "treat" or "treating") refers to any administration of a therapy that partially or completely alleviates, ameliorates, relives, inhibits, prevents or delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for oral administration, for example, drenches (aqueous or non-aqueous solutions or suspensions), tablets, e.g., those targeted for buccal, sublingual, and systemic absorption, boluses, powders, granules, and pastes for application to the tongue. A pharmaceutical composition can also refer to a medicament.

As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Those skilled in the art are well familiar with antibody structure and sequence elements, recognize "variable" and "constant" regions in provided sequences, and understand that there may be some flexibility in definition of a "boundary" between such domains such that different presentations of the same antibody chain sequence may, for example, indicate such a boundary at a location that is shifted one or a few residues relative to a different presentation of the same antibody chain sequence. Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]

As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution.

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

As used herein, the term "combination therapy" refers to a clinical intervention in which a subject is simultaneously exposed to two or more therapeutic regimens (e.g., two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

Cancers

Cancer is an abnormal growth of cells which tend to proliferate in an uncontrolled way and, in some cases, to metastasize (spread). Cancer is not one disease. It is a group of more than 100 different and distinctive diseases. Cancer can involve any tissue of the body and have many different forms in each body area. Most cancers are named for the type of cell or organ in which they start. A tumor can be cancerous or benign. A benign tumor means the tumor can grow but does not spread. A cancerous tumor is malignant, meaning it can grow and spread to other parts of the body. If a cancer spreads (metastasizes), the new tumor bears the same name as the original (primary) tumor. The frequency of a particular cancer may depend on gender. While skin cancer is the most common type of malignancy for both men and women, the second most common type in men is prostate cancer and in women, breast cancer.

The methods of the disclosure can be used to treat any type of cancer known in the art. Non-limiting examples of cancers to be treated by the methods of the present disclosure can include melanoma (e.g., metastatic malignant melanoma), renal cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. Additionally, the invention includes refractory or recurrent malignancies whose growth may be inhibited using the methods of the invention. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, tongue, larynx, and gullet), and adenocarcinoma (for example, prostate, small intestine, endometrium, cervical canal, large intestine, lung, pancreas, gullet, intestinum rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma.

In some embodiments, a patient or population of patients to be treated with a combination therapy of the present disclosure have a solid tumor. In some embodiments, a solid tumor is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma. In some embodiments, a patient or population of patients to be treated with a combination therapy of the present disclosure have a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), or Multiple myeloma ("MM").

Role of Poly(ADP-Ribose) Polymerases (PARPs)

Poly(ADP-ribose) polymerases (PARPs) are a family of enzymes that cleave NAD+, releasing nicotinamide, and successively add ADP-ribose units to form ADP-ribose polymers. Accordingly, activation of PARP enzymes can lead to depletion of cellular NAD+ levels (e.g., PARPs as NAD+ consumers) and mediates cellular signaling through ADP-ribosylation of downstream targets. PARP-1 is a zinc-finger DNA-binding enzyme that is activated by binding to DNA double or single strand breaks. It was known that anti-alkylating agents could deplete the NAD+ content of tumor cells, and the discovery of PARPs explained this phenomena. (Parp Inhibitors and Cancer Therapy. Curtin N. in Poly ADP Ribosylation. ed. Alexander Burke, Lands Bioscience and Springer Bioscience, 2006: 218-233). Anti-alkylating agents induce DNA strand breaks, which activates of PARP-1, which is part of the DNA repair pathway. Poly ADP-ribosylation of nuclear proteins by PARP-1 converts DNA damage into intracellular signals that can either activate DNA repair (e.g., by the base excision repair (BER) pathway); or trigger cell death in the presence of DNA damage that is too extensive and cannot be efficiently repaired.

PARP-2 contains a catalytic domain and is capable of catalyzing a poly(ADP-ribosyl)ation reaction. PARP-2 displays auto-modification properties similar to PARP-1. The protein is localized in the nucleus in vivo and may account for the residual poly(ADP-ribose) synthesis observed in PARP-1-deficient cells, treated with alkylating agents or hydrogen peroxide. Some agents that inhibit PARP (e.g., agents primarily aimed at inhibiting PARP-1) may also inhibit PARP-2 (e.g., niraparib).

The role of PARP enzymes in DNA damage response (e.g., repair of DNA in response to genotoxic stress) has led to the compelling suggestion that PARP inhibitors may be useful anti-cancer agents. PARP inhibitors may be particularly effective in treating cancers resulting from germ line or sporadic deficiency in the homologous recombination DNA repair pathway, such as BRCA-1 and/or BRCA-2 deficient cancers.

Pre-clinical ex vivo and in vivo experiments suggest that PARP inhibitors are selectively cytotoxic for tumors with homozygous inactivation of BRCA-1 and/or BRCA-2 genes, which are known to be important in the homologous recombination (HR) DNA repair pathway. The biological basis for the use of PARP inhibitors as single agents in cancers with defects in BRCA-1 and/or BRCA-2 is the requirement of PARP-1 and PARP-2 for base excision repair (BER) of the damaged DNA. Upon formation of single-strand DNA breaks, PARP-1 and PARP-2 bind at sites of lesions, become activated, and catalyze the addition of long polymers of ADP-ribose (PAR chains) on several proteins associated with chromatin, including histones, PARP itself, and various DNA repair proteins. This results in chromatin relaxation and fast recruitment of DNA repair factors that access and repair DNA breaks. Normal cells repair up to 10,000 DNA defects daily and single strand breaks are the most common form of DNA damage. Cells with defects in the BER pathway enter S phase with unrepaired single strand breaks. Pre-existing single strand breaks are converted to double strand breaks as the replication machinery passes through the break. Double strand breaks present during S phase are preferentially repaired by the error-free HR pathway. Cells with inactivation of genes required for HR, such as BRCA-1 and/or BRCA-2, accumulate stalled replication forks during S phase and may use error-prone non-homologous end joining (NHEJ) to repair damaged DNA. Both the inability to complete S phase (because of stalled replication forks) and error-prone repair by NHEJ, are thought to contribute to cell death.

Without wishing to be bound by theory, it is hypothesized that treatment with PARP inhibitors may selectively kill a subset of cancer cells with deficiencies in DNA repair pathways (e.g., inactivation of BRCA-1 and/or BRCA-2). For example, a tumor arising in a patient with a germline BRCA mutation has a defective homologous recombination DNA repair pathway and would be increasingly dependent on BER, a pathway blocked by PARP inhibitors, for maintenance of genomic integrity. This concept of inducing death by use of PARP inhibitors to block one DNA repair pathway in tumors with pre-existing deficiencies in a complementary DNA repair pathways is called synthetic lethality.

The therapeutic potential of PARP inhibitors is further expanded by the observation that PARP inhibitors not only have monotherapy activity in HR-deficient tumors, but are also effective in preclinical models in combination with other agents such as cisplatin, carboplatin, alkylating and methylating agents, radiation therapy, and topoisomerase I inhibitors. In contrast to the rationale for monotherapy in which PARP inhibition alone is sufficient for cell death in HR-deficient cancers (due to endogenous DNA damage), PARP is required for repair of DNA damage induced by standard cytotoxic chemotherapy. In some cases, the specific role of PARP is not known, but PARP is known to be required to release trapped topoisomerase I/irinotecan complexes from DNA. Temozolomide-induced DNA damage is repaired by the BER pathway, which requires PARP to recruit repair proteins. Combination therapies that enhance or synergize the cancer therapy without significantly increasing toxicity would provide substantial benefit to cancer patients, including ovarian cancer patients.

PARP Inhibitors

PARP inhibitors have shown activity against tumors with existing DNA repair defects, such as BRCA1 and BRCA2. Without wishing to be bound by theory, treatment with PARP inhibitors (e.g., PARP-1/2 inhibitors) may selectively kill a subset of cancer cell types by exploiting their deficiencies in DNA repair. Human cancers exhibit genomic instability and an increased mutation rate due to underlying defects in DNA repair. These deficiencies render cancer cells more dependent on the remaining DNA repair pathways and targeting these pathways is expected to have a much greater impact on the survival of the tumor cells than on normal cells.

In some embodiments, a PARP inhibitor increases infiltration of T cells in the tumor microenvironment. In some embodiments, a PARP inhibitor increases infiltration of CD4$^+$ T cells in the tumor microenvironment. In some embodiments, a PARP inhibitor increases infiltration of CD8$^+$ T cells in the tumor microenvironment. In some embodiments, a PARP inhibitor increases infiltration of CD4$^+$ and CD8$^+$ T cells in the tumor microenvironment. In some embodiments, a PARP inhibitor increases infiltration of macrophages in the tumor microenvironment. In some embodiments, a PARP inhibitor increases infiltration of Treg cells into the tumor microenvironment. In some embodiments, a PARP inhibitor increases infiltration of CD335$^+$ T cells in the tumor microenvironment. In some embodiments, a PARP inhibitor increases infiltration of Fox3p$^+$ T cells in the tumor microenvironment. In some embodiments, a PARP inhibitor increases infiltration of Iba1$^+$ T cells in the tumor microenvironment.

In some embodiments, agents that inhibit PARP include agents that inhibit PARP-1 and/or PARP-2. In some embodiments, agents that inhibit PARP include ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof. In some embodiments, a PARP inhibitor is niraparib, olaparib, rucaparib, talazoparib, veliparib, or any combination thereof. In some embodiments, a PARP inhibitor can be prepared as a pharmaceutically acceptable salt. In some embodiments, an agent that inhibits PARP is niraparib or a salt or derivative thereof. One of skill in the art will appreciate that such salt forms can exist as solvated or hydrated polymorphic forms.

Niraparib

Niraparib is an orally active and potent poly (ADP-ribose) polymerase, or PARP, inhibitor. Niraparib and pharmaceutically acceptable salts thereof, are disclosed in International Publication No. WO2007/113596 and European Patent No. EP2007733B1; International Publication No. WO2008/084261 and U.S. Pat. No. 8,071,623; and International Publication No. WO2009/087381 and U.S. Pat. No. 8,436,185. Methods of making niraparib and pharmaceutically acceptable salts thereof are disclosed in International Publication Nos. WO2014/088983 and WO2014/088984. Methods to treat cancer with niraparib and pharmaceutically acceptable salts thereof are disclosed in U.S. Provisional Patent Application Nos. 62/356,461 and 62/402,427. The contents of each of the foregoing references are incorporated herein by reference in their entirety.

In some embodiments, the present invention relates to use of niraparib in combination with one or more additional pharmaceutically active agents affecting activity within the tumor microenvironment. Niraparib, (3S)-3-[4-{7-(aminocarbonyl)-2H-indazol-2-yl}phenyl]piperidine, is an orally available, potent, poly (adenosine diphosphate [ADP]-ribose) polymerase (PARP)-1 and -2 inhibitor. Niraparib has the following structure:

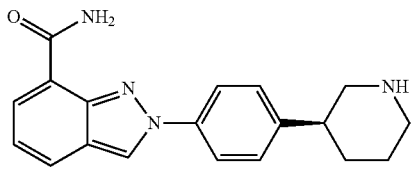 [SMILES: NC(=O)c1cccc2cn(-c3ccc([C@@H]4CCCNC4)cc3)nc12]

The empirical molecular formula for niraparib is $C_{26}H_{30}N_4O_5S$ and its molecular weight is 510.61. Niraparib tosylate monohydrate drug substance is a white to off-white, non-hygroscopic crystalline solid. Niraparib solubility is pH independent below the pKa of 9.95, with an aqueous free base solubility of 0.7 mg/mL to 1.1 mg/mL across the physiological pH range. See WO 2008/084261 (published on Jul. 17, 2008) and WO 2009/087381 (published Jul. 16, 2009), the entirety of each of which is hereby incorporated by reference. Niraparib can be prepared according to Scheme 1 of WO 2008/084261. As used herein, the term "niraparib" means any of the free base compound ((3S)-3-[4-{7-(aminocarbonyl)-2H-indazol-2-yl}phenyl]piperidine), a salt form, including pharmaceutically acceptable salts, of (3 S)-3-[4-{7-(aminocarbonyl)-2H-indazol-2-yl}phenyl]piperidine (e.g., (3S)-3-[4-{7-(aminocarbonyl)-2H-indazol-2-yl}phenyl]piperidine tosylate), or a solvated or hydrated form thereof (e.g., (3 S)-3-[4-{7-(aminocarbonyl)-2H-indazol-2-yl}phenyl]piperidine tosylate monohydrate). In some embodiments, such forms may be individually referred to as "niraparib free base", "niraparib tosylate" and "niraparib tosylate monohydrate", respectively. Unless otherwise specified, the term "niraparib" includes all forms of the compound (3S)-3-[4-{7-(aminocarbonyl)-2H-indazol-2-yl}phenyl]piperidine.

In some embodiments, niraparib can be prepared as a pharmaceutically acceptable salt. One of skill in the art will appreciate that such salt forms can exist as solvated or hydrated polymorphic forms. In some embodiments, niraparib is prepared in the form of a hydrate.

In certain embodiments, niraparib is prepared in the form of a tosylate salt. In some embodiments, niraparib is prepared in the form of a tosylate monohydrate.

The crystalline tosylate monohydrate salt of niraparib is being developed as a monotherapy agent for tumors with defects in the homologous recombination (HR) deoxyribonucleic acid (DNA) repair pathway and as a sensitizing agent in combination with cytotoxic agents and radiotherapy.

Provided herein are compositions containing niraparib or its pharmaceutically acceptable salts. The compositions may further include one or more additional active ingredients which impact activity in the tumor microenvironment (e.g., activity of T cells and/or the infiltration of T cells into the tumor environment).

In some embodiments, the niraparib a pharmaceutically acceptable salt thereof. In some embodiments, the pharmaceutically acceptable salt is niraparib tosylate monohydrate.

The formulation can comprise one or more components, including niraparib. The components can be combined to create granules that are then compressed to form tablets.

The niraparib may be present in the formulation as a pharmaceutically acceptable salt. For example, the niraparib can be niraparib tosylate monohydrate.

The niraparib formulations described herein are administered and dosed in accordance with good medical practice, taking into account the clinical condition of the individual patient, the site and method of administration, scheduling of administration, and other factors known to medical practitioners. In human therapy, the dosage forms described herein deliver niraparib formulations that maintain a therapeutically effective amount of niraparib in plasma the while reducing the side effects associated with an elevated $C_{max}$ blood plasma level of niraparib.

Pharmaceutically Acceptable Salts

In some embodiments, the niraparib used in a composition disclosed herein is the form of a free base, pharmaceutically acceptable salt, prodrug, analog or complex. In some instances, the niraparib comprises the form of a pharmaceutically acceptable salt. In some embodiments, with respect to niraparib in a composition, a pharmaceutically acceptable salt includes, but is not limited to, 4-methylbenzenesulfonate salts, sulfate salts, benzenesulfate salts, fumarate salts, succinate salts, and stereoisomers or tautomers thereof. In some embodiments, with respect to niraparib in a composition, a pharmaceutically acceptable salt includes, but is not limited to, tosylate salts. In some embodiments, with respect to niraparib in a composition, a pharmaceutically acceptable salt includes, but is not limited to, tosylate monohydrate salts.

Additional Pharmaceutically Acceptable Excipients

In some aspects, the pharmaceutical composition disclosed herein further comprises one or more pharmaceutically acceptable excipients. In some embodiments, the one or more pharmaceutically acceptable excipient is present in an amount of about 0.1-99% by weight. Exemplary pharmaceutically acceptable excipients for the purposes of pharmaceutical compositions disclosed herein include, but are not limited to, binders, disintegrants, superdisintegrants, lubricants, diluents, fillers, flavors, glidants, sorbents, solubilizers, chelating agents, emulsifiers, thickening agents, dispersants, stabilizers, suspending agents, adsorbents, granulating agents, preservatives, buffers, coloring agents and sweeteners or combinations thereof. Examples of binders include microcrystalline cellulose, hydroxypropyl methylcellulose, carboxyvinyl polymer, polyvinylpyrrolidone, polyvinylpolypyrrolidone, carboxymethylcellulose calcium, carboxymethylcellulose sodium, ceratonia, chitosan, cottonseed oil, dextrates, dextrin, ethylcellulose, gelatin, glucose, glyceryl behenate, galactomannan polysaccharide, hydroxyethyl cellulose, hydroxyethylmethyl cellulose, hydroxypropyl cellulose, hypromellose, inulin, lactose, magnesium aluminum silicate, maltodextrin, methylcellulose, poloxamer, polycarbophil, polydextrose, polyethylene glycol, polyethylene oxide, polymethacrylates, sodium alginate, sorbitol, starch, sucrose, sunflower oil, vegetable oil, tocofersolan, zein, or combinations thereof. Examples of disintegrants include hydroxypropyl methylcellulose (HPMC), low substituted hydroxypropyl cellulose (L-HPC), croscarmellose sodium, sodium starch glycolate, lactose, magnesium aluminum silicate, methylcellulose, polacrilin potassium, sodium alginate, starch, or combinations thereof. Examples of a lubricant include stearic acid, sodium stearyl fumarate, glyceryl behenate, calcium stearate, glycerin monostearate, glyceryl palmitostearate, magnesium lauryl sulfate, mineral oil, palmitic acid, myristic acid, poloxamer, polyethylene glycol, sodium benzoate, sodium chloride, sodium lauryl sulfate, talc, zinc stearate, potassium benzoate, magnesium stearate or combinations thereof. Examples of diluents include talc, ammonium alginate, calcium carbonate, calcium lactate, calcium phosphate, calcium silicate, calcium sulfate, cellulose, cellulose acetate, corn starch, dextrates, dextrin, dextrose, erythritol, ethylcellulose, fructose, fumaric acid, glyceryl palmitostearate, isomalt, kaolin, lactitol, lactose, magnesium carbonate, magnesium oxide, maltodextrin, maltose, mannitol, microcrystalline cellulose, polydextrose, polymethacrylates, simethicone, sodium alginate, sodium chloride, sorbitol, starch, sucrose, sulfobutylether β-cyclodextrin, tragacanth, trehalose, xylitol, or combinations thereof. In some embodiments, the pharmaceutically acceptable excipient is hydroxypropyl methylcellulose (HPMC). In some embodiments, the pharmaceutically acceptable excipient is low substituted hydroxypropyl cellulose (L-HPC). In some embodiments, the pharmaceutically acceptable excipient is lactose. In some embodiments, the pharmaceutically acceptable excipient is lactose monohydrate. In some embodiments, the pharmaceutically acceptable excipient is magnesium stearate. In some embodiments, the pharmaceutically acceptable excipient is lactose monohydrate and magnesium stearate.

Various useful fillers or diluents include, but are not limited to calcium carbonate (Barcroft™, MagGran™, Millicarb™, Pharma-Carb™, Precarb™, Sturcal™, Vivapres Ca™), calcium phosphate, dibasic anhydrous (Emcompress Anhydrous™, Fujicalin™) calcium phosphate, dibasic dihydrate (Calstar™, Di-Cafos™, Emcompress™), calcium phosphate tribasic (Tri-Cafos™, TRI-TAB™), calcium sulphate (Destab™, Drierite™, Snow White™, Cal-Tab™, Compactrol™), cellulose powdered (Arbocel™, Elcema™ Sanacet™), silicified microcrystailine cellulose, cellulose acetate, compressible sugar (Di-Pac™), confectioner's sugar, dextrates (Candex™, Emdex™), dextrin (Avedex™, Caloreen™, Primogran W™), dextrose (Caridex™, Dextrofin™, Tab fine D-IOO™) fructose (Fructofin™, Krystar™), kaolin (Lion™, Sim 90™), lactitol (Finlac DC™, Finlac MCX™), lactose (Anhydrox™, CapsuLac™, Fast-Flo™, FlowLac™, GranuLac™, InhaLac™, Lactochem™, Lactohaie™, Lactopress™, Microfme™, Microtose™, Pharmatose™, Prisma Lac™, Respitose™, SacheLac™, SorboLac™, Super-Tab™, Tablettose™, Wyndale™, Zeparox™), lactose monohydrate, magnesium carbonate, magnesium oxide (MagGran MO™), maltodextrin (C*Dry MD™, Lycatab DSH™, Maldex™, Maitagran™, Maltrin™, Maltrin QD™, Paselli MD 10 PH™, Star-Dri™) maltose (Advantose 100™), mannitol (Mannogem™, Pearlitol™), microcrystalline cellulose (Avicel PH™, Celex™, Celphere™, Ceolus KG™, Emcocel™, Pharmacel™, Tabulose™, Vivapur™), polydextrose (Litesse™), simethicone (Dow Corning Q7-2243 LVA™, Cow Coming Q7-2587™, Sentry Simethicone™), sodium alginate (Keltone™, Protanal™) sodium chloride (Alberger™), sorbitol (Liponec 70-NC™, Liponic 76-NCv, Meritol™, Neosorb™, Sorbitol Instant™, Sorbogem™), starch (Flufiex W™, Instant Pure-Cote™, Melojei™, Meritena Paygel 55™, Perfectamyl D6PH™, Pure-Cote™, Pure-Dent™, Pure-Gel™, Pure-Set™, Purity 21™, Purity 826™, Tablet White™), pregelatinized starch, sucrose, trehalose and xylitol, or mixtures thereof.

Various useful disintegrants include, but are not limited to, alginic acid (Protacid™, Satialgine H8™), calcium phosphate, tribasic (TRI-TAB™), carboxymethylcellulose calcium (ECG 505™), carboxymethylcellulose sodium (Akucell™ Finnfix™, Nymcel Tylose CB™), colloidal silicon dioxide (Aerosil™, Cab-O-Sil™, Wacker HDK™), croscarmellose sodium (Ac-Di-Sol™, Pharmacel XL™, Primellose™, Solutab™, Vivasol™), crospovidone (Collison CL™, Collison CL-M™, Polyplasdone XL™), docusate sodium, guar gum (Meyprodor™, Meyprofm™, Meyproguar™), low substituted hydroxypropyl cellulose, magnesium aluminum silicate (Magnabite™, Neusilin™, Pharmsorb™, Veegum™), methylcellulose (Methocel™, Metolose™), microcrystalline cellulose (Avicel PH™, Ceoius KG™, Emcoel™, Ethispheres™, Fibrocel™, Pharmacel™, Vivapur™), povidone (Collison™, Plasdone™) sodium alginate (Kelcosol™, Ketone™, Protanal™), sodium starch glycolate, polacrilin potassium (Amberlite IRP88™), silicified microcrystalline cellulose (ProSotv™), starch (Aytex P™, Fluftex W™, Melojel™, Meritena™, Paygel 55™ Perfectamyl D6PH™, Pure-Bind™, Pure-Cote™, Pure-Dent™, Purity 21™, Purity 826™, Tablet White™) or pre-gelatinized starch (Lycatab PGS™, Merigel™, National 78-1551™, Pharma-Gel™, Prejel™, Sepistab ST 200™, Spress B820™, Starch 1500 G™, Tablitz™, Unipure LD™), or mixtures thereof.

Various useful lubricants include, but are not limited to, calcium stearate (HyQual™), glycerine monostearate (Imwitor™ 191 and 900, Kessco GMS5™, 450 and 600, Myvaplex 600P™, Myvatex™, Rita GMS™, Stepan GMS™, Tegin™, Tegin™ 503 and 515, Tegin 4100™, Tegin M™, Unimate GMS™), glyceryl behenate (Compritol 888 ATO™), glyceryl palmitostearate (Precirol ATO 5™) hydrogenated castor oil (Castorwax MP 80™, Croduret™, Cutina HR™, Fancol™, Simulsol 1293™), hydrogenated vegetable oil 0 type I (Sterotex™, Dynasan P60™, Hydrocote™, Lipovol HS-K™, Sterotex HM™), magnesium lauryl sulphate, magnesium stearate, medium-chain triglycerides (Captex 300™, Labrafac CC™, Miglyol 810™, Neobee MS™, Nesatol™, Waglinol 3/9280™), poloxamer (Pluronic™, Synperonic™), polyethylene 5 glycol (Carbowax Sentry™, Lipo™, Lipoxol™, Lutrol E™, Pluriol E™), sodium benzoate (Antimol™), sodium chloride, sodium lauryl sulphate (Elfan 240™, Texapon Kl 2P™), sodium stearyl fumarate (Pruv™), stearic acid (Hystrene™, Industrene™, Kortacid 1895™, Pristerene™), talc (Altaic™, Luzenac™, Luzenac Pharma™, Magsil Osmanthus™, 0 Magsil Star™, Superiore™), sucrose stearate (Surfhope SE Pharma D-1803 F™) and zinc stearate (HyQual™) or mixtures thereof. Examples of suitable lubricants include, but are not limited to, magnesium stearate, calcium stearate, zinc stearate, stearic acid, talc, glyceryl behenate, polyethylene glycol, polyethylene oxide polymers, sodium lauryl sulfate, magnesium lauryl sulfate, sodium oleate, sodium stearyl fumarate, DL-leucine, colloidal silica, and others as known in the art. In some embodiments a lubricant is magnesium stearate.

Various useful glidants include, but are not limited to, tribasic calcium phosphate (TRI-TAB™), calcium silicate, cellulose, powdered (Sanacel™, Solka-Floe™), colloidal silicon dioxide (Aerosil™, Cab-O-Sil M-5P™, Wacker HDK™), magnesium silicate, magnesium trisilicate, starch (Melojel™, Meritena™, Paygel 55™ Perfectamyl D6PH™, Pure-Bind™, Pure-Cote™, Pure-Dent™, Pure-Gel™, Pure-Set™, Purity 21™, Purity 826™, Tablet White™) and talc (Luzenac Pharma™, Magsil Osmanthus™, Magsil Star™, Superiore™), or mixtures thereof.

Pharmaceutically acceptable surfactants include, but are limited to both non-ionic and ionic surfactants suitable for use in pharmaceutical dosage forms. Ionic surfactants may include one or more of anionic, cationic or zwitterionic surfactants. Various useful surfactants include, but are not limited to, sodium lauryl sulfate, monooleate, monolaurate, monopalmitate, monostearate or another ester of olyoxyethylene sorbitane, sodium dioctylsulfosuccinate (DOSS), lecithin, stearyic alcohol, cetostearylic alcohol, cholesterol, polyoxyethylene ricin oil, polyoxyethylene fatty acid glycerides, poloxamer, or any other commercially available co-processed surfactant like SEPITRAP® 80 or SEPITRAP® 4000 and mixtures thereof.

T Cells

T cells can be either $CD4^+$ or $CD8^+$ T cells, and can be CD28 positive T cells or CD28 negative T cells. T cells can also be either memory T cells or naïve T cells. Furthermore, T cells can express CD3. T cells can be regulatory cells. In some embodiments, T regulatory cells express proteins, including, for example CD25, CTLA-4, or FoxP3, or combinations thereof. In some embodiments, T cells are Th1 cells or Th2 cells. In some embodiments, Th1 cells are capable of secreting cytokines including, for example, interferon gamma, interleukin 2, and TNF-beta. In some embodiments, Th1 cells express markers, including, for example, CD4, CD94, CD119 (IFNγ R1), CD183 (CXCR3), CD186 (CXCR6), CD191 (CCR1), CD195 (CCR5), CD212 (IL-12Rβ1&2), CD254 (RANKL), CD278 (ICOS), IL-18R, MRP1, NOTCH3, or TIM3, or combinations thereof. In some embodiments, Th2 cells are capable of secreting cytokines including, for example, IL-4, IL-5, IL-6, IL-9, IL-10, or IL-13, or combinations thereof. In some embodiments, Th2 cells express markers including, for example, CRTH2, CCR4, or CCR3, or combinations thereof.

Promoting Antigen Specific T Cell Signaling

T cells are a class of lymphocytes, having specific T cell receptors (TCRs) that are produced as a result of gene rearrangement. T cells have diverse roles, which are accomplished by the differentiation of distinct subsets of T cells, recognizable by discrete patterns of gene expression. T cells capable of antigen recognition (e.g., antigen-specific T cells) are generally classified as "$CD4^+$" or "$CD8^+$," depending on whether a CD4 or a CD8 molecule is displayed on the cell surface. $CD4^+$ cells recognize exogenously-produced antigen which has been taken up by an antigen presenting cell (APC), processed, and displayed on the APC cell surface together with a major histocompatibility complex (MHC) class II molecule. In general, $CD4^+$ T cells provide the signals to activate other cells, e.g., $CD4^+$ cells activate $CD8^+$ cells, to induce B cells to produce antibodies, or to activate macrophages. In contrast, $CD8^+$ cells are cytotoxic, and recognize antigen produced from within a cell and displayed on the cell surface together with an MHC Class I molecule.

In some embodiments, a combination therapy comprises one or more agents that activate T cell proliferation and/or stimulate antigen-specific T cell activity. An agent that activates antigen-specific T cell proliferation and/or activity may be or comprise an agent of any chemical class including, for example, a carbohydrate, a lipid, a nucleic acid, a polypeptide, a small molecule, a metal, a cell, etc. In some embodiments, an agent that activates antigen-specific T cell proliferation and/or activity may be or comprise a polypeptide (or complex thereof). In some embodiments, an agent that activates antigen-specific T cell proliferation and/or activity may be or comprise an antibody agent, a cytokine, a ligand, a receptor, a toxin, etc.

An agent that activates or stimulates antigen-specific T cell activity typically functions to enhance the total activity of antigen-specific T cells in a tumor microenvironment in order to initiate, strengthen or maintain an anti-tumor immunogenic response. In some embodiments, activation of antigen-specific T cell activity involves the stimulation of individual antigen-specific T cells (e.g., $CD4^+$ or $CD8^+$ cells) from an unstimulated or partially stimulated state. In some embodiments, activation of antigen-specific T cell activity involves inducing proliferation of antigen-specific T cells (e.g., $CD4^+$ or $CD8^+$ cells). In some embodiments, activation of antigen-specific T cell activity involves the recruitment of antigen-specific T cells (e.g., $CD4^+$ or $CD8^+$ cells) to a tumor microenvironment. Herein in the term "activated" in reference to an antigen-specific T cell refers to the activated state of the cell that results from an interaction between the T cell receptor of the antigen-specific T cell (e.g., $CD4^+$ or $CD8^+$ cell) and an activating signal (e.g., peptide antigen) specific for the T cell receptor presented to the antigen-specific T cell by an antigen-presenting cell. A composition can comprise a disease-specific immunogenic neoantigen peptide. A composition can comprise two or more disease-specific immunogenic neoantigen peptides. A composition may comprise a precursor to a disease-specific immunogenic peptide (such as a protein, peptide, DNA and RNA). A precursor to a disease-specific immunogenic peptide can generate or be generated to the identified disease-specific immunogenic neoantigen peptide. In some embodiments, a therapeutic composition comprises a precursor of an immunogenic peptide. The precursor to a disease-specific immunogenic peptide can be a pro-drug. In some embodiments, the composition comprising a disease-specific immunogenic neoantigen peptide may further comprise an adjuvant. For example, the neoantigen peptide can be utilized as a vaccine. In some embodiments, an immunogenic vaccine may comprise a pharmaceutically acceptable immunogenic neoantigen peptide. In some embodiments, an immunogenic vaccine may comprise a pharmaceutically acceptable precursor to an immunogenic neoantigen peptide (such as a protein, peptide, DNA and RNA). In some embodiments, the neoantigen peptide is directed to a shared antigen that can be recognized by patient T cells within a large patient group. In some embodiments, a method of treatment comprises administering to a subject an effective amount of an antibody specifically recognizing an immunogenic neoantigen peptide.

The methods described herein can be useful in the personalized medicine context, where immunogenic neoantigen peptides are used to develop therapeutics (such as vaccines or therapeutic antibodies) for the same individual. Thus, a method of treating a disease in a subject can comprise identifying an immunogenic neoantigen peptide in a subject according to the methods described herein; and synthesizing the peptide (or a precursor thereof); and administering the peptide or an antibody specifically recognizing the peptide to the subject. In some embodiments, an expression pattern of an immunogenic neoantigen can serve as the essential basis for the generation of patient specific vaccines. In some embodiments, an expression pattern of an immunogenic neoantigen can serve as the essential basis for the generation of a vaccine for a group of patients with a particular disease. Thus, particular diseases, e.g., particular types of tumors, can be selectively treated in a patient group.

There are a variety of ways in which to produce immunogenic neoantigens. Proteins or peptides may be made by any technique known to those of skill in the art, including the expression of proteins, polypeptides or peptides through standard molecular biological techniques, the isolation of proteins or peptides from natural sources, in vitro translation, or the chemical synthesis of proteins or peptides. In general, such disease specific neoantigens may be produced either in vitro or in vivo. Immunogenic neoantigens may be produced in vitro as peptides or polypeptides, which may then be formulated into a personalized vaccine or immunogenic composition and administered to a subject. In vitro production of immunogenic neoantigens can comprise peptide synthesis or expression of a peptide/polypeptide from a DNA or RNA molecule in any of a variety of bacterial, eukaryotic, or viral recombinant expression systems, followed by purification of the expressed peptide/polypeptide. Alternatively, immunogenic neoantigens can be produced in vivo by introducing molecules (e.g., DNA, RNA, and viral expression systems) that encode an immunogenic neoantigen into a subject, whereupon the encoded immunogenic neoantigens are expressed. In some embodiments, a polynucleotide encoding an immunogenic neoantigen peptide can be used to produce the neoantigen peptide in vitro.

In some embodiments, a polynucleotide comprises a sequence with at least 60%, 65%, 70%1, 75%, 80%, 85%, 90%, 95%, 96%, 97%, 98%, 99%, or 100% identity to a polynucleotide encoding an immunogenic neoantigen.

The polynucleotide may be, e.g., DNA, cDNA, PNA, CNA, RNA, single- and/or double-stranded, native or stabilized forms of polynucleotides, or combinations thereof. A nucleic acid encoding an immunogenic neoantigen peptide may or may not contain introns so long as it codes for the peptide. In some embodiments in vitro translation is used to produce the peptide.

Cytokines

In some embodiments an agent that activates an antigen-specific T cell proliferation and/or activity is an interleukin or an agent that increases the expression and/or activity of an interleukin. For example, Interleukin-2 (IL-2) is a cytokine synthesized by T-cells which was first identified in conjunction with its role in the expansion of T-cells in response to an antigen (Smith, K. A. *Science* 240:1169 (1988)). Several studies have demonstrated that IL-2 has antitumor effects (see e.g., Lotze, M. T. et al, in "*Interleukin* 2", ed. K. A. Smith, Academic Press, Inc., San Diego, Calif., p 237 (1988); Rosenberg, S., *Ann. Surgery* 208:121 (1988)). In fact, IL-2 has been utilized to treat subjects suffering from malignant melanoma, renal cell carcinoma, and acute myelogenous leukemia. (Rosenberg, S. A., et al., *N. Eng. J. Med.* 316:889-897 (1987); Dutcher, J. P., et al., *J. Clin. Oncol.* 7:477-485 (1989); Foa, R., et al., *Br. J. Haematol.* 77:491-496 (1991)).

In some embodiments, other interleukins, such as IL-1, IL-7, IL-15, IL-12 and IL-18 can be employed to activate antigen-specific T cells in a tumor microenvironment. These interleukins have been shown to directly promote antigen-specific T cell proliferation/survival and development of cytolytic effector functions. In some cases, these interleukins act on cytokine-induced killer (CIK) cells, which are a heterogeneous population of effector $CD8^+$ T cells with diverse TCR specificities, possessing non-MHC-restricted cytolytic activities against tumor cells.

Another cytokine which in some embodiments may activate an antigen-specific T cell is interferon-α (IFN-α). IFN-α is an IFN type I cytokine, has been employed to treat leukemia, myeloma, and renal cell carcinomas. IFN type I cytokines have been shown to increases class I MHC molecule expression. Because most cytolytic T-cells (CTLs) recognize foreign antigens bound to class I MHC molecules, type I IFNs may boost the effector phase of cell-mediated immune responses by enhancing the efficiency of CTL-mediated killing. At the same time, type I IFN may inhibit the cognitive phase of immune responses, by preventing the activation of class II MHC-restricted helper T-cells.

Members of the chemokine family of cytokines may also act to promote antigen-specific T cell anti-tumor activity. Chemokines are known to act as a chemoattractant to mediate chemotaxis in nearby responsive cells. In cases where responsive T cells express T cell receptors which are specific for tumor antigens, administration of chemokines can contribute to anti-tumor activity. For example, expression of the cytokine CXCL16 by tumor cells can enhance recruitment of tumor infiltrating cells such as $CD4^+$ and $CD8^+$ T cells to the tumor, via binding of CXCL16 to its receptor CXCR6 expressed in T cells.

Checkpoint Inhibitors

A balance between co-stimulatory and inhibitory signals regulates the amplitude and the quality of T-cell responses driven by TCR signaling. T cells require CD28-mediated co-stimulation (also known as signal 2) for the full acquisition of effector functions. However, excessive T-cell activation can result in the loss of self-tolerance, underscoring the importance of immune inhibitory pathways, or immune checkpoints, that regulate T-cell activity. The immunosuppressive tumor microenvironment directly affects the expression of immune checkpoint proteins, thereby favoring resistance to anti-tumor immune response. T cells are essential effectors for cancer immune surveillance, and inhibition of T-cell-dependent anti-tumor response can promote tumor progression. Engagement of the CD28 homologue receptor cytotoxic T-lymphocyte-associated protein 4 (CTLA-4) on T cells by co-stimulatory molecules negatively regulates T-cell activation. It has been demonstrated that administration of neutralizing CTLA-4 antibody into tumor-bearing mice resulted in tumor rejection. In addition, mice that had rejected their tumors following anti-CTLA-4 treatment were protected against subsequent tumor rechallenge, indicating the establishment of immunological memory. Additional mouse and human studies have validated these results and shown that CTLA-4 blockade triggers anticancer immune responses. For example, administration of the anti-CTLA-4 antibody tremelimumab to human patients resulted in a highly significant increase in intratumoral infiltration by $CD8^+$ cells in biopsy samples taken after tremelimumab treatment (Huang et al., "CTLA4 blockade induces frequent tumor infiltration by activated lymphocytes regardless of clinical response in humans," *Clin Can Res,* 17:4101-4109 (2011)). Importantly, inhibition of CTLA-4 signaling not only enhances effector T-cell functions, but it also renders effector T cells insensitive to regulatory T-cell-driven suppression. Infusion of anti-CTLA-4 antibodies after vaccination with irradiated, autologous tumor cells secreting GM-CSF (GVAX)-induced anti-tumor immunity but no toxicity in metastatic melanoma patients. The clinical efficacy of anti-CTLA-4 therapy was further confirmed in a phase III clinical trial where ipilimumab, a human mAb against CTLA-4, was shown to enhance the overall survival of metastatic melanoma patients. The demonstrated anticancer activity of ipilimumab (Yervoy) led to its approval by the FDA for the treatment of metastatic melanoma.

Other key inhibitory checkpoints that are relevant in cancer immunotherapy include PD-1 and Tim-3. Expression of the PD-1 receptor is induced in T cells upon activation [48]. Tumor cells can drive T-cell dysfunction because of their expression of PD-1 receptor ligands, PD-L1 and PD-L2. It has been demonstrated that transgenic expression of PD-L1 in mastocytoma tumor cells prevented their elimination by CTL and enhanced their invasiveness in vivo. Thus, cancer tissues limit the host immune response through PD-1 ligands and their ligation to PD-1 on antigen-specific CD8 T cells, a phenomenon termed adaptive immune resistance. The molecular bases accounting for adaptive immune resistance remain elusive. However, it has been suggested that the therapeutic efficacy of PD-1 blockade is due to the restoration of CD8 T-cell effector function in the tumor microenvironment. Preclinical models have demonstrated that blockade of PD-L1/PD-1 interactions could reinforce anticancer immune responses and promote tumor control. Tim-3 is another T-cell inhibitory receptor that was initially identified on fully differentiated Th1 cells. The Tim-3 ligand, galectin-9, induces T-cell death. In the tumor microenvironment, dysfunctional CD8 T cells could be identified by the co-expression of Tim-3 and PD-1. Tim-3 and PD-1 expression are associated with tumor antigen-specific $CD8^+$ T-cell dysfunction in melanoma patients and prevent the expansion of tumor antigen-specific CD8+ T cells induced by vaccination. Other therapies targeting immune checkpoints are currently in development such as agonist antibodies targeting molecules which activate T cells such as CD137 (BMS-663513), OX40 (MEDI6383) NCT02221960, CD40 (CP870,893) or GITR (TRAX518) NCT01239134 as well as drugs favoring DC activation such as LAG3-Fusion protein (IMP321)

Programmed Death 1 (PD-1)

Programmed Death 1 (PD-1) (also known as Programmed Cell Death 1) (encoded by the gene Pdcd1) is a type I transmembrane protein of 268 amino acids originally identified by subtractive hybridization of a mouse T cell line undergoing apoptosis (Ishida et al., *Embo J.*, 11: 3887-95 (1992)). The normal function of PD-1, expressed on the cell surface of activated T cells under healthy conditions, is to down-modulate unwanted or excessive immune responses, including autoimmune reactions.

PD-1 is a member of the CD28/CTLA-4 family of T-cell regulators, and is expressed on activated T-cells, B-cells, and myeloid lineage cells (Greenwald et al., *Annu. Rev. Immunol.*, 23: 515-548 (2005); and Sharpe et al., *Nat. Immunol.*, 8: 239-245 (2007)). PD-1 is an inhibitory member of the CD28 family of receptors that also includes CD28, CTLA-4, ICOS and BTLA. PD-1 is expressed on activated B cells, T cells, and myeloid cells (Agata et al., supra; Okazaki et al. (2002) *Curr. Opin. Immunol.* 14:391779-82; Bennett et al. (2003) *J. Immunol.* 170:711-8).

Two ligands for PD-1 have been identified, PD ligand 1 (PD-L1) and PD ligand 2 (PD-L2), both of which belong to the B7 protein superfamily (Greenwald et al, supra). PD-1 has been shown to negatively regulate antigen receptor signaling upon engagement of its ligands (PD-L1 and/or PD-L2).

PD-L1 is expressed in a variety of cell types, including cells of the lung, heart, thymus, spleen, and kidney (see, e.g., Freeman et al., *J. Exp. Med.*, 192(7): 1027-1034 (2000); and Yamazaki et al., *J. Immunol.*, 169(10): 5538-5545 (2002)). PD-L1 expression is unregulated on macrophages and dendritic cells (DCs) in response to lipopolysaccharide (LPS) and GM-CSF treatment, and on T-cells and B-cells upon signaling via T-cell and B-cell receptors. PD-L1 also is expressed in a variety of murine tumor cell lines (see, e.g., Iwai et al., *Proc. Nat.l Acad. Sci. USA*, 99(9): 12293-12297 (2002); and Blank et al., *Cancer Res.*, 64(3): 1140-1145 (2004)). In contrast, PD-L2 exhibits a more restricted expression pattern and is expressed primarily by antigen presenting cells (e.g., dendritic cells and macrophages), and some tumor cell lines (see, e.g., Latchman et al., *Nat. Immunol.*, 2(3): 261-238 (2001)). High PD-L1 expression in tumors, whether on the tumor cell, stroma, or other cells within the tumor microenvironment, correlates with poor clinical prognosis, presumably by inhibiting effector T cells and upregulating regulatory T cells (Treg) in the tumor.

PD-1 and family members are type I transmembrane glycoproteins containing an Ig variable-type (V-type) domain responsible for ligand binding and a cytoplasmic tail, which is responsible for the binding of signaling molecules. The cytoplasmic tail of PD-1 contains 2 tyrosine-based signaling motifs, an immunoreceptor tyrosine-based inhibition motif (ITIM) and an immunoreceptor tyrosine-based switch motif (ITSM). PD-1 negatively regulates T-cell activation, and this inhibitory function is linked to an ITSM in the cytoplasmic domain (see, e.g., Greenwald et al., supra; and Parry et al., *Mol. Cell. Biol.*, 25: 9543-9553 (2005)). Following T cell stimulation, PD-1 recruits the tyrosine phosphatases SHP-1 and SHP-2 to the ITSM motif within its cytoplasmic tail, leading to the dephosphorylation of effector molecules, such as CD3ζ, PKCθ and ZAP70, which are involved in the CD3 T cell signaling cascade. The mechanism by which PD-1 down-modulates T cell responses is similar to, but distinct from, that of CTLA-4. PD-1 was shown to be expressed on activated lymphocytes, including peripheral CD4+ and CD8+ T cells, B cells, T regs, and natural killer cells. Expression has also been shown during thymic development on CD4−/CD8− (double-negative) T cells, as well as subsets of macrophages and dendritic cells. The ligands for PD-1 (PD-L1 and PD-L2) are constitutively expressed or can be induced in a variety of cell types. PD-L1 is expressed at low levels on various non-hematopoietic tissues, most notably on vascular endothelium, whereas PD-L2 protein is predominantly expressed on antigen-presenting cells found in lymphoid tissue or chronic inflammatory environments. Both ligands are type I transmembrane receptors containing both IgV- and IgC-like domains in the extracellular region and short cytoplasmic regions with no known signaling motifs. Binding of either PD-1 ligand to PD-1 inhibits T cell activation triggered through the T cell receptor. PD-L2 is thought to control immune T cell activation in lymphoid organs, whereas PD-L1 serves to dampen unwarranted T cell function in peripheral tissues. Although healthy organs express little (if any) PD-L1, a variety of cancers were demonstrated to express abundant levels of this T cell inhibitor, which, via its interaction with the PD-1 receptor on tumor-specific T cells, plays a critical role in immune evasion by tumors.

PD-1 deficiency can lead to autoimmunity. For example, C57BL/6 PD-1 knockout mice have been shown to develop a lupus-like syndrome (see, e.g., Nishimura et al., *Immunity*, 11: 141-1151 (1999)). In humans, a single nucleotide polymorphism in the PD-1 gene is associated with higher incidences of systemic lupus erythematosus, type 1 diabetes, rheumatoid arthritis, and progression of multiple sclerosis (see, e.g., Nielsen et al., *Tissue Antigens*, 62(6): 492-497 (2003); Bertsias et al., *Arthritis Rheum.*, 60(1): 207-218 (2009); Ni et al, *Hum. Genet.*, 121(2): 223-232 (2007); Tahoori et al., *Clin. Exp. Rheumatol.*, 29(5): 763-767 (2011); and Kroner et al., *Ann. Neurol.*, 58(1): 50-57 (2005)). Abnormal PD-1 expression also has been implicated in T-cell dysfunctions in several pathologies, such as tumor immune evasion and chronic viral infections (see, e.g., Barber et al., *Nature*, 439: 682-687 (2006); and Sharpe et al., supra). PD-1 is abnormally expressed in a variety of cancers (see, e.g., Brown et al, *J. Immunol.*, 170: 1257-1266 (2003); and Flies et. al, Yale Journal of Biology and Medicine, 84: 409-421 (2011)), and PD-L1 expression in some renal cell carcinoma patients correlates with tumor aggressiveness.

Recent studies demonstrate that T-cell suppression induced by PD-1 also plays a role in the suppression of anti-tumor immunity. For example, PD-L1 is expressed on a variety of human and mouse tumors, and binding of PD-1 to PD-L1 on tumors results in T-cell suppression and tumor immune evasion and protection (Dong et al., *Nat. Med.*, 8: 793-800 (2002)). Expression of PD-L1 by tumor cells has been directly associated with their resistance to lysis by anti-tumor T-cells in vitro (Dong et al., supra; and Blank et al., *Cancer Res.*, 64: 1140-1145 (2004)). PD-1 knockout mice are resistant to tumor challenge (Iwai et al., *Int. Immunol.*, 17: 133-144 (2005)), and T-cells from PD-1 knockout mice are highly effective in tumor rejection when adoptively transferred to tumor-bearing mice (Blank et al., supra). Blocking PD-1 inhibitory signals using a monoclonal antibody can potentiate host anti-tumor immunity in mice (Iwai et al., supra; and Hirano et al., *Cancer Res.*, 65: 1089-1096 (2005)), and high levels of PD-L1 expression in tumors are associated with poor prognosis for many human cancer types (Hamanishi et al., *Proc. Natl. Acad. Sci. USA*, 104: 3360-335 (2007), Brown et al, *J. Immunol.*, 170: 1257-1266 (2003); and Flies et al., *Yale Journal of Biology and Medicine*, 84(4): 409-421 (2011)).

Further, several studies have shown that interaction of PD-1 with its ligands (PD-L1 and PD-L2) promotes inhibition of lymphocyte proliferation in vitro and in vivo. Blockade of the PD-1/PD-L1 interaction may accordingly lead to enhanced tumor-specific T-cell immunity and therefore be helpful in clearance of tumor cells by the immune system. For example, in a murine model of aggressive pancreatic cancer, the therapeutic efficacy of PD-1/PD-L1 blockade was demonstrated (Nomi, T., et al. (2007) *Clin. Cancer Res.* 13: 2151-2157). Administration of either PD-1 or PDL1 directed antibody significantly inhibited tumor growth. Antibody blockade effectively promoted tumor reactive CD8+ T cell infiltration into the tumor resulting in the up-regulation of anti-tumor effectors including IFN gamma, granzyme B and perforin. Additionally, the authors showed that PD-1 blockade can be effectively combined with chemotherapy to yield a synergistic effect.

In view of the foregoing, strategies for inhibiting PD-1 activity to treat various types of cancer and for immunopotentiation (e.g., to treat infectious diseases) have been developed (see, e.g., Ascierto et al., *Clin. Cancer. Res.,* 19(5): 1009-1020 (2013)).

Agents that Inhibit PD-1 Signaling

Agents that inhibit PD-1 signaling for use in combination therapies of the present disclosure include those that bind to and block PD-1 receptors on T cells without triggering inhibitory signal transduction, agents that bind to PD-1 ligands to prevent their binding to PD-1, agents that do both, and agents that prevent expression of genes that encode either PD-1 or natural ligands of PD-1. Compounds that bind to natural ligands of PD-1 include PD-1 itself, as well as active fragments of PD-1, and in the case of the B7-H1 ligand, B7.1 proteins and fragments. Such antagonists include proteins, antibodies, anti-sense molecules and small organics.

In some embodiments, an agent that enhances T cell activity binds to human PD-1. In some embodiments an agent that enhances T cell activity binds to human PD-L1. In some embodiments, an agent that enhances T cell activity is a monoclonal antibody, or a fragment thereof. In some embodiments, an antibody agent that enhances T cell activity is a PD-1 or PD-L1 antibody or fragment thereof. Examples of such agents that enhance T cell activity by binding to human PD-1 include BGB-A317, BI 754091, IBI308, INCSHR-1210, JNJ-63723283, JS-001, MEDI-0680, MGA-012, nivolumab, PDR001, pembrolizumab, PF-06801591, REGN-2810, TSR-042, PDR-001, camrelizumab (HR-301210), BCD-100, AGEN-2034, CS1001, Sym-021, LZMO09, KN-035, AB122, genolimzumab (CBT-501), AK 104, GLS-010, any of the antibodies disclosed in WO2014/179664, PCT/US17/59618, PCT/US18/13029, and derivatives thereof. Examples of agents that enhance T cell activity by binding to human PD-L1 include atezolizumab, avelumab, CX-072, durvalumab, FAZ053, LY3300054, PD-L1 millamolecule, BGB-A333, SHR-1316, CK-301, or derivatives thereof.

In some embodiments, an agent that enhances T cell activity for use in combination therapies of the present disclosure is an antibody agent. In some embodiments, a PD-1 antibody agent binds an epitope of PD-1 which blocks the binding of PD-1 to any one or more of its putative ligands. In some embodiments, a PD-1 antibody agent binds an epitope of PD-1 which blocks the binding of PD-1 to two or more of its putative ligands. In embodiments, the PD-1 antibody agent binds an epitope of a PD-1 protein which blocks the binding of PD-1 to PD-L1 and/or PD-L2. PD-1 antibody agents of the present disclosure may comprise a heavy chain constant region (Fe) of any suitable class. In some embodiments, a PD-1 antibody agent comprises a heavy chain constant region that is based upon wild-type IgG1, IgG2, or IgG4 antibodies, or variants thereof.

Tim-3

The protein T Cell Immunoglobulin and Mucin Domain-3 (TIM-3), also known as Hepatitis A Virus Cellular Receptor 2 (HAVCR2), is a Th1-specific cell surface protein that regulates macrophage activation and enhances the severity of experimental autoimmune encephalomyelitis in mice. TIM-3 is highly expressed on the surface of multiple immune cell types, including, for example, Th1 IFN-γ+ cells, Th17 cells, natural killer (NK) cells, monocytes, and tumor-associated dendritic cells (DCs). TIM-3 also is highly expressed on "exhausted" or impaired CD8+ T-cells in a variety of chronic viral infections (e.g., HIV, HCV, and HBV) and in certain cancers. Putative ligands for TIM-3 include phosphatidylserine, galectin-9, high-mobility group protein 1 (HMGB1), and carcinoembryonic antigen cell adhesion molecule 1 (CEACAM1).

TIM-3 functions to regulate various aspects of the immune response. The interaction of TIM-3 and galectin-9 (Gal-9) induces cell death and in vivo blockade of this interaction exacerbates autoimmunity and abrogates tolerance in experimental models, strongly suggesting that TIM-3 is a negative regulatory molecule. In contrast to its effect on T-cells, the TIM-3-Gal-9 interaction can exhibit antimicrobial effects by promoting macrophage clearance of intracellular pathogen. Suppression of TIM-3 has been shown to enhance the pathological severity of experimental autoimmune encephalomyelitis. Dysregulation of the TIM-3-galectin-9 pathway may play a role in chronic autoimmune diseases, such as multiple sclerosis. TIM-3 can promote clearance of apoptotic cells by binding phosphatidyl serine through its unique binding cleft.

Anti-TIM3 antibodies can promote antitumor immunity and suppress tumor growth. The current disclosure provides compositions and methods of cancer combination therapy. In some embodiments, the compositions and methods of the cancer combination therapy provided herein can include a PARP inhibitor and a TIM-3 inhibitory agent. In some embodiments, the PARP inhibitor is niraparib or pharmaceutically acceptable salts thereof. In some embodiments, the TIM-3 inhibitory agent can be a small molecule inhibitor. In some embodiments, the TIM-3 inhibitory agent can be an anti-TIM3 antibody or fragment thereof.

LAG-3

LAG-3 is upregulated following T-cell activation, and modulates T-cell function as well as T-cell homeostasis. The LAG-3/MHC class II interaction may play a role in down-regulating antigen-dependent stimulation of CD4+ T lymphocytes, higher expression of activation antigens such as CD25, and higher concentrations of cytokines such as interferon-gamma and interleukin-4. CD4+CD25+ regulatory T-cells (Treg) can also express LAG-3 upon activation and antibodies to LAG-3 inhibit suppression by induced Treg cells, both in vitro and in vivo, suggesting that LAG-3 contributes to the suppressor activity of Treg cells. Furthermore, LAG-3 can negatively regulate T-cell homeostasis by regulatory T cell-dependent and -independent mechanisms.

Subsets of conventional T-cells that are anergic or display impaired functions express LAG-3, and LAG-3+ T-cells are enriched at tumor sites and during chronic viral infections. In a self-tolerance/tumor mouse model where transgenic CD8+ T-cells were rendered unresponsive/anergic in vivo, LAG-3 blockade enhanced T-cell proliferation, T-cell recruitment and effector functions at the tumor site (Grosso et al., *J. Clin. Invest.,* 117: 3383-92 (2007)).

In addition, the interaction between LAG-3 and its major ligand, MHC class II, may play a role in modulating dendritic cell function (Andreae et al., *J Immunol.,* 168: 3874-3880, 2002). Recent preclinical studies have documented a role for LAG-3 in CD8+ T cell exhaustion (Blackburn et al., *Nat Immunol.,* 10: 29-37, 2009), and blockade of the LAG-3/MHC class II interaction using a LAG-3Ig fusion protein may be useful for cancer therapy.

The current disclosure provides compositions and methods of cancer combination therapy. In some embodiments, the compositions and methods of the cancer combination therapy provided herein can include a PARP inhibitor and a LAG-3 inhibitory agent. In some embodiments, the PARP inhibitor is niraparib or pharmaceutically acceptable salts thereof. In some embodiments, the LAG-3 inhibitory agent can be a small molecule inhibitor. In some embodiments, the LAG-3 inhibitory agent can be an anti-LAG-3 antibody or fragment thereof.

Indoleamine-Pyrrole 2,3-Dioxygenase (IDO)

IDO is an inducible enzyme that catalyzes the rating limiting step in tryptophan catabolism. This enzyme is overexpressed in response to IFN-γ in a variety of different malignancies. IDO can cause immunosuppression through breakdown of tryptophan in the tumor microenvironment and tumor-draining lymph nodes. The depletion of tryptophan and toxic catabolites can render effector T cells inactive and dendritic cells immunosuppressive. IDO inhibition can delay tumor growth, enhance dendritic cell vaccines, and synergize with chemotherapy through immune-mediated mechanisms. IDO inhibitory agents can include, but not limited to, d-1-methyl-tryptophan (d-1-MT), norharmane, rosmarinic acid, COX-2 inhibitors, 1-methyltryptophan, epacadostat and GDC-0919. IDO inhibitory agents can be anti-IDO antibodies.

The current disclosure provides methods and compositions of cancer combination therapy. In some embodiments, the combination therapy can include a PARP inhibitor and an IDO inhibitory agent. In some embodiments, the PARP inhibitor is niraparib or pharmaceutically acceptable salts thereof. In some embodiments, the IDO inhibitory agent can be a small molecule inhibitor. In some embodiments, the IDO inhibitory agent can be an anti-IDO antibody or fragment thereof.

Glucocorticoid-Induced TNFR-Related Protein (GITR)

Glucocorticoid-induced TNFR-related protein (GITR) is a member of the tumor necrosis factor receptor (TNFR) superfamily, is a key regulator in a multitude of immune functions. GITR is expressed in most immune cell types including T regulatory cells (Tregs), naïve T cells, natural killer cells (NKs), and at low levels in B cells, macrophages, and dendritic cells. GITR signaling is triggered by its ligand (GITRL), which is expressed in antigen-presenting cells and endothelial cells and is involved in regulating T cell receptor-mediated cell death. Upregulation of GITR signaling in $CD4^+$ and $CD8^+$ T cells causes enhanced T cell expansion and cytokine production.

In some embodiments, molecules which induce GITR signaling may be used to activate antigen-specific T cells. For example, administration of the GITR agonist DTA-1 in mice increases intratumor infiltration of $CD4^+$ and $CD8^+$ T cells. In addition to DTA-1, administration of the GITR agonists mGITRL and pGITRL (dimeric and pentameric versions of the GITR ligand, respectively), has been effective to induce tumor regression and activate $CD8^+$ cells in tumor microenvironments.

Angiogenesis Inhibitors

Tumor growth and metastasis depend on new growth in the vascular network supporting the tumor. Vascular Endothelial Growth Factor A (VEGF) is secreted by tumor cells and acts on endothelial cells to stimulate angiogenesis during tumor growth. Anti-angiogenic antibodies such as VEGF blockers (e.g., bevacizumab) can increase numbers of antigen-specific T cells in solid tumors and enhance the efficiency of immunotherapy. For example, combination treatment of bevacizumab with either atezolizumab (inhibiting PD-L1) or ipilimumab (inhibiting CTLA-4) increases the number of intratumoral $CD8^+$ cells. Other examples of VEGF blockers which may activate antigen-specific T cells in tumor microenvironments include pazopanib, sunitinib, sorafenib, axitinib, ponatinib, regorafenib, cabozantinib, vandetanib, ramucirumab, lenvatinib and ziv-aflibercept.

Other Agents

The present invention contemplates the use of any factor capable of activating or stimulating antigen-specific T cell activity in a tumor cell microenvironment. Further examples of agents which in some embodiments may be used to activate antigen-specific T cells (e.g., $CD4^+$ or $CD8^+$ cells) include flavonoids (e.g., flavonoid glycoside), lidocaine, lamotrigine, sulfamethoxazole, phenytoin, carbamazepine, sulfamethoxazole, phenytoin, allopurinol, paracetamol, mepivacaine, p-phenylenediamine, ciprofloxacin and moxifloxacin.

Combination Therapy of PARP Inhibitors and Antigen-Specific T Cell Activators

The current disclosure provides compositions and methods of cancer combination therapy involving a PARP inhibitor and an activator of antigen-specific T cells. In some embodiments, the compositions and methods of the cancer combination therapy provided herein can include niraparib and an agent which activates antigen-specific T cells in a tumor microenvironment. In some embodiments, the compositions and methods of the cancer combination therapy provided herein can include niraparib and at least one agent which activates antigen-specific T cells in a tumor microenvironment. The at least one agent which activates antigen-specific T cells can be small molecule inhibitors/agonists, proteins or protein fragments, antibodies, antibody fragments and/or polynucleotides. In some embodiments, the Treg-inhibiting agents can be recombinant proteins. In some embodiments, the Treg-inhibiting agents can be delivered by gene therapy.

In some embodiments, the agent that activates antigen-specific T cells can be a cytokine. In some embodiments, the agent that activates antigen-specific T cells can be an inhibitor of PD-1 signaling. In some embodiments, the agent that activates antigen-specific T cells can be an angiogenesis inhibitor such as a VEGF inhibitor. In some embodiments, the agent that activates antigen-specific T cells can be an agent that triggers GITR signaling. In some embodiments, the agent that activates antigen-specific T cells can be an agent that inhibits CTLA-4 signaling. In some embodiments, the agent that activates antigen-specific T cells can be any agent capable of activating $CD4^+$ and/or $CD8^+$ cells in a tumor microenvironment.

In some embodiments, the agent that activates antigen-specific T cells in a tumor microenvironment can be an agent selected from the group consisting of: pembrolizumab, nivolumab, PDR001, REGN2810 (SAR-439684), BGB-A317, BI 754091, IBI308, INCSHR-1210, JNJ-63723283, JS-001, MEDI0680 (AMP-514), MGA-012, PF-06801591, REGN-2810, TSR-042, PDR-001, camrelizumab (HR-301210), BCD-100, AGEN-2034, CS1001, Sym-021, LZMO09, KN-035, AB122, genolimzumab (CBT-501), AK 104, GLS-010, atezolizumab, durvalumab, avelumab, CX-072, FAZ053, LY3300054, PD-L1 millamolecule, BGB-A333, SHR-1316, CK-301, or derivatives thereof, LY3300054, DTA-1, mGITRL, pGITRL, ipilimumab, ipilimumab, interleukin-2 (IL-2), IL-1, IL-7, IL-15, IL-12, IL-18, interferon-α (IFN-α), CXCL16, bevacizumab, pazopanib, sunitinib, sorafenib, axitinib, ponatinib, regorafenib, cabozantinib, vandetanib, ramucirumab, lenvatinib, ziv-aflibercept, moxifloxacin, flavonoids (e.g., flavonoid glycoside), lidocaine, lamotrigine, sulfamethoxazole, phenytoin, carbamazepine, sulfamethoxazole, phenytoin, allopurinol, paracetamol, mepivacaine, p-phenylenediamine, ciprofloxacin and moxifloxacin.

Tumor-Associated Macrophages (TAMs)

While a few tumors may grow as cell suspensions, for example leukemia and ascites tumor, most tumors form into solid masses of tissues that can be mainly composed of malignant cells and stroma. The tumor stroma which can be largely produced from normal host tissue includes matrix components, blood vessels as well as inflammatory cells. Malignant cells may alter the properties their stroma by cell-to-cell contact, soluble factors and/or by modification of the extra-cellular matrix (ECM) in support of their growth. On the other hand, in response to malignant cells, the stromal cells can modify the phenotypes, invasiveness and metastatic capacity of tumor cells, typically promoting their progression. A vast diversity of molecules are produced by different cellular components within the complex tumor microenvironment such as cytokines, chemokines, growth factors and proteases, which may positively or negatively influence tumor survival and growth.

Tumor-associated macrophages (TAMs) can be the main population of inflammatory cells in tumor stroma. TAMs can be originated from peripheral blood monocytes in the blood circulation which can be recruited into the tumor mass by tumor-derived chemoattractants and then differentiated into tissue macrophages. TAMs generally may fail to express pro-inflammatory cytokines for T helper type 1 (Th1) responses but can be excellent producers of immunosuppressive cytokines for Th2 responses. As TAMs generally can exhibit low antigen-presenting and co-stimulating capacity, they ordinarily fail to activate T cell-mediated adaptive immunity. Therefore, unlike M1 macrophages, which can be highly microbicidal and tumoricidal, the M2-like TAMs can be immunosuppressive and facilitate tumor progression.

Macrophage Classification and the Heterogeneity of TAM Phenotypes

According to the different phenotypes and distinct patterns of gene expression, macrophages can be subdivided into type I and type II macrophages. The type I macrophages (M1) have a phenotypic pattern of high interleukin-12 (IL-12), low IL-10, or low IL-4/-13. The propensity of M1 can be increased in response to opsonized ligands and toll-like receptor (TLR) engagement. The typical type I macrophages can play an indispensable role in both innate and acquired immunity, and therefore they can have a proinflammatory characteristic. They can provide an in-front defense line against different kinds of pathogens and malignant cells via phagocytosis and/or induction of antibody-dependent cellular cytotoxicity. Activated macrophages can have the capability to recognize and bind to tumorigenic cells, a process that lead to the subsequent lysis or phagocytosis of tumor cells.

The type II macrophages (M2), which have the IL-10+/IL-12− phenotype, can have an immunosuppressive characteristic. TAMs can express typical M2 markers and have defective expression of some proinflammatory cytokines, such as IL-12, tumor necrosis factor-alpha (TNF-α), CC chemokine ligand 3 (CCL3), and IL-1 but high expression of IL-10, hence the TAMs can be M2-like. IL-12, typically produced by macrophages, is a cytokine in immune resistance against pathogens. IL-12 is known as a T cell stimulating factor, which can stimulate the growth and function of T cells. It can also facilitate the production of IFN-γ and TNF-α and alleviate IL-4-mediated suppression of IFN-γ. Therefore, lack of IL-12 production may result in dysfunction of the antitumor responses of macrophages. It was observed that the expression of IL-12 gene is partially controlled by members of nuclear factor-kappa B (NF-κB) family and failure to produce IL-12 may be associated with defective activation of p50/p65 NF-κB in TAMs. This defective activation of NF-κB in TAMs can also correlate with impaired expression of NF-κB-dependent inflammatory functions, for example, the expression of TNF-α, IL-1 and other cytotoxic mediators. Moreover, high level production of IL-10 triggered by CCL2 or other tumor-derived chemotactic factors (TDCFs) may play a role in defective IL-12 production. By interrupting the communication between tumor cells and their stroma, TAMs could be switched towards IFN-γ production and tumor rejection. Therapeutics targeted to block the production of IL-10 as well as other immunosuppressive cytokines in tumor sites may restore the antitumor functions of TAMs.

Macrophage Polarization and M2-Polarized TAMs

In response to different intercellular signals, macrophages can be polarized into different phenotypes. The type I macrophages which have the antitumor activity can be differentiated from monocytes exposed to certain factors such as granulocyte-macrophage colony-stimulating factor (GM-CSF), IFN-γ, LPS and some bacterial products; whereas macrophage colony-stimulating factor (M-CSF), IL-4/-13/-10 and some immunosuppressive agents trigger macrophages to differentiate toward type II macrophages. Treatment of monocytes with IFN-γ alone or in combination with TNF-α, GM-CSF or PPD, before/after co-cultured with tumor (HPC-4) cells can enhance the de novo production of molecular factors related to antitumor activity of macrophages. The activation of NF-κB turns on the inflammatory repertoire of macrophages, leading to the expression of proinflammatory cytokines. Defective NF-κB activation could inhibit the transcription of some key cytokines related to M1 phenotypes and the production of cytotoxic mediators. As an upstream component of NF-κB activation, TLR/IL-1R signaling may also play a role in regulating macrophage polarization. Additionally, the Tie-2/Ang-2 pathway, the TRIF/TBK1/IRF3 pathway, and hypoxia-induced pathway can be possible pathways in regulating the "shift" in macrophage phenotypes.

TAMs can be triggered into M2-like phenotypes by tumor-derived factors, such as cytokines, growth factors, chemotactic molecules and proteases which may either up-regulate or down-regulate the expression of macrophage effector molecules, thus influence the functions of macrophages. Many tumor-derived molecules can deactivate or suppress the cytotoxic activity of TAMs, including IL-4, IL-6, IL-10, macrophage-derived chemotactic factor (MDF), transforming growth factor beta1 (TGF-β1), prostaglandin E2 (PGE2), and M-CSF. One of the players in the regulation of macrophage infiltration can be monocyte chemotactic protein-1 (MCP-1/CCL2) and related CC chemokines. Accumulation of TAMs in primary tumors can be correlated with the level of CCL2 expression. CCL2 has been shown to be produced by a variety of human tumors, such as melanoma, malignant glioma, ovarian cancer and meningioma. MCP-2 and MCP-3, also known as CCL8 and CCL7, are the other two members of the CCL2 family which were isolated from tumor cell lines. In addition, breast carcinoma at advanced stage was reported to be associated with increased expression of CCL5, and CCL5 receptor (CCR5) was detected on TAMs. CCL5 may play a role in macrophage migration, tumor progression, and protumorigenic activity.

TAMs can promote tumor angiogenesis by secreting a vast diversity of factors, including vascular endothelial growth factor (VEGF), granulocyte colony-stimulating factor (GCSF), basic fibroblasts growth factor (bFGF), insulin-like growth factor-I (IGF-I), platelet derived growth factor (PDGF), transforming growth factor-β (TGF-β), tumor necrosis factor-α (TNF-α), IL-1, IL-6, IL-8, substance P, prostaglandins and other kinds of monokines. Proteolytic enzymes, including matrix metalloproteinases (MMPs), which may be one of the key molecular factors in angiogenesis, can be secreted by TAMs. Synthetic inhibitors against MMPs (MMPIs) have been developed and put into clinical trials as anti-cancer therapeutics. Moreover, TNF-α can be largely produced by TAMs and is also a hypoxia-inducible pro-angiogenic cytokines. TNF-α can initiate a cascade of signal transductions upon its secretion, leading to the production of other factors which in turn function positively on angiogenesis.

TAM-Targeted Antitumor Strategies

The function of TAMs can depend on their accumulation and activation in tumor tissues, therefore, TAM-targeted anti-tumor approaches can based on the following four strategies: 1) inhibiting macrophage recruitment; 2) suppressing TAM survival; 3) enhancing M1 tumoricidal activity of TAMs; and 4) blocking M2 tumor-promoting activity of TAMs.

Chemoattractants released by tumor cells can facilitate the recruitment of macrophages into tumor tissues. These chemoattractants can include, but not limited to, CCL2, macrophage colony-stimulating factor (M-CSF, or also known as colony stimulating factor 1, CSF-1), CCL5, C—X—C motif chemokine ligand-12 (CXCL-12) and vascular endothelial growth factor (VEGF). Binding agents targeting these chemoattractants or neutralizing their corresponding receptors can be used to inhibit the recruitment of macrophages. For example, binding agents of CCL2/CCR2 can include pharmaceutical inhibitors (e.g., trabectedin, RS102895, and PF-04136309) and antibodies (e.g., CNT0888 and MLN1202). Anti-IL6 antibody siltuximab may also inhibit macrophage infiltration in tumour tissue via declining the plasma level of some chemoattractants such as CCL2, VEGF and CXCL-12. Binding agents of M-CSF/M-CSFR can include anti-M-CSFR (or anti-CSF-1R) antibodies JNJ-28312141, GW2580, IMC-CS4 (LY3022855), emactuzumab, AMG820, MCS110, small molecule inhibitors pexidartinib, PLX7846, linifanib, OSI-930, CEP-32496, ARRY-382, and JNJ-40346527. Other anti-M-CSF/M-CSFR agents include PLX3397, PLX6134, PD-0360324, or FPA008. Inhibitors of other chemoattractants (e.g., VEGF, CXCL-12 and CCL5) and their receptors can be useful for TAM depletion and tumor rejection. In addition, inhibitors of hypoxia-inducible factors (HIFs), which are transcriptional activators for VEGF and CXCR4 (encoding for CXCL-12 receptor) genes, may be anti-tumor candidates for their potential to inhibitor angiogenesis and macrophage recruitment.

To suppress TAM survival, two approaches can be used. One can be to directly induce macrophage apoptosis using chemical reagents, immunotoxin-conjugated monoclonal antibodies or attenuated bacteria; the other can be to trigger the immune cells, for example T lymphocytes, to recognize and abrogate TAMs. Bisphosphonates (e.g., clodronate, zoledronic acid and dichloromethylene bisphosphonate), generally packed in liposomes, can be used for macrophage depletion by inducing apoptosis. Trabectedin can activate caspase-8-dependent apoptosis and selectively deplete monocytes including TAMs. Dasatinib, a Src kinase inhibitor, can reduce MMP9+ macrophage density and inhibit MMP9 expression in the tumor environment. To deplete TAMs by targeting their surface molecules with immuno-toxin-conjugated agents can be another approach for tumor therapy. The surface proteins of TAMs that may be targets can include scavenger receptor-A, CD52 and folate receptor β (FRβ). Bacteria can also take macrophages as targets. For example, Shigella flexneri infection could selectively induce the apoptosis of macrophages, and a single injection of an attenuated strain of Shigella flexneri to tumor-bearing mice resulted in the apoptosis of TAMs, followed by a 74% reduction in size of tumors. Other bacteria that can be used for TAM-targeted immunotherapy include, but not limited to, Salmonella typhimurium, Listeria monocytogens, Chlamydia psittaci and Legionella pneumophila. As mentioned above herein, another available approach for TAM suppression can be to evoke acquired immune responses, in which cytotoxic T lymphocytes can act as the scavengers of TAMs because they can naturally target the membrane molecules of macrophages. In other words, up-regulating the membrane molecules that could be recognized by T cells in TAMs can be a method of TAM depletion. One such molecule is legumain, a lysosomal protease highly expressed in many human tumors and M2-like TAMs. A legumain based DNA vaccine can activate dendritic cells, which then triggered multi-step reactions including the antigen presenting, co-stimulation of cytotoxic CD8+ T cells and the specific abrogation of legumain-expressing TAMs. Another membrane protein involved in T-cell-mediated TAM depletion can be CD1d, a target of Vα24-invariant natural killer T (NKT) cells. Agents that can promote the expression of CD1d in TAMs may improve the tumoricidal function of NKT cells. One such agent can be retinoic acid, which can strongly up-regulate the CD1d expression in macrophages and is now used as a standard therapeutic drug for high-risk neuroblastoma in clinic.

To enhance M1 tumoricidal activity of TAMs, TAMs can be re-polarized from M2 type to M1 type. Manipulating transcription factors and their up-/down-stream regulators can contribute to targeted tumor therapy. These transcription factors can include M1-promoting modulators STAT1 and NF-κ3 (p50p65 heterodimer). NF-κB activating agents can include the agonists of Toll-like receptor (TLRs), anti-CD40 mAb and anti-IL-10R mAb. The TLR agonists can be diverse, including PolyI:C (for TLR3), lipopolysaccharide (LPS) and monophosphoryl A (for TLR4), imiquimod and R-848 (for TLR7), and CpG-oligodeoxynucleotide (CpG-ODN, for TLR9). In addition, anti-CD40 mAb may be used to promote TLR9 to respond to CpG-ODN. Agonists of STAT1 can include IFN-α (FDA approved), IFN-β (FDA approved) and IFN-γ. Agonistic anti-CD40 antibodies can include CP-870893 and RO7009789. In addition, other factors such as GM-CSF, IL-12, IL-2 and IL-15 may be used to induce M1 function. These factors may be delivered into a subject by recombinant proteins or gene therapy. A peptide drug, thymosin-α1 (Tα1) can also be used to induce M1 function. Tumor cells can express CD47, a 'don't eat me' signal that, via interaction with macrophage surface receptor SIRPα can prevent phagocytosis by macrophages. Thus, interference with the SIRPα-CD47 pathway, for example, using antagonistic antibodies, can activate macrophage-mediated antibody-dependent cellular phagocytosis (ADCP), which subsequently results in functional skewing of macrophages in an M1 direction that is associated with antitumor activity. CD47 antagonists can include anti-CD47 antibodies Hu5F9-G4 and CC-90002, and CD47-Fc fusion protein TTI-621. Moreover, B cell-macrophage interactions can promote PI3Kγ- and Bruton tyrosine kinase (BTK)-dependent macrophage M2 polarization. Inhibitors of Bruton tyrosine kinase, such as ibrutinib, can reprogram TAM toward M1 phenotype. Vitamin-D-binding protein (macrophage activating factor), for example EF-022, can also promote tumoricidal activity of macrophage and prevent angiogenesis in tumors.

To block M2 tumor-promoting activity of TAMs, M2-promoting transcription factors STAT3 and STAT6 can be inhibited. STAT3 inhibitors can include WP1066, tyrosine kinase inhibitors sunitinib and sorafenib, STA-21, IS3 295 and S31-M2001. STAT6 inhibitors can include AS1517499, leflunomide and TMC-264. Several up-/down-stream mediators of STAT6 can act as modulators of TAM function. These modulators include phosphatidylinositol 3-kinase (PI3K), Src homology 2-containing inositol-5'-phosphatase (SHIP), Krüppel-like factor 4 (KLF4) and c-Myc. Other proteins that may promote M2 function and thus can be targeted for cancer therapy include, but not limited to, peroxisome proliferator-activated receptor (PPARs), HIFs, Ets family member 2 (Ets2), Decoy receptor (DcR3) and mammalian target of rapamycin (mTOR). Several antitumour drugs that can suppress M2 macrophages can include histidine-rich glycoprotein (HRG), copper chelate (CuNG), 5,6-dimethylxanthenone-4-acetic acid (MDXAA), vadimezan (ASA404), cisplatin, silibinin, CNI-1493, and proton pump inhibitor pantoprazole (PPZ). Other agents that can re-polarize M2-like TAMs include, but not limited to, anti-IL-1α antibody xilonix.

Combination Therapy of PARP Inhibitors and TAM-Targeting Agents

A TAM-targeting agent or TAM inhibitory agent can be used interchangeably herein. A TAM inhibitory agent can be an agent that 1) can inhibit macrophage recruitment; 2) can suppress TAM survival; 3) can enhance M1 tumoricidal activity of TAMs; and 4) can block M2 tumor-promoting activity of TAMs. A TAM inhibitory agent can decrease or eliminate the population of TAM. A TAM inhibitory agent can also regulate the function of TAM.

The current disclosure provides compositions and methods of cancer combination therapy of a PARP inhibitor and a TAM-targeting agent. In some embodiments, the compositions and methods of the cancer combination therapy provided herein can include niraparib and pharmaceutically acceptable salts thereof and a TAM-targeting agent. In some embodiments, the compositions and methods of the cancer combination therapy provided herein can include niraparib and at least one TAM-targeting agent. The TAM-targeting agents can be small molecule inhibitors/agonists, proteins or protein fragments, antibodies or antibody fragments, or bacteria. In some embodiments, the TAM-targeting agents can be recombinant proteins. In some embodiments, the TAM-targeting agents can be delivered by gene therapy.

In some embodiments, the TAM-targeting agents can be agents that inhibit recruitment of macrophages. In some embodiments, the TAM-targeting agent can be an inhibitor of a chemoattractant selected from the group consisting of CCL2, M-CSF (CSF-1), CCL5, CXCL-12 and VEGF. In some embodiments, the TAM-targeting agent can be an antibody targeting M-CSF/M-CSFR (or CSF-1/CSF-1R). In some embodiments, the compositions and methods of the cancer combination therapy provided herein can include niraparib and at least one TAM-targeting agent selected from the group consisting of trabectedin, RS102895, PF-04136309, CNT0888, MLN1202, siltuximab, JNJ-28312141, GW2580, IMC-CS4 (LY3022855), emactuzumab, AMG820, pexidartinib, linifanib, OSI-930, CEP-32496, PLX7846, ARRY-382, JNJ-40346527, MCS110, PLX3397, PLX6134, PD-0360324, FPA008, and any combinations thereof.

In some embodiments, the TAM-targeting agents can be agents that suppress the M2-like TAM survival. In some embodiments, the TAM-targeting agents can be chemical reagents, immunotoxin-conjugated monoclonal antibodies or attenuated bacteria that directly induce apoptosis of TAMs. In some embodiments, the TAM-targeting agents can be agents that can trigger immune cells to abrogate TAMs. In some embodiments, the TAM-targeting agents can be bisphosphonates. In some embodiments, the compositions and methods of the cancer combination therapy provided herein can include niraparib and at least one TAM-targeting agent selected from the group consisting of clodronate, zoledronic acid, dichloromethylene bisphosphonate, trabectedin, dasatinib, retinoic acid, and any combinations thereof. In some embodiments, the compositions and methods of the cancer combination therapy provided herein can include niraparib and at least one attenuated bacteria selected from the group consisting of *Shigella flexneri, Salmonella typhimurium, Listeria monocytogens, Chlamydia psittaci, Legionella pneumophila*, and any combinations thereof.

In some embodiments, the TAM-targeting agents can be agents that enhance the tumoricidal activity of M1 type macrophages or repolarizing the M2 type macrophages into M1 type. In some embodiments, the TAM-targeting agents can be NF-κB activating agents. In some other embodiments, the TAM-targeting agents can be STAT1 activating agents. In some embodiments, the TAM-targeting agents can include the agonists of Toll-like receptor (TLRs), anti-CD40 mAb and anti-IL-10R mAb. In some embodiments, the TAM-targeting agents can be PolyI:C (for TLR3), lipopolysaccharide (LPS) or monophosphoryl A (for TLR4), imiquimod or R-848 (for TLR7), or CpG-oligodeoxynucleotide (CpG-ODN, for TLR9), or any combinations thereof. In some embodiments, the TAM-targeting agents can be IFN-α, IFN-β, IFN-γ, GM-CSF, IL-12, IL-2, IL-15, or any combinations thereof. In some embodiments, the compositions and methods of the cancer combination therapy provided herein can include niraparib and at least one TAM-targeting agent selected from the group consisting of anti-CD40 mAb, anti-IL-10R mAb, CD47 antagonists (e.g., anti-CD47 antibodies Hu5F9-G4 and CC-90002, and CD47-Fc fusion protein TTI-621), PolyI:C, LPS, monophosphoryl A, imiquimod, R-848, CpG-ODN, IFN-α, IFN-β, IFN-γ, GM-CSF, IL-12, IL-2, IL-15, Tα1, ibrutinib, EF-022 and any combinations thereof.

In some embodiments, the TAM-targeting agents can be agents that block M2 tumor-promoting activity of TAMs. In some embodiments, the TAM-targeting agents can include inhibitors of STAT3 or STAT6. In some embodiments, the TAM-targeting agents can include other M2 modulators, including PI3K, SHIP, KLF4, c-Myc, PPARs, HIFs, Ets2, DcR3, and mTOR. In some embodiments, the compositions and methods of the cancer combination therapy provided herein can include niraparib and at least one TAM-targeting agent selected from the group consisting of WP1066, sunitinib, sorafenib, STA-21, IS3 295, 53I-M2001, AS1517499, leflunomide, TMC-264, histidine-rich glycoprotein (HRG), copper chelate (CuNG), 5,6-dimethylxanthenone-4-acetic acid (MDXAA), vadimezan (ASA404), cisplatin, silibinin, proton pump inhibitor pantoprazole (PPZ), CNI-1493, anti-IL-la antibody xilonix, EF-022 and any combinations thereof.

Regulatory T Cells

Forkhead box protein 3 (Foxp3)-expressing regulatory T cells (Treg cells) can function in the regulation of immune responses and in the maintenance of immunological self-tolerance. These cells can be therapeutic targets for autoimmune diseases and cancer. Treg cells can be characterized by the expression of the high-affinity interleukin-2 (IL-2) receptor α-chain (IL-2Rα; also known as CD25) and the X-linked gene Foxp3, encoding the transcription factor Foxp3, which serves as a lineage specification factor for the development and function of $CD4^+$ CD25+ Treg cells.

Treg can infiltrate tumor tissues, and Treg cell-mediated suppression of tumor-associated antigens can be a potential mechanism to explain the failure of antitumor immunity. Tumor-induced expansion of Treg cells can be an obstacle to successful cancer immunotherapy. Treg cells can selectively interfere with the release of cytolytic granules by cytotoxic T lymphocytes (CTLs) in a reversible and TGFβ-dependent manner, thereby attenuating CTL-mediated cytotoxicity without detectably affecting CTL priming or differentiation. Local or systemic interference with suppressor pathways of CTL activity, such as cytokines, Toll-like receptor agonists, or Treg cell depletion, may be effective in tumor therapy.

One approach used to inhibit Treg cells can be Treg depletion. Some conventional chemotherapy agents can affect adaptive immune system, resulting in the inhibition of Treg function or viability. For example, these agents can include, but not limited to, cyclophosphamide and paclitaxel. Angiogenesis inhibition can overcome various immunosuppressive networks including Treg. The immunogenic effects of more specific molecularly targeted therapeutic anticancer agents can also impair Treg functions. These targeted therapeutic anticancer agents include some tyrosine kinase inhibitors, but not limited to, imatinib (Gleevec; Novartis), sunitinib (Sutent; Pfizer), sorafenib (Nexavar; Bayer/Onyx), dasatinib, and temozolomide. Some of these tyrosine inhibitors can block STAT3 and STAT5 signaling and decrease Treg cell frequency, or limit infiltration by Treg cells while inhibiting STAT3 activity. Strategies for Treg cell depletion can include agents that target IL-2R which is unregulated in Treg cells. These agents can include anti-CD25 monoclonal antibody daclizumab (Zenapax; PDL BioPharma) and denileukin diftitox (Ontak; Esai).

A second approach to inhibit Treg cells can include the targeting of molecules that are involved in Treg cell migration. Treg cells from cancer patients, as compared to heathy subjects, can be characterized by a distinct expression profile of chemokine receptors, such as CCR4, CXCR4, and CCR5, which can facilitate their migration into tumors in response to the corresponding chemokine ligands derived from tumor microenvironment. Treg cell trafficking to tumors can be triggered by a cohort of tumor-associated chemokines or hypoxia-induced factors, including CCL22, CCL17, CXCL12, CCL28, and VEGF. CC motif chemokine 22 (CCL22) blockage can reduce Treg cell-mediated tumor trafficking. Agents that block CCL22 can include, but are not limited to, casuarinin and fucoidan. CXCR4 and CXCL12 can contribute to Treg cell migration to the bone marrow. Antagonists of CXCR4, for example AMD3100, can promote antitumor immunity. Antagonists of CCR4, for example anti-CCR4 antibody mogamulizumab, can prevent the interaction of CCL22/CCL17 with their receptor. Other chemokine receptors such as CCR7 may also play a role in Treg migration.

Another approach to inhibit Treg cells can include using antibodies to target molecules constitutively expressed by Treg leading to their functional inhibition. Ipilimumab and tremelimumab, antibodies that are specific for cytotoxic T lymphocyte antigen 4 (CTLA4) can block an inhibitory signal for activated T cells, thereby bolstering T cell responses and potentiating tumor destruction. The mechanism of CTLA4-specific antibodies may be inhibiting Treg-dependent immune suppression. Adenosine $A_{2A}$ receptor can inhibit T cell responses in part by upregulating Foxp3 expression in $CD4^+$ T cells. Engagement of adenosine $A_{2A}$ receptor by adenosine can result in Treg cell induction which may lead to self-amplifying loop within the tumor. Inhibition of adenosine $A_{2A}$ receptor can be achieved using antibodies to block adenosine or using adenosine analogues. GITR can be constitutively expressed by Treg, but it is also detected, albeit at lower levels, on $CD4^+$ and $CD8^+$ effector T cells. Stimulation by agonistic antibodies to either GITR or GITR ligand can have a dual effect leading to suppression of Treg activity and enhanced proliferation of effector T cells and possible resistance to Treg-mediated suppression. OX40, a costimulatory molecule of the TNF receptor family, can be constitutively expressed on Treg and transiently expressed on activated T cells. Activation of OX40 signaling by an agonistic anti-OX40 mAb can inhibit the suppressive activity of Treg.

Treg can express various TLRs and notably high levels of TLR4, TLR5, TLR7 and TLR8. TLR 8 activation by its natural or synthetic ligands can inhibit Treg function and enhance in vivo tumor immunity. Appropriate TLR stimulation might therefore be an important tool for vaccination. Treg can produce adenosine via catabolism of adenine nucleotides (ATP, ADP and AMP) by extracellular ecto-nucleotidases, CD39 and CD73. Adenosine is a major immunosuppressive factor that may participate in the immunosuppressive activity of Foxp3+ T cells. Low molecular weight inhibitors and adenosine receptor antagonists can be used to block adenosine-mediated immune suppression. Exemplary adenosine receptor antagonists can include caffeine, theophylline, theobromine, and 8-phenylxanthines. Inhibition of CD39 with enzymatic inhibitors can block Treg function and improve the effects of chemotherapy. In addition, a peptide inhibitor of Foxp3 (Peptide P60) can impair Treg activity and improve vaccine efficacy.

Combination Therapy of PARP Inhibitors and Treg-Inhibiting Agents

A Treg inhibitory agent or Treg inhibitor or Treg-inhibiting agents can refer to an agent that: (1) inhibits or decreases the activity or function of a regulatory T cell, (2) decreases the population of regulatory T cells in a subject (in one embodiment, the decrease can be temporary, for example, for a few hours, a day, a few days, a week, or a few weeks), or (3) substantially ablates or eliminates the population of regulatory T cells in a subject (in one embodiment, the ablation or elimination can be temporary, for example, for a few hours, a day, a few days, a week, or a few weeks). A Treg inhibitor can decrease the suppression of immune system activation and can decrease prevention of self-reactivity. Exemplary Treg inhibitors may include, but are not limited to, a compound, antibody, fragment of an antibody, or chemical that targets a Treg cell surface marker (such as CD25, CD4, CD28, CD38, CD62L (selectin), OX-40 ligand (OX-40L), CTLA4, CCR4, CCR8, FOXP3, LAG3, CD103, NRP-1, glucocorticoid-induced TNF receptor (GITR), galectin-1, TNFR2, or TGF-βR1). In certain embodiments, a Treg inhibitor targets a Treg cell surface marker that is involved in Treg activation such that the Treg inhibitor prevents Treg activation. A Treg inhibitor may include, but is not limited to, antibodies, fusion proteins, ONTAK, HuMax-Tac, Zenapax, or MDX-010, aptamers, siRNA, ribozymes, antisense oligonucleotides, and the like. The administration of a Treg inhibitor or derivatives thereof can block the action of its target, such as a Treg cell surface marker. A Treg inhibitor can have an attached toxic moiety such that upon internalization of the inhibitor, the attached toxic moiety can kill the T regulatory cell.

The current disclosure provides compositions and methods of cancer combination therapy of a PARP inhibitor and a Treg-inhibiting agent. In some embodiments, the compositions and methods of the cancer combination therapy provided herein can include niraparib and pharmaceutically acceptable salts thereof and a Treg-inhibiting agent. In some embodiments, the compositions and methods of the cancer combination therapy provided herein can include niraparib and at least one Treg-inhibiting agent. The Treg-inhibiting agents can be small molecule inhibitors/agonists, proteins or protein fragments, antibodies or antibody fragments. In some embodiments, the Treg-inhibiting agents can be recombinant proteins. In some embodiments, the Treg-inhibiting agents can be delivered by gene therapy.

In some embodiments, the Treg-inhibiting agents can be agents that can lead to Treg cell death. In some embodiments, the Treg-inhibiting agents can be chemotherapy agents. In some embodiments, the Treg-inhibiting agents can be angiogenesis inhibitors. In some embodiments, the Treg-inhibiting agents can be tyrosine kinase inhibitors. In some embodiments, the Treg-inhibiting agents can be STAT3 or STATS inhibitors. In some embodiments, the Treg-inhibiting agents can be the agents selected from the group consisting of cyclophosphamide, paclitaxel, imatinib (Gleevec; Novartis), sunitinib (Sutent; Pfizer), sorafenib (Nexavar; Bayer/Onyx), dasatinib, temozolomide, daclizumab (Zenapax; PDL BioPharma), denileukin diftitox (Ontak; Esai), and any combinations thereof.

In some embodiments, the Treg-inhibiting agents can be agents that inhibit Treg migration. In some embodiments, the Treg-inhibiting agents can be CC motif chemokine 22 (CCL22) inhibitors. In some embodiments, the Treg-inhibiting agents can be CCR4, CCR5, or CCR7 inhibitors. In some embodiments, the Treg-inhibiting agents can be antagonists of CXCR4. In some embodiments, the Treg-inhibiting agents can be agents selected from the group consisting of AMD3100 or mogamulizumab, casuarinin, fucoidan, and any combinations thereof.

In some embodiments, the Treg-inhibiting agents can be agents that block Treg function. In some embodiments, the Treg-inhibiting agents can be antibodies that target the constitutively expressed molecules of Treg. In some embodiments, the Treg-inhibiting agents can be antibodies against cytotoxic T lymphocyte antigen 4 (CTLA4), such as ipilimumab and tremelimumab. In some embodiments, the Treg-inhibiting agents can be the agents that inhibit adenosine $A_{2A}$ receptor. In some embodiments, the Treg-inhibiting agents can be antibodies that block adenosine or can be adenosine analogues. In some embodiments, the Treg-inhibiting agents can be immune agonists, including anti-CTLA4, anti-OX40, or anti-GITR antibodies. In some embodiments, the Treg-inhibiting agent can be a peptide inhibitor of Foxp3 Peptide P60.

Other Combination Therapies

Therapeutic methods of the invention can be combined with additional immunotherapies and therapies. For example, when used for treating cancer, inhibitors of the invention can be used in combination with conventional cancer therapies, such as, e.g., surgery, radiotherapy, chemotherapy or combinations thereof, depending on type of the tumor, patient condition, other health issues, and a variety of factors. In certain aspects, other therapeutic agents useful for combination cancer therapy with the inhibitors of the invention include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the inhibitors of the invention can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Non-limiting examples of chemotherapeutic compounds which can be used in combination treatments of the present invention include, for example, aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hex amethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

Pharmacokinetics

In some embodiments patients may be evaluated for pharmacokinetics information. Pharmacokinetic data can provide insight regarding the fate of a given drug (e.g., a therapeutic agent) from administration to elimination from the human body.

Pharmacokinetic data can be obtained by known techniques in the art. Due to the inherent variation in pharmacokinetic and pharmacodynamic parameters of drug metabolism in human subjects, appropriate pharmacokinetic and pharmacodynamic profile components describing a particular composition can vary. Typically, pharmacokinetic and pharmacodynamic profiles are based on the determination of the mean parameters of a group of subjects. The group of subjects includes any reasonable number of subjects suitable for determining a representative mean, for example, 5 subjects, 10 subjects, 16 subjects, 20 subjects, 25 subjects, 30 subjects, 35 subjects, or more. The mean is determined by calculating the average of all subject's measurements for each parameter measured.

In some embodiments, a patient population includes one or more subjects ("a population of subjects") suffering from metastatic disease.

In some embodiments, a patient population includes one or more subjects that is suffering from or susceptible to cancer. In some embodiments, a patient population includes one or more subjects (e.g., comprises or consists of subjects) suffering from cancer. For example, in some embodiments, a patient population suffering from cancer may have previously been treated with a prior therapy, for example, radiation and/or chemotherapy.

In some embodiments, the pharmacokinetic parameter(s) can be any parameters suitable for describing the present composition.

General Protocol for Dosing

As described herein, provided methods comprise administering a therapy that inhibits PARP and a therapy that regulates activity in the tumor microenvironment (e.g., T cell activity and/or infiltration of T cells into the tumor environment) in combination to a patient, a subject, or a population of subjects according to a regimen that achieves a therapeutic effect.

In some embodiments, administration "in combination" includes administration of one or more doses of an agent that inhibits PARP (e.g., niraparib) before, during, or after administration of one or more doses of an agent that enhances activity in the tumor microenvironment. In some embodiments, an agent that inhibits PARP (e.g., niraparib) and an agent that regulates activity in the tumor microenvironment are administered in overlapping regimens. In some embodiments, an agent that inhibits PARP (e.g., niraparib) is administered simultaneously or sequentially to an agent that enhances activity in the tumor microenvironment.

The number of times a composition is administered to an individual in need thereof depends on the discretion of a medical professional, the disorder, the severity of the disorder, and the individual's response to the formulation. In some embodiments, a composition disclosed herein is administered once to an individual in need thereof with a mild acute condition. In some embodiments, a composition disclosed herein is administered more than once to an individual in need thereof with a moderate or severe acute condition. In the case wherein the patient's condition does not improve, upon the doctor's discretion the administration of a combination drug product described herein may be administered chronically, that is, for an extended period of time, including throughout the duration of the patient's life in order to ameliorate or otherwise control or limit the symptoms of the patient's disease or condition.

Indications Suitable for Treatment

Any subject having cancer, including breast cancer, ovarian cancer, cervical cancer, epithelial ovarian cancer, fallopian tube cancer, primary peritoneal cancer, endometrial cancer, prostate cancer, testicular cancer, pancreatic cancer, esophageal cancer, head and neck cancer, gastric cancer, bladder cancer, lung cancer (e.g., adenocarcinoma, NSCLC and SCLC), bone cancer (e.g., osteosarcoma), colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma (e.g., liposarcoma), bladder cancer, liver cancer (e.g., hepatocellular carcinoma), kidney cancer (e.g., renal cell carcinoma), myeloid disorders (e.g., AML, CML, myelodysplastic syndrome and promyelocytic leukemia), and lymphoid disorders (e.g., leukemia, multiple myeloma, mantle cell lymphoma, ALL, CLL, B-cell lymphoma, T-cell lymphoma, Hodgkin's lymphoma, non-Hodgkin's lymphoma, hairy cell lymphoma) may be treated with compounds and methods described herein.

In some embodiments, the methods of the invention treat subjects with a pediatric cancer. Exemplary pediatric cancers include, but are not limited to adrenocortical carcinoma, astrocytoma, atypical teratoid rhabdoid tumor, brain tumors, chondroblastoma, choroid plexus tumor, craniopharynglioma, desmoid tumor, dysembryplastic neuroepithelial tumor (DNT), ependymoma, fibrosarcoma, germ cell tumor of the brain, glioblastoma multiforme, diffuse pontine glioma, low grade glioma, gliomatosis cerebri, hepatoblastoma, histiocytosis, kidney tumor, acute lymphoblastic leukemia (ALL), acute myeloid leukemia (AML), chronic myelogenous leukemia (CML), liposarcoma, liver cancer, Burkitt lymphoma, Hodgkin lymphoma, non-Hodgkin lymphoma, malignant fibrous histiocytoma, melanoma, myelodysplastic syndrome, nephroblastoma, neuroblastoma, neurofibrosarcoma, osteosarcoma, pilocytic astrocytoma, retinoblastoma, rhabdoid tumor of the kidney, rhabdomyosarcoma, Ewing sarcoma, soft tissue sarcoma, synovial sarcoma, spinal cord tumor and Wilm's tumor.

EXAMPLES

The following examples are provided to illustrate, but not limit the claimed invention.

Example 1—Effects of an Agent that Inhibits PARP on the Tumor Microenvironment

This example describes the effects of treatment with an agent that inhibits PARP signaling on tumor microenvironment in a mouse model of colorectal cancer. 50 mg/kg of niraparib or vehicle (0.5% methylcellulose) was orally administered once daily for 21 days to C57BL/6 mice inoculated with primary Murine skin cancer model mSK6005 fragment developed from $Apc^{Min}$/J heterozygous background. Formalin-fixed, paraffin-embedded (FFPE) blocks were prepared from tumor samples collected from the mice. Immunohistochemistry (IHC) staining was performed on FFPE samples to assess expression of various markers for immune response in the tumor samples. Five fields in each staining, without necrosis, were randomly selected and imaged at 20× magnification.

All the images were analyzed with Image J software. For CD4, CD8, and FoxP3 IHC, positive cells were counted and the average of 5 fields positive cell numbers was taken as the score value of each case. For Iba1 IHC, the percentage of Iba1 positive expression area or mean gray was measured and taken as the score value of each case. The percentages of tumor cells at different intensity levels were evaluated according to the calculation below.

Total Score=(% at 0)×0+(% at 1)×1+(% at 2)×2+(% at 3)×3

Figure 1B:
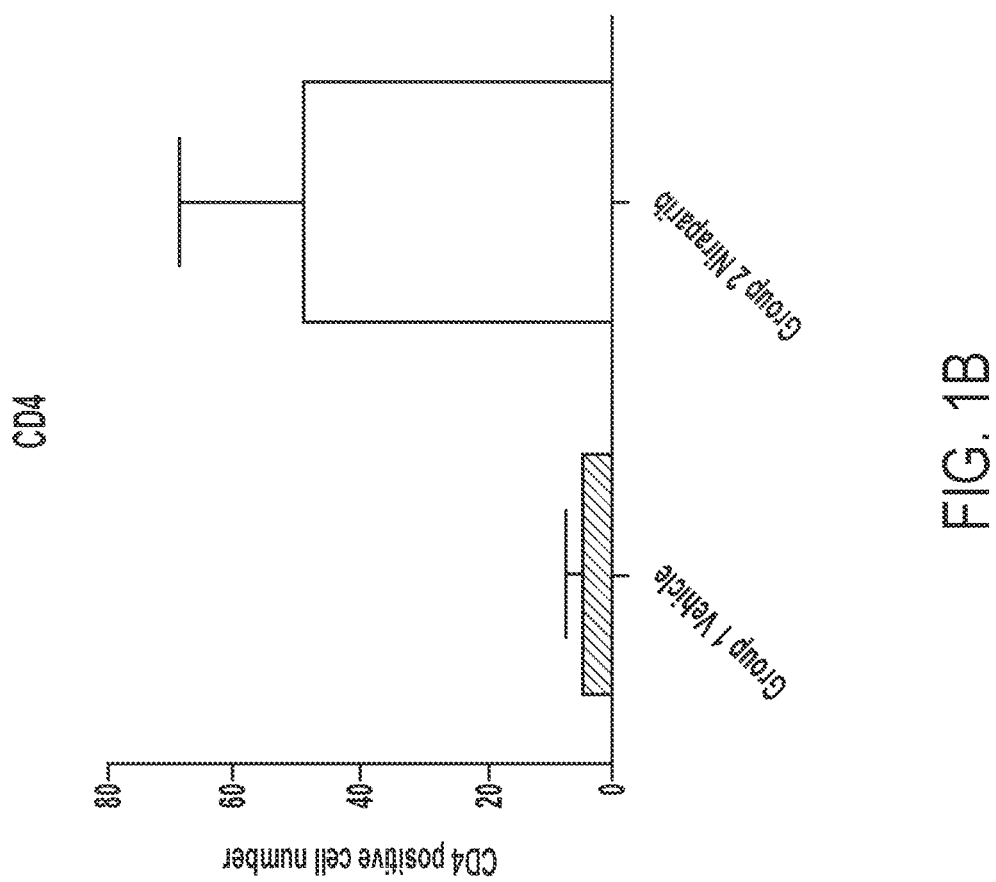
FIG. 1B depicts quantification of CD4 IHC staining images showing CD4 positive cell numbers in vehicle or niraparib treated mice.
Figure 2A:
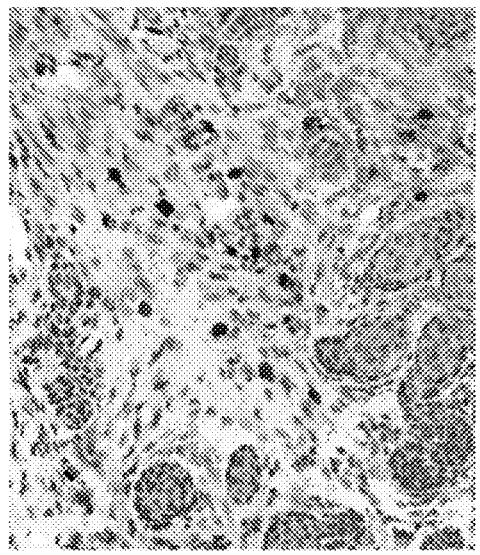
FIG. 2A depicts CD8 IHC staining on tumor samples developed from $Apc^{Min}$/J heterozygous background upon vehicle or niraparib treatment.
Figure 2A:
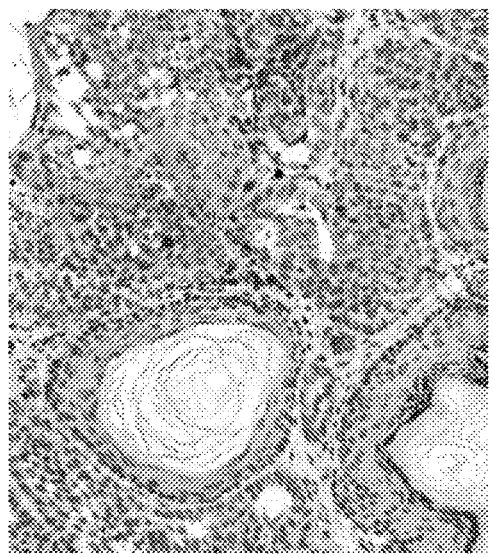
Figure 2B:
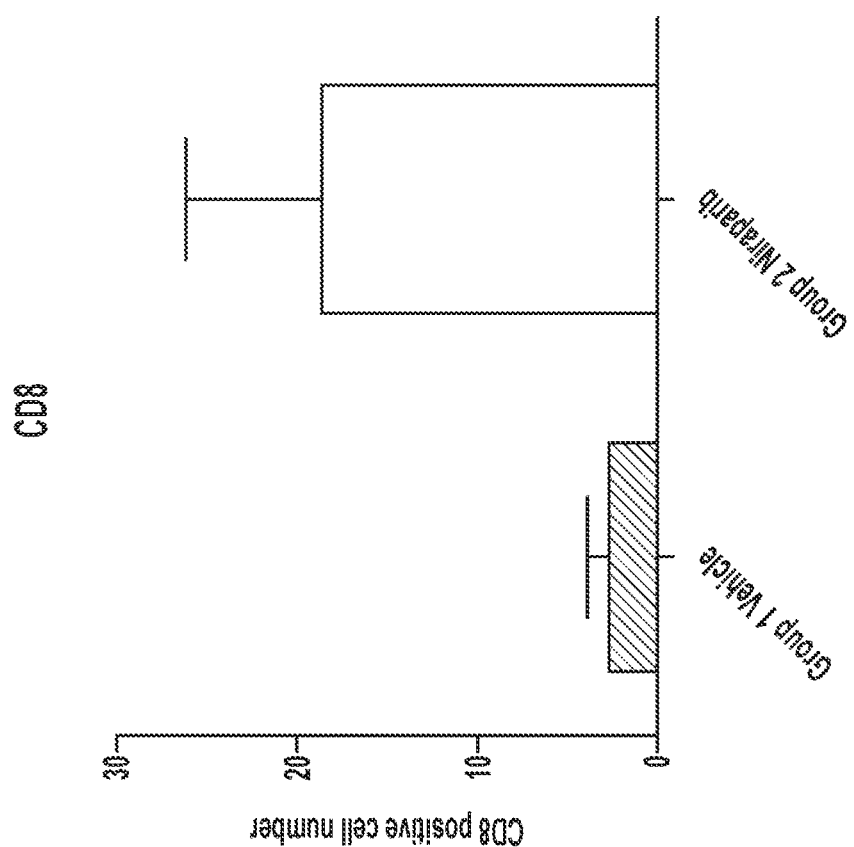
FIG. 2B depicts quantification of CD8 IHC staining images showing CD8 positive cell numbers in vehicle or niraparib treated mice.
Figure 3A:
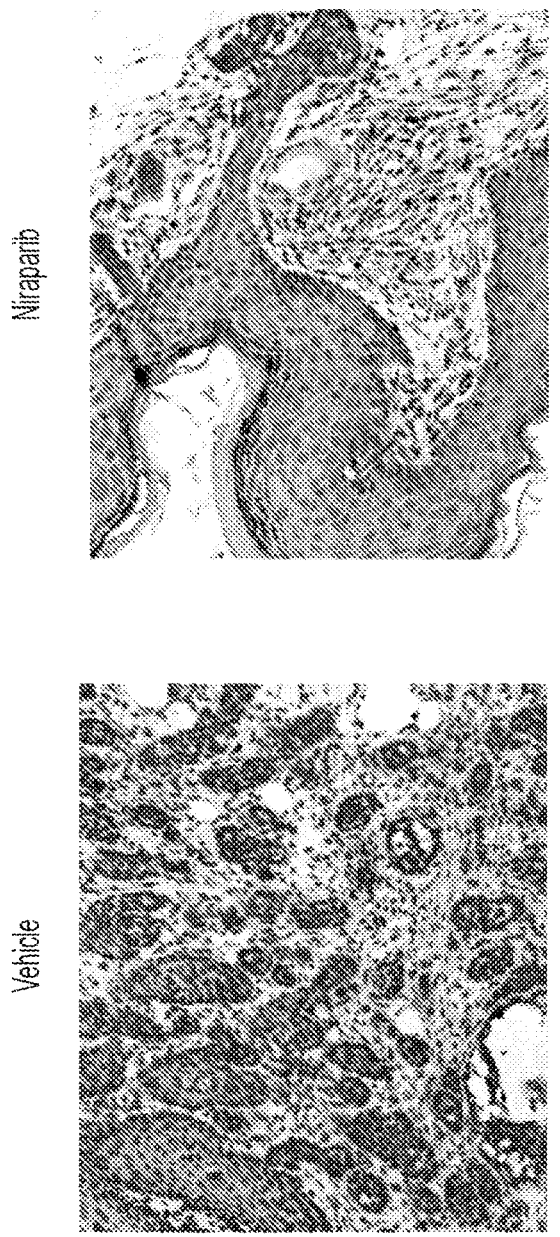
FIG. 3A depicts Foxp3 IHC staining on tumor samples developed from $Apc^{Min}$/J heterozygous background upon vehicle or niraparib treatment.
Figure 3B:
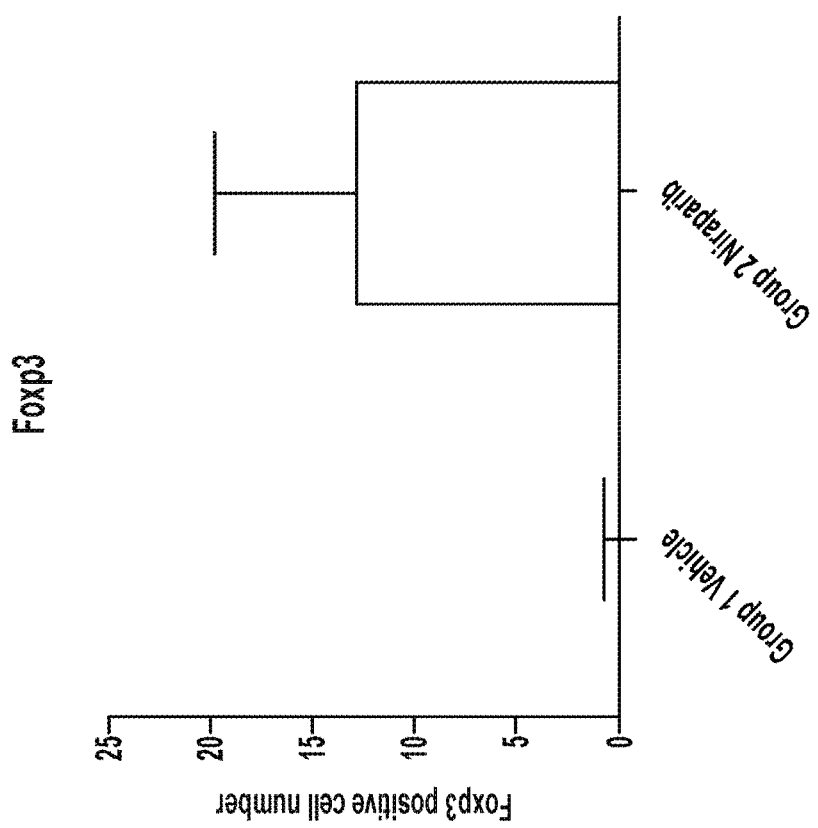
FIG. 3B depicts quantification of Foxp3 IHC staining images showing Foxp3 positive cell numbers in vehicle or niraparib treated mice.
Figure 4A:
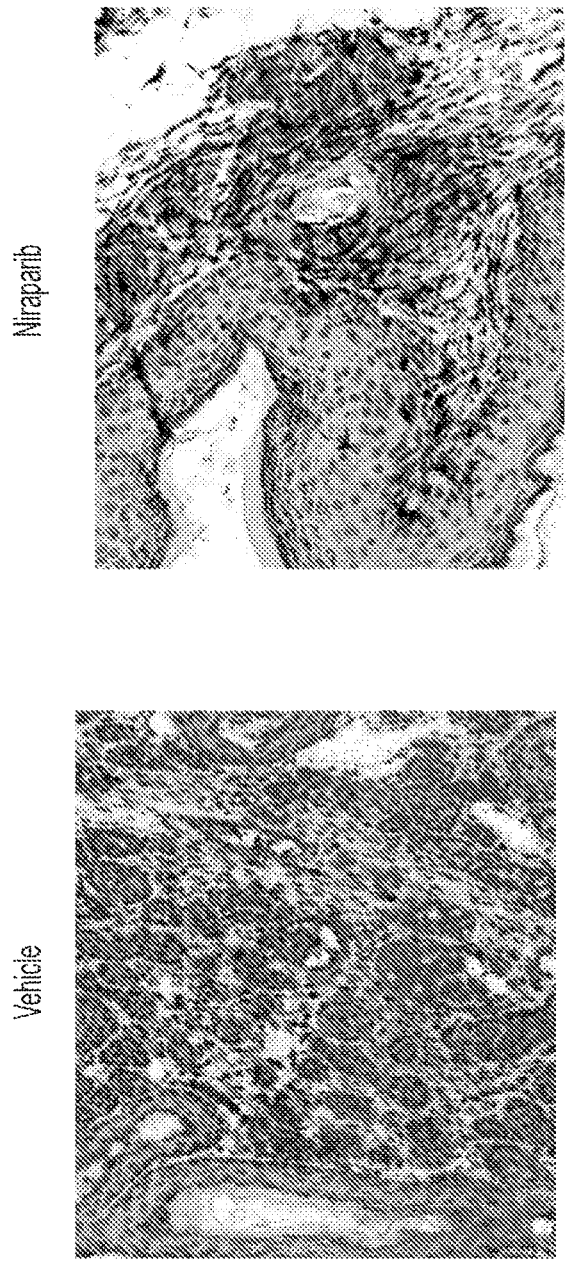
FIG. 4A depicts Iba1 IHC staining on tumor samples developed from $Apc^{Min}$/J heterozygous background upon vehicle or niraparib treatment.
Figure 4B:
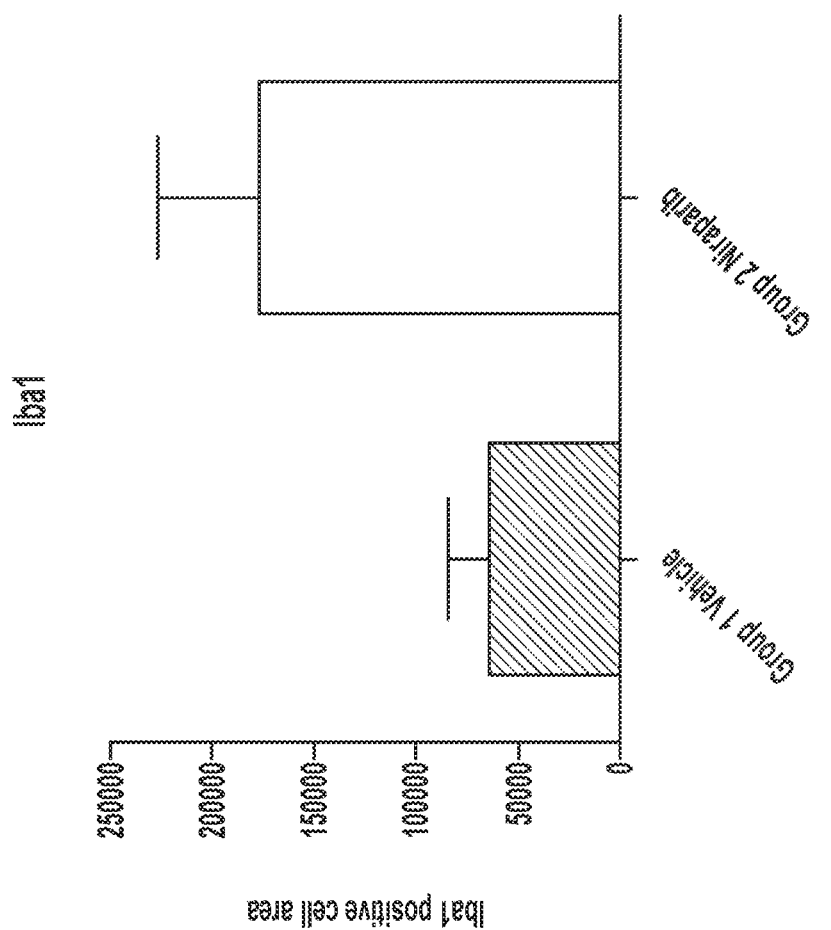
FIG. 4B depicts quantification of Iba1 IHC staining images showing Iba1 positive cell numbers in vehicle or niraparib treated mice.
Figure 5A:
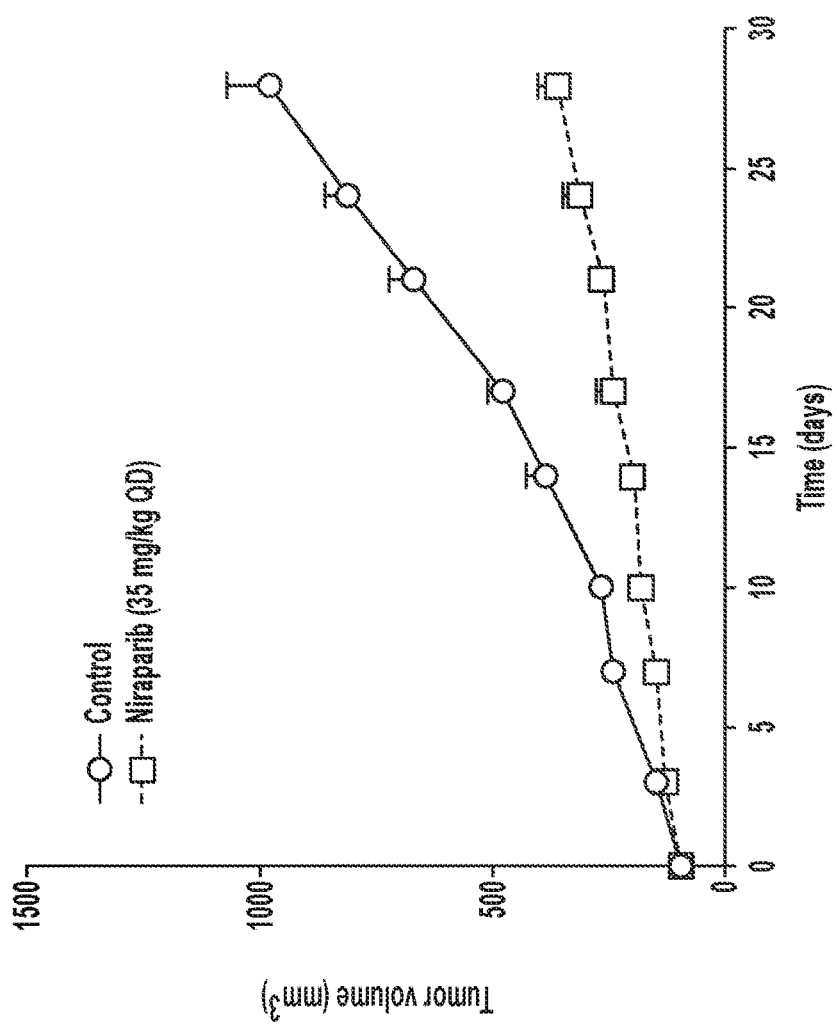
FIG. 5A depicts percentage of Ki67-positive CD4 and CD8 positive cells among total CD3 population in control or niraparib treated mice as assessed by flow cytometry.
Figure 5B:
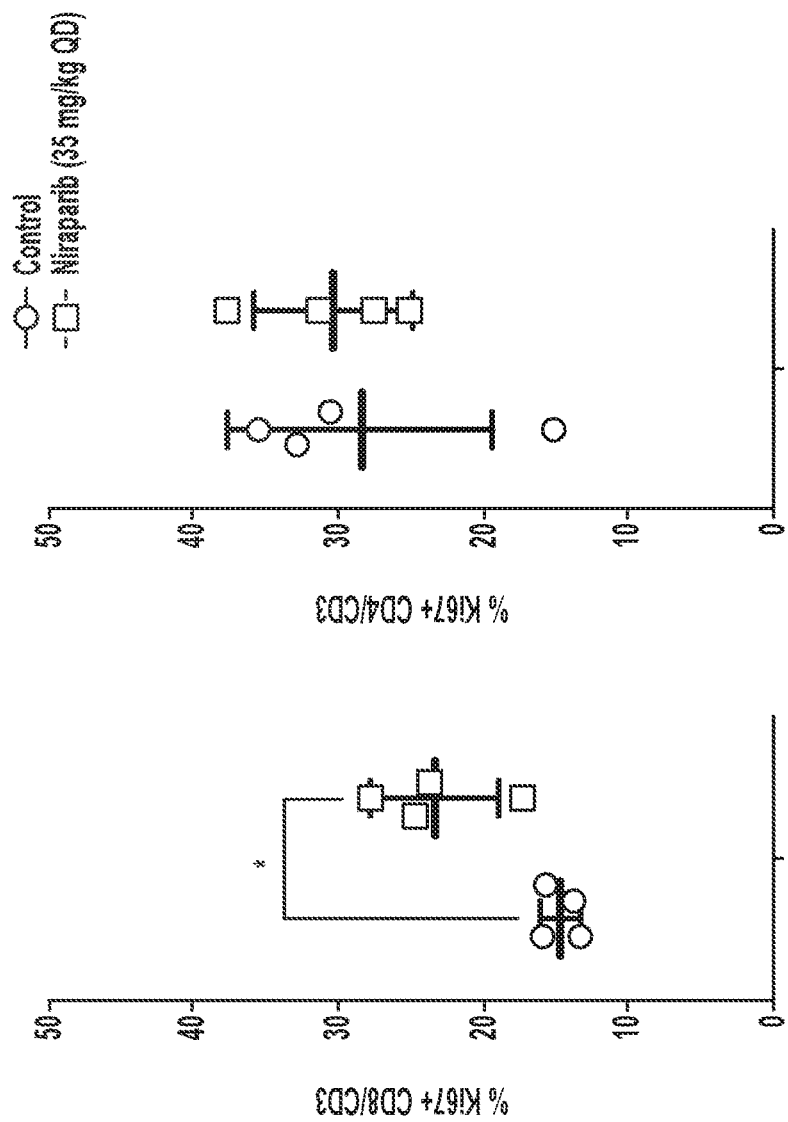
FIG. 5B depicts tumor volume in MDA-MB-436 huNOG-EXL mice treated with niraparib or control.

Increased expression of CD4, CD8, FoxP3, and Iba1 were observed in tumor samples obtained from mice treated with an agent that inhibits PARP signaling (e.g., niraparib) as compared to vehicle treated mice. These results can indicate an increased presence of CD4+ (see FIGS. 1A and 1B), CD8+ (see FIGS. 2A and 2B), Treg (see FIGS. 3A and 3B), and macrophage (see FIGS. 4A and 4B) cells upon administration of an agent that inhibits PARP signaling (e.g., niraparib) in an immuno-competent syngeneic mouse model. Similarly, increased percentage of CD8+ cells were observed in MDA-MB-436 huNOG-EXL mice treated with 35 mg/kg niraparib at QD×5/week (see FIG. 5A), which resulted in a reduction of tumor growth (see FIG. 5B). Thus, administration of an exemplary inhibitor of PARP signaling can enhance targeting of immune cells in the tumor microenvironment.

Example 2—Administration of an Agent that Regulates Activity in the Tumor Microenvironment Enhances the Anti-Tumor Activity of an Agent that Inhibits PARP This example describes the effects of treatment with an agent that inhibits PARP together with an agent that regulates activity in the tumor microenvironment in a mouse model of breast cancer. HuNOG-EXL mice inoculated with MDA-MB436 breast carcinoma cell line were orally administered: i) 80 mg/kg of niraparib tosylate once daily; ii) 200 mg/kg BLZ945 (an anti-CSF-1R that binds to CSF1R and inhibits CSF1R-mediated signal transduction pathways in tumor associated macrophages) on a 5 day on and 2 day off schedule; or iii) 80 mg/kg of niraparib tosylate and 200 mg/kg BLZ945 with the same dosing schedule as the single agent groups. Control mice were administered an isotype control antibody twice weekly via intraperitoneal injection.

Figure 6A:
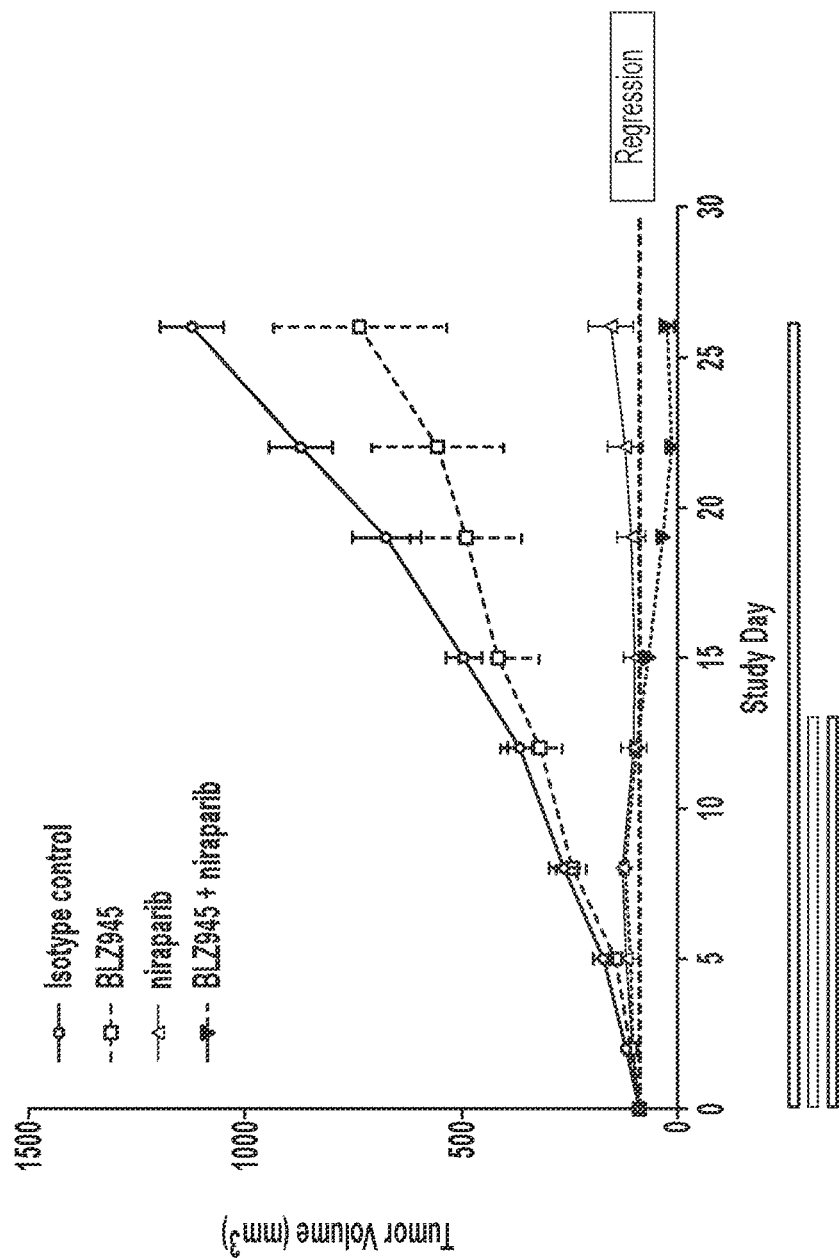
FIG. 6A depicts tumor volume in MDA-MB-436 huNOG-EXL mice treated with niraparib, BLZ945, niraparib and BLZ945, or control.
Figure 6B:
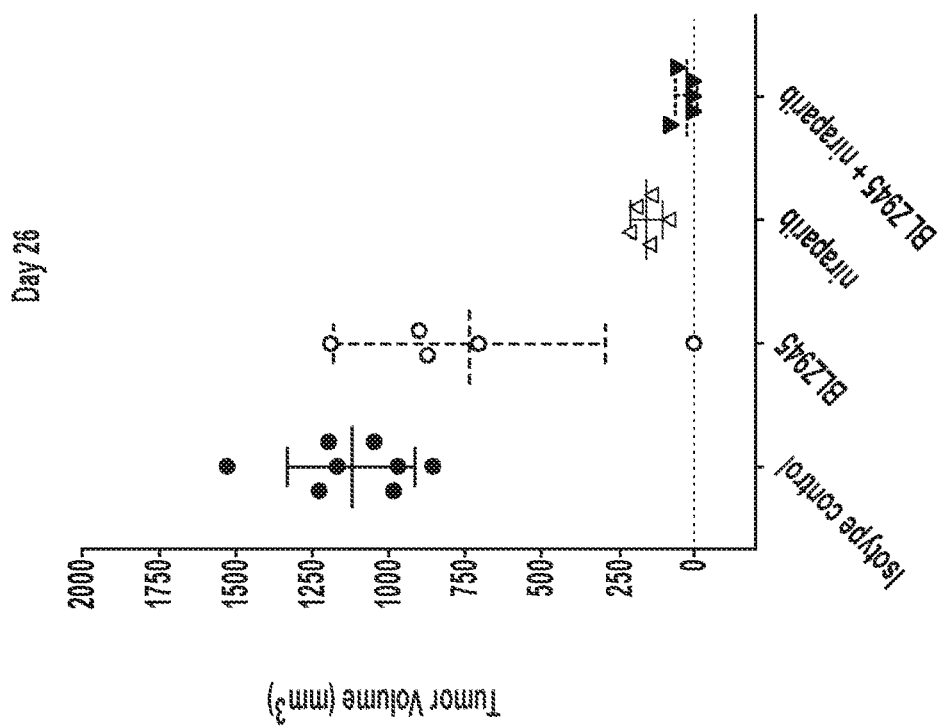
FIG. 6B depicts tumor volume on day 26 in MDA-MB-436 huNOG-EXL mice treated with niraparib, BLZ945, niraparib and BLZ945, or control.

Tumor volumes were recorded twice in a week with a gap of 2-3 days in between two measurements until tumor volume reached 600-1000 mm³ in the control mice. The results are shown in FIG. 6A, and tumor volume as measured on day 26 of the study is shown in FIG. 6B. Consistent with the data described in Example 1, these results indicate that BLZ945, an agent that regulates activity in the tumor microenvironment, enhances anti-tumor activity of niraparib, an agent that inhibits PARP.

EMBODIMENTS

1. A method of treating a subject with a disease or condition comprising administering to the subject
(a) a first agent that inhibits poly [ADP-ribose] polymerase (PARP); and
(b) a second agent, wherein the second agent comprises a regulatory T cell (Treg) inhibitory agent, a macrophage inhibitory agent, an antigen specific immune response enhancer agent, or a combination thereof.

2. A method of enhancing an immune response or increasing the activity of an immune cell in a subject with a disease or condition comprising administering to the subject
(a) a first agent that inhibits poly [ADP-ribose] polymerase (PARP); and
(b) a second agent, wherein the second agent comprises a regulatory T cell (Treg) inhibitory agent, a macrophage inhibitory agent, an antigen specific immune response enhancer agent, or a combination thereof.

3. A method of inducing an immune response in a subject with a disease or condition comprising administering to the subject
(a) a first agent that inhibits poly [ADP-ribose] polymerase (PARP); and
(b) a second agent, wherein the second agent comprises a regulatory T cell (Treg) inhibitory agent, a macrophage inhibitory agent, an antigen specific immune response enhancer agent, or a combination thereof.

4. The method of any one of embodiments 1-3, wherein the first agent inhibits PARP 1 and/or 2.

5. The method of any one of embodiments 1-4, wherein the first agent is a small organic or inorganic molecule; a saccharine; an oligosaccharide; a polysaccharide; a carbohydrate; a peptide; a protein; a peptide analog; a peptide derivative; a lipid; an antibody; an antibody fragment; a peptidomimetic; a nucleic acid; a nucleic acid analog; a nucleic acid derivative; an extract made from biological materials; a naturally occurring or synthetic composition; a metal; a toxin; or any combination thereof.

6. The method of any one of embodiments 1-5, wherein the first agent is a small molecule.

7. The method of any one of embodiments 1-6, wherein the first agent is selected from the group consisting of: ABT-767, AZD 2461, BGB-290, BGP 15, CEP 9722, E7016, E7449, fluzoparib, INO1001, JPI 289, MP 124, niraparib, olaparib, ONO2231, rucaparib, SC 101914, talazoparib, veliparib, WW 46, and salts or derivatives thereof.

8. The method of any one of embodiments 1-7, wherein the first agent is selected from the group consisting of: niraparib, olaparib, rucaparib, talazoparib, and veliparib, or salts or derivatives thereof.

9. The method of any one of embodiments 1-8, wherein the first agent comprises niraparib or a pharmaceutically acceptable salt or derivative thereof.

10. The method of any one of embodiments 1-9, wherein the Treg inhibitory agent inhibits or decreases the activity, function, or migration of a Treg cell.

11. The method of any one of embodiments 1-10, wherein the Treg inhibitory agent decreases a population of Treg cells in the subject.

12. The method of any one of embodiments 1-11, wherein the Treg inhibitory agent substantially ablates or eliminates a population of Treg cells in the subject.

13. The method of any one of embodiments 1-12, wherein the macrophage inhibitory agent inhibits or decreases the activity, function, or migration of a macrophage.

14. The method of any one of embodiments 1-13, wherein the macrophage inhibitory agent decreases a population of macrophage cells in the subject.

15. The method of any one of embodiments 1-14, wherein the macrophage inhibitory agent substantially ablates or eliminates a population of macrophage cells in the subject.

16. The method of any one of embodiments 1-15, wherein the Treg cell is an infiltrating T cell.

17. The method of any one of embodiments 1-16, wherein the macrophage comprises a tumor-associated macrophage (TAM).

18. The method of any one of embodiments 1-17, wherein the second agent enhances an antigen specific CD4+ T cell activity.

19. The method of any one of embodiments 1-18, wherein the second agent enhances an antigen specific CD8+ T cell activity.

20. The method of any one of embodiments 1-19, wherein the second agent is selected from the group consisting of a small organic or inorganic molecule; a saccharine; an oligosaccharide; a polysaccharide; a carbohydrate; a peptide; a protein; a peptide analog; a peptide derivative; a lipid; an antibody; an antibody fragment; a peptidomimetic; a nucleic acid; a nucleic acid analog; a nucleic acid derivative; an extract made from biological materials; a naturally occurring or synthetic composition; a metal; a toxin; and any combination thereof.

21. The method of any one of embodiments 1-20, wherein the administering comprises administering the first and second agent sequentially.

22. The method of any one of embodiments 1-20, wherein the administering comprises administering the first and second agent simultaneously.

23. The method of any one of embodiments 1-20, wherein the administering comprises administering the first agent before administering the second agent second agent.

24. The method of any one of embodiments 1-23, wherein the subject is a mammalian subject.

25. The method of any one of embodiments 1-24, wherein the subject is a human.

26. The method of any one of embodiments 1-25, wherein the second agent is a regulatory T cell (Treg) inhibitory agent selected from the group consisting of a Treg ablating agent, a Treg migration inhibitor agent, a Treg function inhibitor agent, and combinations thereof.

27. The method of embodiment 26, wherein the Treg ablating agent is selected from the group consisting of cyclophosphamide, paclitaxel, imatinib, sunitinib, sorafenib, dasatinib, temozolomide, daclizumab, denileukin diftitox, and combinations thereof.

28. The method of embodiment 26, wherein the Treg migration inhibitor agent is selected from the group consisting of AMD3100, mogamulizumab, casuarinin, fucoidan, and combinations thereof.

29. The method of embodiment 26, wherein the Treg function inhibitor agent is selected from the group consisting of an anti-CTLA4 agent (e.g., ipilimumab, tremelimumab), an anti-OX40 agent, an anti-GITR agent, an adenosine receptor antagonist (e.g., caffeine, theophylline, theobromine, and 8-phenylxanthines), P60, and combinations thereof.

30. The method of any one of embodiments 1-29, wherein the second agent is a macrophage inhibitory agent selected from the group consisting of a macrophage recruitment inhibitory agent, an M2 macrophage antisurvival agent, an M1 macrophage enhancing agent, an M2 to M1 polarizing agent, a macrophage activity inhibitor agent and combinations thereof.

31. The method of embodiment 30, wherein the macrophage recruitment inhibitory agent is selected from the group consisting of an anti-CCL2/CCR2 agent, an anti-IL6 agent, an anti-M-CSFR agent, and combinations thereof (e.g., an anti-M-CSFR agent).

32. The method of embodiment 31, wherein the macrophage recruitment inhibitory agent is selected from the group consisting of trabectedin, RS102895, PF-04136309, CNT0888, MLN1202, siltuximab, JNJ-28312141, GW2580, IMC-CS4 (LY3022855), emactuzumab, AMG820, pexidartinib, linifanib, OSI-930, CEP-32496, PLX7846, BLZ945, ARRY-382, JNJ-40346527, MCS110, PLX3397, PLX6134, PD-0360324, FPA008, and combinations thereof (e.g., BLZ945).

33. The method of embodiment 30, wherein the M2 macrophage antisurvival agent is selected from the group consisting of an MMP inhibitor, clodronate, zoledronic acid, dichloromethylene bisphosphonate, trabectedin, dasatinib, retinoic acid, attenuated bacteria (e.g., *Shigella flexneri, Salmonella typhimurium, Listeria monocytogens, Chlamydia psittaci, Legionella pneumophila*), and combinations thereof.

34. The method of embodiment 30, wherein the M1 macrophage enhancing agent or the M2 to M1 polarizing agent is selected from the group consisting of an anti-CD40 agent, an anti-IL-10R agent, a CD47 antagonist (e.g., Hu5F9-G4, CC-90002, and CD47-Fc fusion protein TTI-621), PolyI:C, LPS, monophosphoryl A, imiquimod, R-848, CpG-ODN, IFN-α, IFN-β, IFN-γ, GM-CSF, IL-12, IL-2, IL-15, Tα1, ibrutinib, EF-022 and combinations thereof.

35. The method of embodiment 30, wherein the macrophage activity inhibitory agent is selected from the group consisting of a STAT3 inhibitor, a STAT6 inhibitor, or an anti-tumor drug agent.

36. The method of embodiment 35, wherein the macrophage activity inhibitory agent is selected from the group consisting of WP1066, sunitinib, sorafenib, STA-21, IS3 295, S3I-M2001, AS1517499, leflunomide, TMC-264, histidine-rich glycoprotein (HRG), copper chelate (CuNG), 5,6-dimethylxanthenone-4-acetic acid (MDXAA), vadimezan (ASA404), cisplatin, silibinin, proton pump inhibitor pantoprazole (PPZ), CNI-1493 and combinations thereof.

37. The method of embodiment 30, wherein the macrophage inhibitor agent is an anti-IL-1α agent (e.g., xilonix).

38. The method of any one of embodiments 1-37, wherein the second agent is an antigen specific immune response enhancer agent selected from the group consisting of an anti-PD-1 agent, an anti-PD-L1 agent, a GITR (glucocorticoid-induced TNFR-related protein) stimulating agent, an anti-CTLA4 agent, an anti-TIM-3 agent, an anti-LAG-3 agent, an anti-IDO agent, an agent that enhances tumor antigen presentation (e.g., personalized cancer vaccine, autologous antigen presenting cell, autologous dendritic cells, artificial antigen presenting cell), a chemokine signaling agent, an anti-VEGF agent, a cytokine signal stimulating agent, and combinations thereof.

39. The method of embodiment 38, wherein the anti-PD-1 agent is selected from the group consisting of pembrolizumab, nivolumab, PDR001, REGN2810 (SAR-439684), BGB-A317, BI 754091, IBI308, INCSHR-1210, JNJ-63723283, JS-001, MEDI0680 (AMP-514), MGA-012, PF-06801591, REGN-2810, TSR-042, atezolizumab, avelumab, CX-072, durvalumab, FAZ053, LY3300054, PD-L1 millamolecule, PDR-001, camrelizumab (HR-301210), BCD-100, AGEN-2034, CS1001, Sym-021, LZMO09, KN-035, AB122, genolimzumab (CBT-501), AK 104, GLS-010, BGB-A333, SHR-1316, CK-301, and combinations thereof.

40. The method of embodiment 38 or 39, wherein the anti-PD-L1 agent is selected from the group consisting of atezolizumab, durvalumab, avelumab, LY3300054, BGB-A333, SHR-1316, CK-301, and combinations thereof.

41. The method of any one of embodiments 38-40, wherein the GITR stimulating agent is selected from the group consisting of DTA-1, mGITRL, pGITRL, and combinations thereof.

42. The method of any one of embodiments 38-41, wherein the anti-CTLA4 agent is selected from the group consisting of ipilimumab, tremelimumab, and combinations thereof.

43. The method of any one of embodiments 38-42, wherein the chemokine signaling agent is selected from the group consisting of CXCL16, a CXCR6 chemokine receptor (CD186) agonist, and combinations thereof.

44. The method of any one of embodiments 38-43, wherein the anti-VEGF agent is selected from the group consisting of bevacizumab, pazopanib, sunitinib, sorafenib, axitinib, ponatinib, regorafenib, cabozantinib, vandetanib, ramucirumab, lenvatinib, ziv-aflibercept, and combinations thereof.

45. The method of any one of embodiments 38-44, wherein the cytokine signal stimulating agent is an interleukin or an interferon.

46. The method of embodiment 45, wherein the interleukin is selected from the group consisting of IL-2, IL-1, IL-7, IL-15, IL-12, IL-18 and combinations thereof.

47. The method of embodiment 45, wherein the interferon is IFN alpha.

48. The method of any one of embodiments 1-47, wherein the second agent is an antigen specific immune response enhancer agent selected from the group consisting of a flavonoid (e.g., flavonoid glycoside), lidocaine, lamotrigine, sulfamethoxazole, phenytoin, carbamazepine, sulfamethoxazole, phenytoin, allopurinol, paracetamol, mepivacaine, p-phenylenediamine, ciprofloxacin and moxifloxacin.

49. The method of any one of embodiments 1-48, wherein the disease or condition is cancer.

50. The method of embodiment 49, wherein the cancer is selected from the group consisting of endometrial cancer, breast cancer, ovarian cancer, cervical cancer, fallopian tube cancer, primary peritoneal cancer, colon cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, squamous cell carcinoma of the head and neck, prostate cancer, pancreatic cancer, mesothelioma, sarcoma, hematological cancer, and combinations thereof.

51. The method of any one of embodiments 1-50, wherein the administering comprises administering a composition comprising a capsule comprising the first agent.

52. The method of embodiment 51, wherein the capsule comprises a formulation comprising the first agent and one or more pharmaceutically acceptable excipients.

53. The method of embodiment 52, wherein the one or more pharmaceutically acceptable excipients comprises lactose monohydrate, magnesium stearate, or a combination thereof.

54. The method of any one of embodiments 1-53, wherein a therapeutically effective amount of the first or second agent is administered.

55. The method of any one of embodiments 1-54, wherein the method further comprises administering a third agent to the subject or performing a therapy on the subject selected from the group consisting of surgery, radiotherapy, and combinations thereof.

56. The method of embodiment 55, wherein the third agent comprises an antigen specific immune response enhancer agent, an anti-angiogenic agent, a chemotherapeutic agent, or combinations thereof.

57. The method of embodiment 56, wherein the antigen specific immune response enhancer agent comprises an anti-PD-1 agent, an anti-PD-L1 agent, an anti-CTLA4 agent, an anti-TIM-3 agent, or an anti-LAG-3 agent.

58. The method of embodiment 56, wherein the anti-angiogenic agent is selected from the group consisting of TNP-470, platelet factor 4, thrombospondin-1, tissue inhibitors of metalloproteases (TIMP1 and TIMP2), prolactin, angiostatin, endostatin, bFGF soluble receptor, transforming growth factor beta, interferon alpha, soluble KDR and FLT-1 receptors, placental proliferin-related protein, and combinations thereof.

59. The method of embodiment 56, wherein the chemotherapeutic agent is selected from the group consisting of aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, vinorelbine, and combinations thereof.

60. A pharmaceutical composition comprising
(a) a first agent that inhibits poly [ADP-ribose] polymerase (PARP); and
(b) a second agent, wherein the second agent comprises a regulatory T cell (Treg) inhibitory agent, a macrophage inhibitory agent, an antigen specific immune response enhancer agent, or a combination thereof.

61. The pharmaceutical composition of embodiment 61, wherein the first agent inhibits PARP 1 and/or 2.

62. The pharmaceutical composition of embodiment 60 or 61, wherein the first agent is a small organic or inorganic molecule; a saccharine; an oligosaccharide; a polysaccharide; a carbohydrate; a peptide; a protein; a peptide analog; a peptide derivative; a lipid; an antibody; an antibody fragment; a peptidomimetic; a nucleic acid; a nucleic acid analog; a nucleic acid derivative; an extract made from biological materials; a naturally occurring or synthetic composition; a metal; a toxin; or any combination thereof.

63. The pharmaceutical composition of embodiment any one of embodiments 60-62, wherein the first agent is a small molecule.

64. The pharmaceutical composition of any one of embodiments 60-63, wherein the first agent is selected from the group consisting of: ABT-767, AZD 2461, BGB-290, BGP 15, CEP 9722, E7016, E7449, fluzoparib, INO1001, JPI 289, MP 124, niraparib, olaparib, ONO2231, rucaparib, SC 101914, talazoparib, veliparib, WW 46, and salts or derivatives thereof.

65. The pharmaceutical composition of any one of embodiments 60-64, wherein the first agent comprises niraparib or a pharmaceutically acceptable salt or derivative thereof.

66. The pharmaceutical composition of any one of embodiments 60-65, wherein the Treg inhibitory agent inhibits or decreases the activity, function, or migration of a Treg cell.

67. The pharmaceutical composition of any one of embodiments 60-66, wherein the Treg inhibitory agent decreases a population of Treg cells in the subject.

68. The pharmaceutical composition of any one of embodiments 60-67, wherein the Treg inhibitory agent substantially ablates or eliminates a population of Treg cells in the subject.

69. The pharmaceutical composition of any one of embodiments 60-68, wherein the macrophage inhibitory agent inhibits or decreases the activity, function, or migration of a macrophage.

70. The pharmaceutical composition of any one of embodiments 60-69, wherein the macrophage inhibitory agent decreases a population of macrophage cells in the subject.

71. The pharmaceutical composition of any one of embodiments 60-70, wherein the macrophage inhibitory agent substantially ablates or eliminates a population of macrophage cells in the subject.

72. The pharmaceutical composition of any one of embodiments 60-71, wherein the Treg cell is an infiltrating T cell.

73. The pharmaceutical composition of any one of embodiments 60-72, wherein the macrophage comprises a tumor-associated macrophage (TAM).

74. The pharmaceutical composition of any one of embodiments 60-73, wherein the second agent enhances an antigen specific CD4+ T cell activity.

75. The pharmaceutical composition of any one of embodiments 60-74, wherein the second agent enhances an antigen specific CD8+ T cell activity.

76. The pharmaceutical composition of any one of embodiments 60-75, wherein the second agent is selected from the group consisting of a small organic or inorganic molecule; a saccharine; an oligosaccharide; a polysaccharide; a carbohydrate; a peptide; a protein; a peptide analog; a peptide derivative; a lipid; an antibody; an antibody fragment; a peptidomimetic; a nucleic acid; a nucleic acid analog; a nucleic acid derivative; an extract made from biological materials; a naturally occurring or synthetic composition; a metal; a toxin; and any combination thereof.

77. The pharmaceutical composition of any one of embodiments 60-76, wherein the second agent is a regulatory T cell (Treg) inhibitory agent selected from the group consisting of a Treg ablating agent, a Treg migration inhibitor agent, a Treg function inhibitor agent, and combinations thereof.

78. The pharmaceutical composition of embodiment 79, wherein the Treg ablating agent is selected from the group consisting of cyclophosphamide, paclitaxel, imatinib, sunitinib, sorafenib, dasatinib, temozolomide, daclizumab, denileukin diftitox, and combinations thereof.

79. The pharmaceutical composition of embodiment 79, wherein the Treg migration inhibitor agent is selected from the group consisting of AMD3100, mogamulizumab, casuarinin, fucoidan, and combinations thereof.

80. The pharmaceutical composition of embodiment 79, wherein the Treg function inhibitor agent is selected from the group consisting of an anti-CTLA4 agent (e.g., ipilimumab, tremelimumab), an anti-OX40 agent, an anti-GITR agent, an adenosine receptor antagonist (e.g., caffeine, theophylline, theobromine, and 8-phenylxanthines), P60, and combinations thereof.

81. The pharmaceutical composition of any one of embodiments 60-80, wherein the second agent is a macrophage inhibitory agent selected from the group consisting of a macrophage recruitment inhibitory agent, an M2 macrophage antisurvival agent, an M1 macrophage enhancing agent, an M2 to M1 polarizing agent, a macrophage activity inhibitor agent and combinations thereof.

82. The pharmaceutical composition of embodiment 81, wherein the macrophage recruitment inhibitory agent is selected from the group consisting of an anti-CCL2/CCR2 agent, an anti-IL6 agent, an anti-M-CSFR agent, and combinations thereof (e.g., an anti-M-CSFR agent).

83. The pharmaceutical composition of embodiment 82, wherein the macrophage recruitment inhibitory agent is selected from the group consisting of trabectedin, RS102895, PF-04136309, CNT0888, MLN1202, siltuximab, JNJ-28312141, GW2580, IMC-CS4 (LY3022855), emactuzumab, AMG820, pexidartinib, linifanib, OSI-930, CEP-32496, PLX7846, BLZ945, ARRY-382, JNJ-40346527, MCS110, PLX3397, PLX6134, PD-0360324, FPA008, and combinations thereof (e.g., BLZ945).

84. The pharmaceutical composition of embodiment 81, wherein the M2 macrophage antisurvival agent is selected from the group consisting of an MMP inhibitor, clodronate, zoledronic acid, dichloromethylene bisphosphonate, trabectedin, dasatinib, retinoic acid, attenuated bacteria (e.g., *Shigella flexneri, Salmonella typhimurium, Listeria monocytogens, Chlamydia psittaci, Legionella pneumophila*), and combinations thereof.

85. The pharmaceutical composition of embodiment 81, wherein the M1 macrophage enhancing agent or the M2 to M1 polarizing agent is selected from the group consisting of an anti-CD40 agent, an anti-IL-10R agent, a CD47 antagonist (e.g., Hu5F9-G4, CC-90002, and CD47-Fc fusion protein TTI-621), PolyI:C, LPS, monophosphoryl A, imiquimod, R-848, CpG-ODN, IFN-α, IFN-γ, GM-CSF, IL-12, IL-2, IL-15, Tα1, ibrutinib, EF-022 and combinations thereof.

86. The pharmaceutical composition of embodiment 81, wherein the macrophage activity inhibitory agent is selected from the group consisting of a STAT3 inhibitor, a STAT6 inhibitor, or an anti-tumor drug agent.

87. The pharmaceutical composition of embodiment 86, wherein the macrophage activity inhibitory agent is selected from the group consisting of WP1066, sunitinib, sorafenib, STA-21, IS3 295, S3I-M2001, AS1517499, leflunomide, TMC-264, histidine-rich glycoprotein (HRG), copper chelate (CuNG), 5,6-dimethylxanthenone-4-acetic acid (MDXAA), vadimezan (ASA404), cisplatin, silibinin, proton pump inhibitor pantoprazole (PPZ), CNI-1493 and combinations thereof.

88. The pharmaceutical composition of embodiment 81, wherein the macrophage inhibitor agent is an anti-IL-1α agent (e.g., xilonix).

89. The pharmaceutical composition of any one of embodiments 60-88, wherein the second agent is an antigen specific immune response enhancer agent selected from the group consisting of an anti-PD-1 agent, an anti-PD-L1 agent, a GITR (glucocorticoid-induced TNFR-related protein) stimulating agent, an anti-CTLA4 agent, an anti-TIM-3 agent, an anti-LAG-3 agent, an anti-IDO agent, an agent that enhances tumor antigen presentation (e.g., personalized cancer vaccine, autologous antigen presenting cell, autologous dendritic cells, artificial antigen presenting cell), a chemokine signaling agent, an anti-VEGF agent, a cytokine signal stimulating agent, and combinations thereof.

90. The pharmaceutical composition of embodiment, 94, wherein the anti-PD-1 agent is selected from the group consisting of pembrolizumab, nivolumab, PDR001, REGN2810 (SAR-439684), BGB-A317, BI 754091, IBI308, INCSHR-1210, JNJ-63723283, JS-001, MEDI0680 (AMP-514), MGA-012, PF-06801591, REGN-2810, TSR-042, atezolizumab, avelumab, CX-072, durvalumab, FAZ053, LY3300054, PD-L1 millamolecule, PDR-001, camrelizumab (HR-301210), BCD-100, AGEN-2034, CS1001, Sym-021, LZMO09, KN-035, AB122, genolimzumab (CBT-501), AK 104, GLS-010, BGB-A333, SHR-1316, CK-301, and combinations thereof.

91. The pharmaceutical composition of embodiment 94 or 95, wherein the anti-PD-L1 agent is selected from the group consisting of atezolizumab, durvalumab, avelumab, LY3300054, BGB-A333, SHR-1316, CK-301, and combinations thereof.

92. The pharmaceutical composition of any one of embodiments 89-91, wherein the GITR stimulating agent is selected from the group consisting of DTA-1, mGITRL, pGITRL, and combinations thereof.

93. The pharmaceutical composition of any one of embodiments 89-92, wherein the anti-CTLA4 agent is selected from the group consisting of ipilimumab, tremelimumab, and combinations thereof.

94. The pharmaceutical composition of any one of embodiments 89-93, wherein the chemokine signaling agent is selected from the group consisting of CXCL16, a CXCR6 chemokine receptor (CD186) agonist, and combinations thereof.

95. The pharmaceutical composition of any one of embodiments 89-94, wherein the anti-VEGF agent is selected from the group consisting of bevacizumab, pazopanib, sunitinib, sorafenib, axitinib, ponatinib, regorafenib, cabozantinib, vandetanib, ramucirumab, lenvatinib, ziv-aflibercept, and combinations thereof.

96. The pharmaceutical composition of any one of embodiments 89-95, wherein the cytokine signal stimulating agent is an interleukin or an interferon.

97. The pharmaceutical composition of embodiment 96, wherein the interleukin is selected from the group consisting of IL-2, IL-1, IL-7, IL-15, IL-12, IL-18 and combinations thereof.

98. The pharmaceutical composition of embodiment 96, wherein the interferon is IFN alpha.

99. The pharmaceutical composition of any one of embodiments 60-98, wherein the second agent is an antigen specific immune response enhancer agent selected from the group consisting of a flavonoid (e.g., flavonoid glycoside), lidocaine, lamotrigine, sulfamethoxazole, phenytoin, carbamazepine, sulfamethoxazole, phenytoin, allopurinol, paracetamol, mepivacaine, p-phenylenediamine, ciprofloxacin and moxifloxacin.

100. The pharmaceutical composition of embodiment 99, wherein the disease or condition is cancer.

101. The pharmaceutical composition of embodiment 99, wherein the cancer is selected from the group consisting of endometrial cancer, breast cancer, ovarian cancer, cervical cancer, fallopian tube cancer, primary peritoneal cancer, colon cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, squamous cell carcinoma of the head and neck, prostate cancer, pancreatic cancer, mesothelioma, sarcoma, a hematological cancer, and combinations thereof.

102. The pharmaceutical composition of any one of embodiments 60-101, wherein the administering comprises administering a composition comprising a capsule comprising the first agent.

103. The pharmaceutical composition of embodiment 102, wherein the capsule comprises a formulation comprising the first agent and one or more pharmaceutically acceptable excipients.

104. The pharmaceutical composition of embodiment 103, wherein the one or more pharmaceutically acceptable excipients comprises lactose monohydrate, magnesium stearate, or a combination thereof.

105. The pharmaceutical composition of any one of embodiments 60-104, wherein a therapeutically effective amount of the first or second agent is administered.

106. The pharmaceutical composition of any one of embodiments 60-105, wherein the method further comprises administering a third agent to the subject.

107. The pharmaceutical composition of embodiment 106, wherein the third agent comprises an antigen specific immune response enhancer agent, an anti-angiogenic agent, a chemotherapeutic agent, or combinations thereof.

108. The pharmaceutical composition of embodiment 107, wherein the antigen specific immune response enhancer agent comprises an anti-PD-1 agent, an anti-PD-L1 agent, an anti-CTLA4 agent, an anti-TIM-3 agent, or an anti-LAG-3 agent.

109. The pharmaceutical composition of embodiment 107, wherein the anti-angiogenic agent is selected from the group consisting of TNP-470, platelet factor 4, thrombospondin-1, tissue inhibitors of metalloproteases (TIMP1 and TIMP2), prolactin, angiostatin, endostatin, bFGF soluble receptor, transforming growth factor beta, interferon alpha, soluble KDR and FLT-1 receptors, placental proliferin-related protein, and combinations thereof.

110. The pharmaceutical composition of embodiment 109, wherein the chemotherapeutic agent is selected from the group consisting of aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, vinorelbine, and combinations thereof.

What is claimed is:

1. A pharmaceutical composition comprising
   (a) a first agent that inhibits poly [ADP-ribose] polymerase (PARP); and
   (b) a second agent, wherein the second agent is an antigen specific immune response enhancer agent selected from the group consisting of a flavonoid, lidocaine, lamotrigine, sulfamethoxazole, phenytoin, carbamazepine, sulfamethoxazole, phenytoin, allopurinol, paracetamol, mepivacaine, p-phenylenediamine, ciprofloxacin and moxifloxacin.

2. The pharmaceutical composition of claim 1, wherein the first agent is selected from the group consisting of: niraparib, olaparib, rucaparib, talazoparib, and veliparib, or pharmaceutically acceptable salts or derivatives thereof.

3. The pharmaceutical composition of claim 2, wherein the first agent comprises niraparib or a pharmaceutically acceptable salt or derivative thereof.

4. The pharmaceutical composition of claim 2, wherein the first agent comprises olaparib or a pharmaceutically acceptable salt or derivative thereof.

5. A method of treating cancer in a human in need thereof comprising administering to the human a therapeutically effective amount of the pharmaceutical composition according to claim 1, wherein the method of treating cancer does not encompass prevention of cancer.

6. The method of claim 5, wherein the cancer is selected from the group consisting of endometrial cancer, breast cancer, ovarian cancer, cervical cancer, fallopian tube cancer, primary peritoneal cancer, colon cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, squamous cell carcinoma of the head and neck, prostate cancer, pancreatic cancer, mesothelioma, sarcoma, hematological cancer, and combinations thereof.

7. The method of claim 6, wherein the cancer is selected from the group consisting of breast cancer, ovarian cancer, and lung cancer.

8. The method of claim 5, wherein the first agent is selected from the group consisting of: niraparib, olaparib, rucaparib, talazoparib, and veliparib, or pharmaceutically acceptable salts or derivatives thereof.

9. The method of claim 8, wherein the first agent comprises niraparib or a pharmaceutically acceptable salt or derivative thereof.

10. The method of claim 8, wherein the first agent comprises olaparib or a pharmaceutically acceptable salt or derivative thereof.

* * * * *